US012767983B2

(12) United States Patent
Evans et al.

(10) Patent No.: US 12,767,983 B2
(45) Date of Patent: Oct. 20, 2026

(54) ASYMMETRIC RHODAMINE DYE AND USE THEREOF IN BIOLOGICAL ASSAYS

(71) Applicant: Life Technologies Corporation, Carlsbad, CA (US)

(72) Inventors: Brian Evans, Mountain View, CA (US); Scott Benson, Alameda, CA (US)

(73) Assignee: Life Technologies Corporation, Carlsbad, CA (US)

(*) Notice: Subject to any disclaimer, the term of this patent is extended or adjusted under 35 U.S.C. 154(b) by 1188 days.

(21) Appl. No.: 17/299,671

(22) PCT Filed: Dec. 20, 2019

(86) PCT No.: PCT/US2019/068111
§ 371 (c)(1),
(2) Date: Jun. 3, 2021

(87) PCT Pub. No.: WO2020/132607
PCT Pub. Date: Jun. 25, 2020

(65) Prior Publication Data

US 2022/0380845 A1 Dec. 1, 2022

Related U.S. Application Data

(60) Provisional application No. 62/782,445, filed on Dec. 20, 2018.

(51) Int. Cl.
*C09B 11/24* (2006.01)
*C07H 21/00* (2006.01)
*C12Q 1/6876* (2018.01)
*C12Q 1/6853* (2018.01)

(52) U.S. Cl.
CPC ........... *C12Q 1/6876* (2013.01); *C07H 21/00* (2013.01); *C09B 11/24* (2013.01); *C12Q 1/6853* (2013.01); *C12Q 2600/16* (2013.01)

(58) Field of Classification Search
CPC ........................................................ C09B 11/24
See application file for complete search history.

(56) References Cited

U.S. PATENT DOCUMENTS 3,929,825 A * 12/1975 Spatz .................... B41M 5/1455 428/323
5,231,191 A 7/1993 Woo et al.
5,945,526 A 8/1999 Lee et al.
6,649,769 B2 * 11/2003 Lee ........................ C07H 21/00 435/6.12
2012/0016128 A1 1/2012 Diwu et al.

FOREIGN PATENT DOCUMENTS

EP 552108 A2 * 7/1993 ......... G01N 21/6408
JP 2001508494 A 6/2001
JP 2014534261 A 12/2014
WO WO-9915517 A1 4/1999
WO WO-2012074693 A1 6/2012
WO WO-2013078244 A1 5/2013
WO WO-2015139577 A1 9/2015

OTHER PUBLICATIONS

Karpiuk "Photophysics of the Lactone Form of Rhodamine 101" J. Phys. Chem. 1994, 98, 3247-3256.*
Liu "Rational design and synthesis of a novel class of highly fluorescent rhodamine dyes that have strong absorption at long wavelengths" Tetrahedron Letters 44 (2003) 4355-4359.*
Zhang "New near-infrared rhodamine dyes with large Stokes shifts for sensitive sensing of intracellular pH changes and fluctuations" Chem. Commun., 2018, 54, 7625, first published Jun. 7, 2018.*
Obukhova "Absorption, fluorescence, and acid-base equilibria of rhodamines in micellar media of sodium dodecyl sulfate" Spectrochimica Acta Part A: Molecular and Biomolecular Spectroscopy 170 (2017) 138-144.*
Greene and Wuts, Protective Groups in Organic Synthesis 3rd edition Wiley: New York, 1999 pp. 494-631.*
Supplementary data to the paper: Obukhova "Absorption, Fluorescence, and Acid-Base Equilibria of Rhodamines in Micellar Media of Sodium Dodecyl Sulfate" Spectrochimica Acta Part A: Molecular and Biomolecular Spectroscopy vol. 170, Jan. 5, 2017, pp. 1-7.*
PCT/US2019/068111, International Search Report and Written Opinion, May 4, 2020, 16 pages.

(Continued)

*Primary Examiner* — David K O'Dell
(74) *Attorney, Agent, or Firm* — Klarquist Sparkman, LLP

(57) ABSTRACT

The present disclosure relates to N-protected NH-rhodamine dyes and their use in nucleic acid detection. In particular, the disclosure relates to methods of making N-protected NH-rhodamine dyes, and methods of use of N-protected NH-rhodamine dyes (e.g., human identification). Certain dyes provided herein have unique spectral properties that complement those in existing dye sets and can be used to expand the number of reporter dyes that can be included for HID applications and other biological assays. Those fluorescent compounds are useful to label synthetic oligonucleotides. Formula (I).

(I)

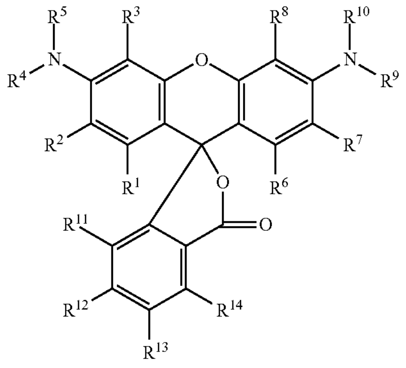

1 Claim, 11 Drawing Sheets

(56) References Cited

OTHER PUBLICATIONS

Office Action for European Application No. 19842699.1, mailed Sep. 15, 2025.

* cited by examiner

ASYMMETRIC RHODAMINE DYE AND USE THEREOF IN BIOLOGICAL ASSAYS

1. BACKGROUND

Using fluorescent rhodamine dyes as detection labels has found widespread use in molecular biology, cell biology and molecular genetics. For example, using fluorescently-labeled oligonucleotides is now widespread in a variety of different assays, including polynucleotide sequencing, fluorescence in situ hybridization (FISH), hybridization assays on nucleic acid arrays, fluorescence polarization studies, and nucleic acid amplification assays, including polymerase chain amplification assays carried out with fluorescent probes and/or primers.

A variety of multiplex assay systems have been described utilizing fluorescent dyes. For example, rhodamine dyes have been described for use in multiplex assay systems, such as those described in WO 2012/067901 for use in human identification assays (HID). Unfortunately, the spectral characteristics of existing dye sets including rhodamine dyes has limited the ability to develop robust and sensitive assay systems using greater than 6-dyes in combination. To enable such higher-plex systems, there is a need for the development of new rhodamine dyes having spectral properties uniquely suited to the creation of such alternative multiplex dye sets.

2. SUMMARY

Fluorescent compounds are described that can be used to label synthetic oligonucleotides. In one embodiment, the compound has the formula (I)

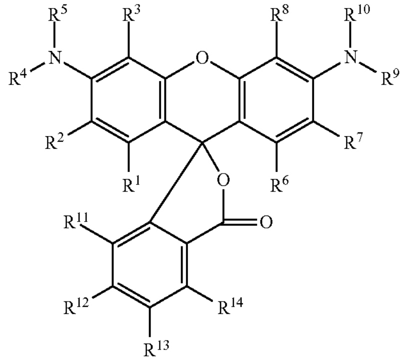

wherein $R^1$, $R^2$, $R^3$, $R^6$, $R^7$, $R^8$, $R^{11}$, $R^{12}$, $R^{13}$, and $R^{14}$, when taken alone, are each independently of one another selected from hydrogen, lower alkyl, (C6-C14) aryl, (C7-C20) arylalkyl, 5-14 membered heteroaryl, 6-20 membered heteroarylalkyl, —$R^b$, or —$(CH_2)_n$—$R^b$—; or alternatively, $R^1$ and $R^2$ and/or $R^6$ and $R^7$ are taken together with the carbon atoms to which they are bonded to form an optionally substituted benzo group;

$R^4$, when taken alone, is selected from hydrogen, lower alkyl, (C6-C14) aryl, (C7-C20) arylalkyl, 5-14 membered heteroaryl, 6-20 membered heteroarylalkyl; or $R^4$ and one of $R^2$ or $R^3$ are taken together with the atoms to which they are bonded to form an optionally substituted heterocycloalkyl group, an optionally substituted heterocycloalkenyl group, or an optionally substituted heteroaryl group;

$R^5$ is H or a protecting group;

$R^9$, when taken alone, is selected from hydrogen, lower alkyl, (C6-C14) aryl, (C7-C20) arylalkyl, 5-14 membered heteroaryl, 6-20 membered heteroarylalkyl; or $R^7$ and $R^9$ are taken together with the atoms to which they are bonded to form an optionally substituted heterocycloalkyl group, an optionally substituted heterocycloalkenyl group, or an optionally substituted heteroaryl group;

$R^{10}$ is H or protecting group; or $R^8$ and $R^{10}$ are taken together with the atoms to which they are bonded to form an optionally substituted heterocycloalkyl group, an optionally substituted heterocycloalkenyl group, or an optionally substituted heteroaryl group;

at least one of $R^7$ and $R^9$ or $R^8$ and $R^{10}$ are taken together with the atoms to which they are bonded to form an optionally substituted heterocycloalkyl group, an optionally substituted heterocycloalkenyl group, or an optionally substituted heteroaryl group, and optionally, $R^4$ and one of $R^2$ or $R^3$ are taken together with the atoms to which they are bonded to form an optionally substituted heterocycloalkyl group, an optionally substituted heterocycloalkenyl group, or an optionally substituted heteroaryl group with the proviso that compound is not of the formula

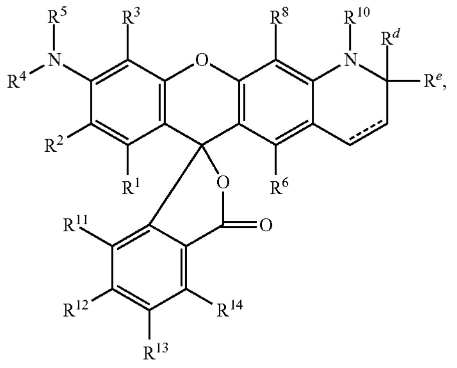

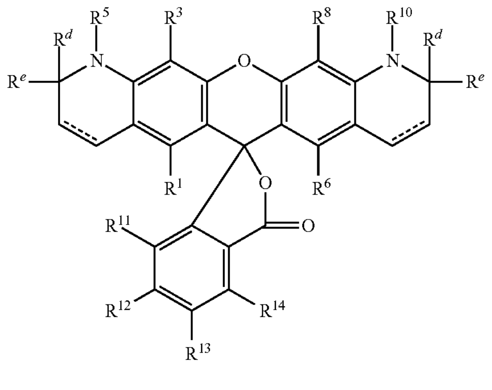 or

-continued

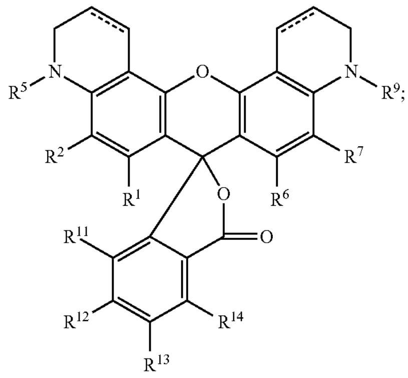

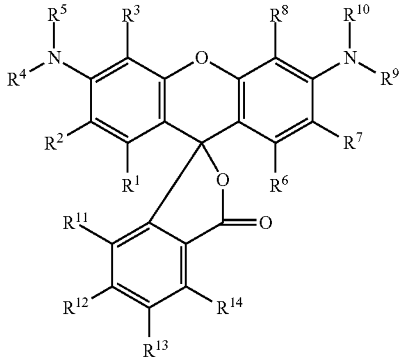

each $R^a$ is independently selected from lower alkyl, (C6-C14) aryl, (C7-C20) arylalkyl, 5-14 membered heteroaryl, $—CX_3$ and 6-20 membered heteroarylalkyl;

each $R^b$ is independently selected from —X, —OH, $—OR^a$, —SH, $—SR^a—NH_2$, $—NHR^a$, $—NR^cR^c$, $—N^+R^cR^cR^c$, perhalo lower alkyl, trihalomethyl, trifluoromethyl, $—P(O)(OH)_2$, $—P(O)(OR^a)_2$, $P(O)(OH)(OR^a)$, $—OP(O)(OH)_2$, $—OP(O)(OR^a)_2$, $—OP(O)(OR^a)(OH)$, $—S(O)_2OH$, $—S(O)_2R^a$, —C(O)H, $—C(O)R^a$, —C(S)X, $—C(O)OR^a$, —C(O)OH, $—C(O)NH_2$, $—C(O)NHR^a$, $—C(O)NR^cR^c$, $—C(S)NH_2$, $—C(O)NHR^a$, $—C(O)NR^cR^c$, $—C(NH)NH_2$, $—C(NH)NHR^a$, and $—C(NH)NR^cR^c$, each $R^c$ is independently an $R^a$, or, alternatively, two $R^c$ bonded to the same nitrogen atom may be taken together with that nitrogen atom to form a 5- to 8-membered saturated or unsaturated ring that may optionally include one or more of the same or different ring heteroatoms, which are typically selected from O, N and S;

each $R^d$ and $R^e$, when taken alone, is independently selected from hydrogen, lower alkyl, (C6-C14) aryl, (C7-C20) arylalkyl, 5-14 membered heteroaryl, 6-20 membered heteroarylalkyl, $—R^b$, or $—(CH_2)_n—R^b—$; and n is an integer ranging from 1 to 10.

In another aspect, the present disclosure describes oligonucleotide comprising a label moiety produced by reacting an oligonucleotide attached to a solid support with a reagent have a structure of formula:

LM-L-PEP wherein PEP is a phosphate ester precursor group, L is an optional linker linking the label moiety to the PEP group, and LM comprises an N-protected NH-rhodamine moiety of the formula (I)

wherein $R^1$, $R^2$, $R^3$, $R^6$, $R^7$, $R^8$, $R^{11}$, $R^{12}$, $R^{13}$, and $R^{14}$, when taken alone, are each independently of one another selected from hydrogen, lower alkyl, (C6-C14) aryl, (C7-C20) arylalkyl, 5-14 membered heteroaryl, 6-20 membered heteroarylalkyl, $—R^b$, or $—(CH_2)_n—R^b$; or alternatively, $R^1$ and $R^2$ and/or $R^6$ and $R^7$ are taken together with the carbon atoms to which they are bonded to form an optionally substituted benzo group; and one of $R^2$, $R^3$, $R^7$, $R^8$, $R^{12}$, or $R^{13}$ comprises a group of the formula —Y—, wherein Y is selected from the group consisting of —C(O)—, $—S(O)_2—$, —S— and —NH—;

$R^4$, when taken alone, is selected from hydrogen, lower alkyl, (C6-C14) aryl, (C7-C20) arylalkyl, 5-14 membered heteroaryl, 6-20 membered heteroarylalkyl; or $R^4$ and one of $R^2$ or $R^3$ are taken together with the atoms to which they are bonded to form an optionally substituted heterocycloalkyl group, an optionally substituted heterocycloalkenyl group, or an optionally substituted heteroaryl group;

$R^5$ is H or a protecting group;

$R^9$, when taken alone, is selected from hydrogen, lower alkyl, (C6-C14) aryl, (C7-C20) arylalkyl, 5-14 membered heteroaryl, 6-20 membered heteroarylalkyl; or $R^7$ and $R^9$ are taken together with the atoms to which they are bonded to form an optionally substituted heterocycloalkyl group, an optionally substituted heterocycloalkenyl group, or an optionally substituted heteroaryl group;

$R^{10}$ is H or protecting group; or $R^8$ and $R^{10}$ are taken together with the atoms to which they are bonded to form an optionally substituted heterocycloalkyl group, an optionally substituted heterocycloalkenyl group, or an optionally substituted heteroaryl group;

at least one of $R^7$ and $R^9$ or $R^8$ and $R^{10}$ are taken together with the atoms to which they are bonded to form an optionally substituted heterocycloalkyl group, an optionally substituted heterocycloalkenyl group, or an optionally substituted heteroaryl group, and optionally, $R^4$ and one of $R^2$ or $R^3$ are taken together with the atoms to which they are bonded to form an optionally substituted heterocycloalkyl group, an optionally substituted heterocycloalkenyl group, or an optionally substituted heteroaryl group, with the proviso that compound is not of the formula

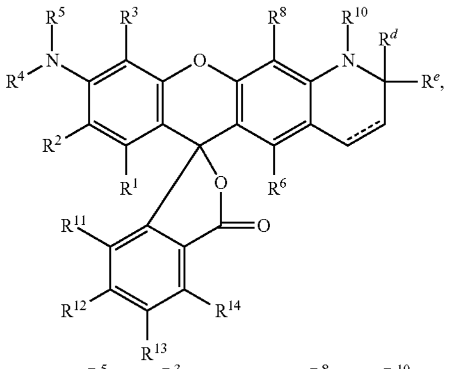

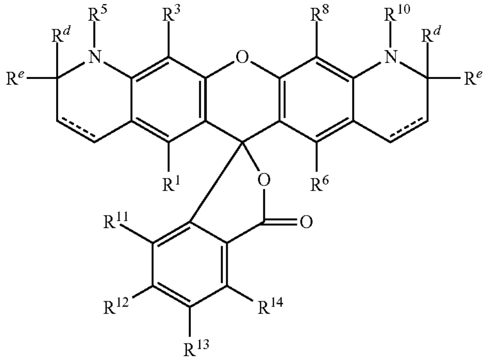

or

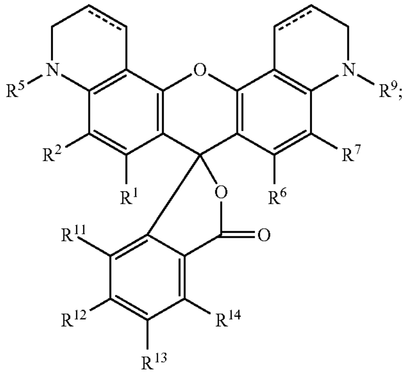

each $R^a$ is independently selected from lower alkyl, (C6-C14) aryl, (C7-C20) arylalkyl, 5-14 membered heteroaryl, —$CX_3$ and 6-20 membered heteroarylalkyl;

each $R^b$ is independently selected from —X, —OH, —$OR^a$, —SH, —$SR^a$—$NH_2$, —$NHR^a$, —$NR^cR^c$, —$N^+R^cR^cR^c$, perhalo lower alkyl, trihalomethyl, trifluoromethyl, —$P(O)(OH)_2$, —$P(O)(OR^a)_2$, $P(O)(OH)(OR^a)$, —$OP(O)(OH)_2$, —$OP(O)(OR^a)_2$, —$OP(O)(OR^a)(OH)$, —$S(O)_2OH$, —$S(O)_2R^a$, —C(O)H, —$C(O)R^a$, —C(S)X, —$C(O)OR^a$, —C(O)OH, —$C(O)NH_2$, —$C(O)NHR^a$, —$C(O)NR^cR^c$, —$C(S)NH_2$, —$C(O)NHR^a$, —$C(O)NR^cR^c$, —$C(NH)NH_2$, —$C(NH)NHR^a$, and —$C(NH)NR^cR^c$;

each $R^c$ is independently an $R^a$, or, alternatively, two $R^c$ bonded to the same nitrogen atom may be taken together with that nitrogen atom to form a 5- to 8-membered saturated or unsaturated ring that may optionally include one or more of the same or different ring heteroatoms, which are typically selected from O, N and S;

each $R^d$ and $R^e$, when taken alone, is independently selected from hydrogen, lower alkyl, (C6-C14) aryl, (C7-C20) arylalkyl, 5-14 membered heteroaryl, 6-20 membered heteroarylalkyl, —$R^b$, or —$(CH_2)_n$—$R^b$—; and n is an integer ranging from 1 to 10.

In another aspect, a reagent useful for labeling an oligonucleotide, which is a compound according to the structural formula:

LM-L-PEP wherein LM represents a label moiety that comprises an N-protected NH-rhodamine moiety, PEP is a phosphate ester precursor group which comprises a phosphoramidite group or an H-phosphonate group, and L is an optional linker linking the label moiety to the phosphate ester precursor group, in which the N-protected NH-rhodamine moiety of the structure (I)

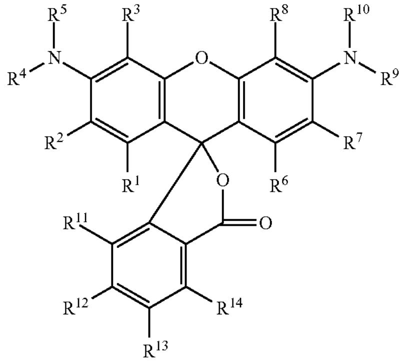

wherein $R^1$, $R^2$, $R^3$, $R^6$, $R^7$, $R^8$, $R^{11}$, $R^{12}$, $R^{13}$, and $R^{14}$, when taken alone, are each independently of one another selected from hydrogen, lower alkyl, (C6-C14) aryl, (C7-C20) arylalkyl, 5-14 membered heteroaryl, 6-20 membered heteroarylalkyl, —$R^b$, or —$(CH_2)_n$—$R^b$, $R^5$ is a protecting group, each of $R^4$, $R^9$, and $R^{10}$, when taken alone, is independently hydrogen, lower alkyl, (C6-C14) aryl, (C7-C20) arylalkyl, 5-14 membered heteroaryl, 6-20 membered heteroarylalkyl, —$P(O)(OH)_2$, —$P(O)(OR^a)_2$, $P(O)(OH)(OR^a)$, —$OP(O)(OH)_2$, —$OP(O)(OR^a)_2$, —$OP(O)(OR^a)(OH)$, —$S(O)_2OH$, —$S(O)_2R^a$, —C(O)H, —$C(O)R^a$, —C(S)X, —$C(O)OR^a$, —C(O)OH, —$C(O)NH_2$, —$C(O)NHR^a$, —$C(O)NR^cR^c$, —$C(S)NH_2$, —$C(O)NHR^a$, —$C(O)NR^cR^c$, —$C(NH)NH_2$, —$C(NH)NHR^a$, and —$C(NH)NR^cR^c$, where X is a halo, alternatively, $R^1$ and $R^2$ and/or $R^6$ and $R^7$ are taken together with the carbon atoms to which they are bonded to form an optionally substituted benzo group, and/or $R^7$ and $R^9$ and/or $R^8$ and $R^{10}$ and/or $R^4$ and one of $R^2$ or $R^3$ are taken together with the carbon atoms to which they are bonded to form an optionally substituted heterocycloalkyl group, an optionally substituted heterocycloalkenyl group, or an optionally substituted heteroaryl group;

wherein n is an integer ranging from 1 to 10;

wherein $R^b$ is independently selected from —X, —OH, —$OR^a$, —SH, —$SR^a$—$NH_2$, —$NHR^a$, —$NR^cR^c$, —$N^+R^cR^cR^c$, perhalo lower alkyl, trihalomethyl, trifluoromethyl, —$P(O)(OH)_2$, —$P(O)(OR^a)_2$, $P(O)(OH)(OR^a)$, —$OP(O)(OH)_2$, —$OP(O)(OR^a)_2$, —$OP(O)(OR^a)(OH)$, —$S(O)_2OH$, —$S(O)_2R^a$, —C(O)H, —$C(O)R^a$, —C(S)X, —$C(O)OR^a$, —C(O)OH, —$C(O)NH_2$, —$C(O)NHR^a$, —$C(O)NR^cR^c$, —$C(S)NH_2$, —$C(O)NHR^a$, —$C(O)NR^cR^c$, —$C(NH)NH_2$, —C(NH)NHR$^a$, and —C(NH)NR$^c$R$^c$, each R$^a$ is, independently of the others, selected from lower alkyl, (C6-C14) aryl, (C7-C20) arylalkyl, 5-14 membered heteroaryl, —$CX_3$ and 6-20 membered heteroarylalkyl, and each R$^c$ is, independently of the others, an R$^a$, or, alternatively, two R$^c$ bonded to the same nitrogen atom may be taken together with that nitrogen atom to form a 5- to 8-membered saturated or unsaturated ring that may optionally include one or more of the same or different ring heteroatoms, which are typically selected from O, N and S; and with the proviso that at least one of $R^2$, $R^3$, $R^7$, $R^8$, $R^{12}$, or $R^{13}$ of the compound of formula LM-L-PEP comprises a group of the formula —Y—, wherein Y is selected from the group consisting of —C(O)—, —$S(O)_2$—, —S— and —NH—.

In another aspect, a method comprises:

co-amplifying a nucleic acid sample with a plurality of amplification primer pairs to form a plurality of amplifications products, wherein at least one of each of the primer pairs comprises a labeled nucleotide having a structural formula LM-L-PEP wherein each of the amplification products comprises a different genetic loci.

3. BRIEF DESCRIPTION OF THE FIGURES

FIG. 1 provides exemplary linkers that can be used to link the various different moieties comprising the reagents described herein to one another;

FIG. 2 provides exemplary embodiments of non-nucleosidic synthesis reagents that do not include synthesis handles;

FIG. 3 provides exemplary embodiments of nucleosidic synthesis reagents that do not include synthesis handles;

FIG. 4 provides exemplary embodiments of non-nucleosidic synthesis reagents that include a synthesis handle;

FIG. 5 provides exemplary embodiments of nucleosidic synthesis reagents that include synthesis handles;

FIG. 6 provides exemplary embodiments of non-nucleosidic solid support reagents;

FIG. 7 provides exemplary embodiments of nucleosidic solid support reagents;

Figure 10:
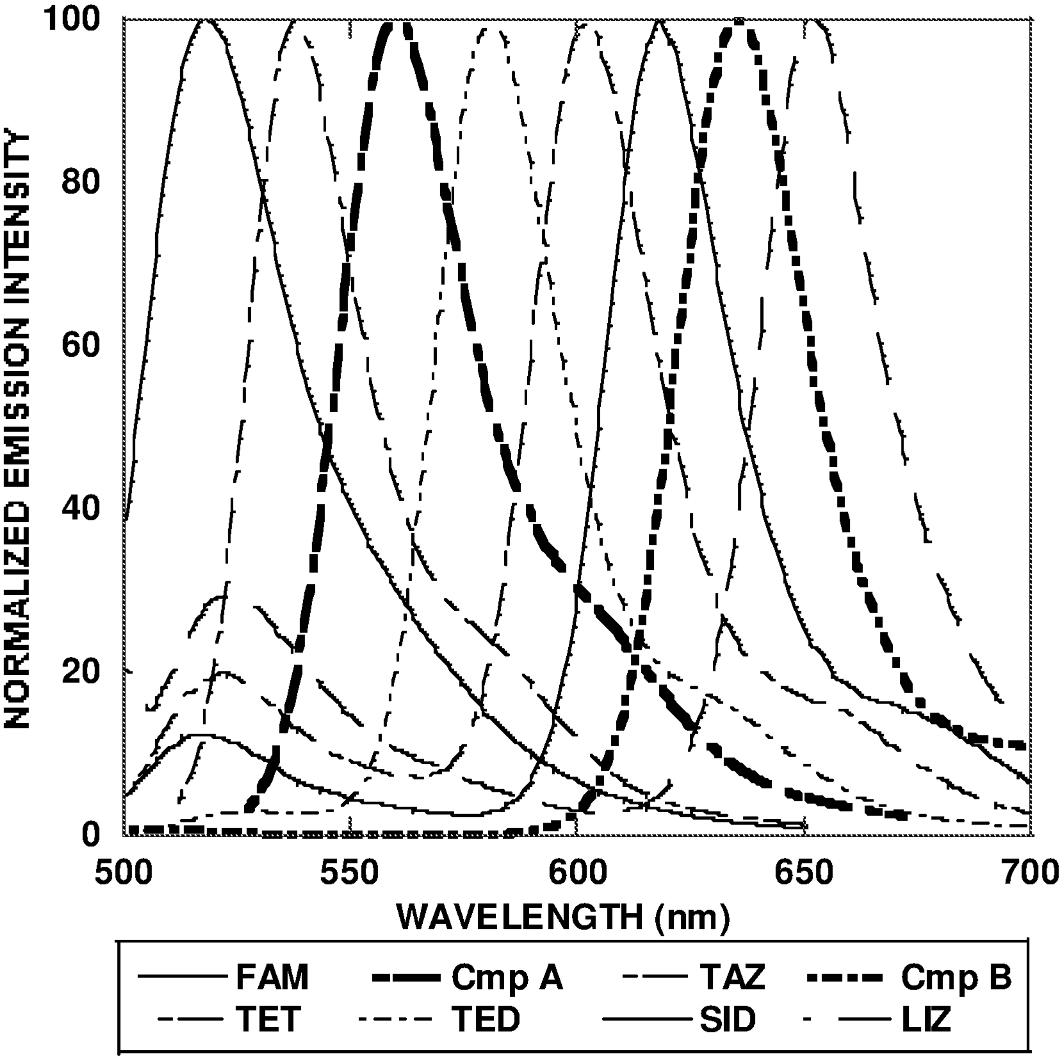

FIG. 10 illustrates the spectra of a proposed dye set for use in multiplex assays. Cmp A, an asymmetric rhodamine as described in PCT/US2019/67925; Cmp B, an asymmetric rhodamine as shown in structure D.1.

4. DETAILED DESCRIPTION

It is to be understood that both the foregoing general description and the following detailed description are exemplary and explanatory only, and are not intended to be restrictive of the compositions and methods described herein. In this disclosure, the use of "or" means "and/or" unless stated otherwise. Similarly, the expressions "comprise," "comprises," "comprising," "include," "includes" and "including" are not intended to be limiting.

As used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As used herein, the terms "including," "containing," and "comprising" are used in their open, non-limiting sense.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

4.1 Definitions

As used herein, the following terms and phrases are intended to have the following meanings:

Alkyl," by itself or as part of another substituent, refers to a saturated or unsaturated branched, straight-chain or cyclic, monovalent hydrocarbon radical having the stated number of carbon atoms (i.e., C1-C6 means one to six carbon atoms) that is derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl," "alkenyl" and/or "alkynyl" is used, as defined below. As used herein, "lower alkyl" means (C1-C8) alkyl.

"Alkanyl," by itself or as part of another substituent, refers to a saturated branched, straight-chain or cyclic alkyl derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like. As used herein, "lower alkanyl" means (C1-C8) alkanyl.

"Alkenyl," by itself or as part of another substituent refers, to an unsaturated branched, straight-chain or cyclic alkyl having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like. As used herein, "lower alkenyl" means (C2-C8) alkenyl.

"Alkynyl," by itself or as part of another substituent, refers to an unsaturated branched, straight-chain or cyclic alkyl having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like. As used herein, "lower alkynyl" means (C2-C8) alkynyl.

"Alkyldiyl," by itself or as part of another substituent, refers to a saturated or unsaturated, branched, straight-chain or cyclic divalent hydrocarbon group having the stated number of carbon atoms (i.e., C1-C6 means from one to six carbon atoms) derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to, methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. Where it is specifically intended that the two valencies are on the same carbon atom, the nomenclature "alkylidene" is used. In some embodiments, the alkyldiyl group is (C1-C8) alkyldiyl. Specific embodiments include saturated acyclic alkanyldiyl groups in which the radical centers are at the terminal carbons, e.g., methandiyl (methano); ethan-1,2-diyl (ethano); propan-1,3-diyl (propano); butan-1,4-diyl (butano); and the like (also referred to as alkylenos, defined infra). As used herein, "lower alkyldiyl" means (C1-C8) alkyldiyl.

"Alkylene," by itself or as part of another substituent, refers to a straight-chain saturated or unsaturated alkyldiyl group having two terminal monovalent radical centers derived by the removal of one hydrogen atom from each of two terminal carbon atoms of straight-chain or branched parent alkane, alkene or alkyne, or by the removal of one hydrogen atom from each of two different ring atoms of a parent cycloalkyl. The locant of a double bond or triple bond, if present, in a particular alkylene is indicated in square brackets. Typical alkylene groups include, but are not limited to, methylene (methano); ethylenes such as ethano, etheno, ethyno; propylenes such as propano, prop[1]eno, propa[1,2]dieno, prop[1]yno, etc.; butylenes such as butano, but[1]eno, but[2]eno, buta[1,3]dieno, but[1]yno, but[2]yno, buta[1,3]diyno, etc.; and the like. Where specific levels of saturation are intended, the nomenclature alkano, alkeno and/or alkyno is used. In some embodiments, the alkylene group is (C1-C8) or (C1-C3) alkylene. Specific embodiments include straight-chain saturated alkano groups, e.g., methano, ethano, propano, butano, and the like. As used herein, "lower alkylene" means (C1-C8) alkylene.

"Heteroalkyl," Heteroalkanyl," Heteroalkenyl," Heteroalkynyl," Heteroalkyldiyl" and "Heteroalkylene," by themselves or as part of another substituent, refer to alkyl, alkanyl, alkenyl, alkynyl, alkyldiyl and alkylene groups, respectively, in which one or more of the carbon atoms are each independently replaced with the same or different heteroatoms or heteroatomic groups. Typical heteroatoms and/or heteroatomic groups which can replace the carbon atoms include, but are not limited to, —O—, —S—, —S—O—, —NR'—, —PH—, —S(O)—, —SO2-, —S(O)NR'—, —SO2NR'—, and the like, including combinations thereof, where R' is hydrogen or a substitutents, such as, for example, (C1-C8) alkyl, (C6-C14) aryl or (C7-C20) arylalkyl.

"Cycloalkyl" and "Heterocycloalkyl," by themselves or as part of another substituent, refer to cyclic versions of "alkyl" and "heteroalkyl" groups, respectively. For heteroalkyl groups, a heteroatom can occupy the position that is attached to the remainder of the molecule. Typical cycloalkyl groups include, but are not limited to, cyclopropyl; cyclobutyls such as cyclobutanyl and cyclobutenyl; cyclopentyls such as cyclopentanyl and cyclopentenyl; cyclohexyls such as cyclohexanyl and cyclohexenyl; and the like. Typical heterocycloalkyl groups include, but are not limited to, tetrahydrofuranyl (e.g., tetrahydrofuran-2-yl, tetrahydrofuran-3-yl, etc.), piperidinyl (e.g., piperidin-1-yl, piperidin-2-yl, etc.), morpholinyl (e.g., morpholin-3-yl, morpholin-4-yl, etc.), piperazinyl (e.g., piperazin-1-yl, piperazin-2-yl, etc.), and the like.

"Parent Aromatic Ring System" refers to an unsaturated cyclic or polycyclic ring system having a conjugated $\pi$ electron system. Specifically included within the definition of "parent aromatic ring system" are fused ring systems in which one or more of the rings are aromatic and one or more of the rings are saturated or unsaturated, such as, for example, fluorene, indane, indene, phenalene, tetrahydronaphthalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, indacene, s-indacene, indane, indene, naphthalene, octacene, octaphene, octalene, ovalene, pentacene, pentalene, pentaphene, perylene, phenalene, phenanthrene, picene, pleiadene, pyrene, pyranthrene, rubicene, tetrahydronaphthalene, triphenylene, trinaphthalene, and the like.

"Aryl," by itself or as part of another substituent, refers to a monovalent aromatic hydrocarbon group having the stated number of carbon atoms (i.e., C6-C14 means from 6 to 14 carbon atoms) derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, pentacene, pentalene, pentaphene, perylene, phenalene, phenanthrene, picene, pleiadene, pyrene, pyranthrene, rubicene, triphenylene, trinaphthalene, and the like, as well as the various hydro isomers thereof. Specific exemplary aryls include phenyl and naphthyl.

"Arylalkyl," by itself or as part of another substituent, refers to an acyclic alkyl group in which one of the hydrogen atoms bonded to a carbon atom, in some embodiments a terminal or sp3 carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where alkyl moieties having a specified degree of saturation are intended, the nomenclature arylalkanyl, arylalkenyl and/or arylalkynyl is used. When a defined number of carbon atoms are stated, for example, (C7-C20) arylalkyl, the number refers to the total number of carbon atoms comprising the arylalkyl group.

"Parent Heteroaromatic Ring System" refers to a parent aromatic ring system in which one or more carbon atoms are each independently replaced with the same or different heteroatoms or heteroatomic groups. Typical heteroatoms or heteroatomic groups to replace the carbon atoms include, but are not limited to, N, NH, P, O, S, S(O), SO2, Si, etc. Specifically included within the definition of "parent heteroaromatic ring systems" are fused ring systems in which one or more of the rings are aromatic and one or more of the rings are saturated or unsaturated, such as, for example, benzodioxan, benzofuran, chromane, chromene, indole, indoline, xanthene, etc. Also included in the definition of "parent heteroaromatic ring system" are those recognized rings that include common substituents, such as, for example, benzopyrone and 1-methyl-1,2,3,4-tetrazole. Typical parent heteroaromatic ring systems include, but are not limited to, acridine, benzimidazole, benzisoxazole, benzodioxan, benzodioxole, benzofuran, benzopyrone, benzothiadiazole, benzothiazole, benzotriazole, benzoxaxine, benzoxazole, benzoxazoline, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Heteroaryl," by itself or as part of another substituent, refers to a monovalent heteroaromatic group having the stated number of ring atoms (e.g., "5-14 membered" means from 5 to 14 ring atoms) derived by the removal of one hydrogen atom from a single atom of a parent heteroaromatic ring system. Typical heteroaryl groups include, but are not limited to, groups derived from acridine, benzimidazole, benzisoxazole, benzodioxan, benzodiaxole, benzofuran, benzopyrone, benzothiadiazole, benzothiazole, benzotriazole, benzoxazine, benzoxazole, benzoxazoline, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like, as well as the various hydro isomers thereof.

"Heteroarylalkyl," by itself or as part of another substituent, refers to an acyclic alkyl group in which one of the hydrogen atoms bonded to a carbon atom, in some embodiments a terminal or sp3 carbon atom, is replaced with a heteroaryl group. Where alkyl moieties having a specified degree of saturation are intended, the nomenclature heteroarylalkanyl, heteroarylalkenyl and/or heteroarylalkynyl is used. When a defined number of atoms are stated, for example, 6-20-membered hetoerarylalkyl, the number refers to the total number of atoms comprising the arylalkyl group.

"Haloalkyl," by itself or as part of another substituent, refers to an alkyl group in which one or more of the hydrogen atoms is replaced with a halogen. Thus, the term "haloalkyl" is meant to include monohaloalkyls, dihaloalkyls, trihaloalkyls, etc. up to perhaloalkyls. For example, the expression "(C1-C2) haloalkyl" includes fluoromethyl, difluoromethyl, trifluoromethyl, 1-fluoroethyl, 1,1-difluoroethyl, 1,2-difluoroethyl, 1,1,1-trifluoroethyl, perfluoroethyl, etc.

The above-defined groups may include prefixes and/or suffixes that are commonly used in the art to create additional well-recognized substituent groups. As non-limiting specific examples, "alkyloxy" and/or "alkoxy" refer to a group of the formula —OR", "alkylamine" refers to a group of the formula —NHR" and "dialkylamine" refers to a group of the formula —NR"R", where each R" is an alkyl.

As used herein, "DNA" refers to deoxyribonucleic acid in its various forms as understood in the art, such as genomic DNA, cDNA, isolated nucleic acid molecules, vector DNA, and chromosomal DNA. "Nucleic acid" refers to DNA or RNA (ribonucleic acid) in any form. As used herein, the term "isolated nucleic acid molecule'1 refers to a nucleic acid molecule (DNA or RNA) that has been removed from its native environment. Some examples of isolated nucleic acid molecules are recombinant DNA molecules contained in a vector, recombinant DNA molecules maintained in a heterologous host cell, partially or substantially purified nucleic acid molecules, and synthetic DNA molecules. An "isolated" nucleic acid can be free of sequences which naturally flank the nucleic acid (i.e., sequences located at the 5' and 3' ends of the nucleic acid) in the genomic DNA of the organism from which the nucleic acid is derived. Moreover, an "isolated" nucleic acid molecule, such as a cDNA molecule, can be substantially free of other cellular material or culture medium when produced by recombinant techniques, or of chemical precursors or other chemicals when chemically synthesized.

"Short tandem repeat" or "STR" loci refer to regions of genomic DNA which contain short, repetitive sequence elements. The sequence elements that are repeated are not limited to but are generally three to seven base pairs in length. Each sequence element is repeated at least once within an STR and is referred to herein as a "repeat unit." The term STR also encompasses a region of genomic DNA wherein more than a single repeat unit is repeated in tandem or with intervening bases, provided that at least one of the sequences is repeated at least two times in tandem.

"Polymorphic short tandem repeat loci" refers to STR loci in which the number of repetitive sequence elements (and net length of the sequence) in a particular region of genomic DNA varies from allele to allele, and from individual to individual.

As used herein, "allelic ladder" refers to a standard size marker consisting of amplified alleles from the locus. "Allele" refers to a genetic variation associated with a segment of DNA; i.e., one of two or more alternate forms of a DNA sequence occupying the same locus.

"Biochemical nomenclature" refers to the standard biochemical nomenclature as used herein, in which the nucleotide bases are designated as adenine (A), thymine (T), guanine (G), and cytosine (C). Corresponding nucleotides are, for example, deoxyguanosine-5'.triphosphate (dGTP).

"DNA polymorphism" refers to the condition in which two or more different nucleotide sequences in a DNA sequence coexist in the same interbreeding population.

"Locus" or "genetic locus" refers to a specific physical position on a chromosome. Alleles of a locus are located at identical sites on homologous chromosomes.

"Locus-specific primer" refers to a primer that specifically hybridizes with a portion of the stated locus or its complementary strand, at least for one allele of the locus, and does not hybridize efficiently with other DNA sequences under the conditions used in the amplification method.

"Polymerase chain reaction" or "PCR" refers to a technique in which repetitive cycles of denaturation, annealing with a primer, and extension with a DNA polymerase enzyme are used to amplify the number of copies of a target DNA sequence by approximately $10^6$ times or more. The PCR process for amplifying nucleic acids is covered by U.S. Pat. Nos. 4,683,195 and 4,683,202, which are herein incorporated in their entirety by reference for a description of the process. The reaction conditions for any PCR comprise the chemical components of the reaction and their concentrations, the temperatures used in the reaction cycles, the number of cycles of the reaction, and the durations of the stages of the reaction cycles.

As used herein, "amplify" refers to the process of enzymatically increasing the amount of a specific nucleotide sequence. This amplification is not limited to but is generally accomplished by PCR. As used herein, "denaturation" refers to the separation of two complementary nucleotide strands from an annealed state. Denaturation can be induced by a number of factors, such as, for example, ionic strength of the buffer, temperature, or chemicals that disrupt base pairing interactions. As used herein, "annealing" refers to the specific interaction between strands of nucleotides wherein the strands bind to one another substantially based on complementarity between the strands as determined by Watson-Crick base pairing. It is not necessary that complementarity be 100% for annealing to occur. As used herein, "extension" refers to the amplification cycle after the prim.er oligonucleotide and target nucleic acid have annealed, wherein the polymerase enzyme effects primer extension into the appropriately-sized fragments using the target nucleic acid as replicative template.

"Primer" refers to a single-stranded oligonucleotide or DNA fragment which hybridizes with a DNA strand of a locus in such a manner that the 3' terminus of the primer can act as a site of polymerization and extension using a DNA polymerase enzyme. "Primer pair" refers to two primers comprising a primer 1 that hybridizes to a single strand at one end of the DNA sequence to be amplified, and a primer 2 that hybridizes with the other end on the complementary strand of the DNA sequence to be amplified. "Primer site" refers to the area of the target DNA to which a primer hybridizes.

"Genetic markers" are generally alleles of genomic DNA with characteristics of interest for analysis, such as DNA typing, in which individuals are differentiated based on variations in their DNA. Most DNA typing methods are designed to detect and analyze differences in the length and/or sequence of one or more regions of DNA markers known to appear in at least two different forms, or alleles, in a population. Such variation is referred to as "polymorphism," and any region of DNA in which such a variation occurs is referred to as a "polymorphic locus." One possible method of performing DNA typing involves the joining of PCR amplification technology (KB Mullis, U.S. Pat. No. 4,683,202) with the analysis of length variation polymorphisms. PCR traditionally could only be used to amplify relatively small DNA segments reliably; i.e., only amplifying DNA segments under 3,000 bases in length (M. Ponce and L. Micol (1992), NAR 20(3):623; R. Decorte et al. (1990), DNA CELL BIOL 9(6):461 469). Short tandem repeats (STRs), minisatellites and variable number of tandem repeats (VNTRs) are some examples of length variation polymorphisms. DNA segments containing minisatellites or VNTRs are generally too long to be amplified reliably by PCR. By contrast STRs, containing repeat units of approximately three to seven nucleotides, are short enough to be useful as genetic markers in PCR applications, because amplification protocols can be designed to produce smaller products than are possible from the other variable length regions of DNA.

As used herein, the term "kit" refers to any delivery system for delivering materials. In the context of reaction assays, such delivery systems include systems that allow for the storage, transport, or delivery of reaction reagents (e.g., oligonucleotides, enzymes, primer set(s), etc. in the appropriate containers) and/or supporting materials (e.g., buffers, written instructions for performing the assay etc.) from one location to another. For example, kits can include one or more enclosures (e.g., boxes) containing the relevant reaction reagents and/or supporting materials. As used herein, the term "fragmented kit" refers to a delivery system comprising two or more separate containers that each contains a subportion of the total kit components. The containers may be delivered to the intended recipient together or separately. For example, a first container may contain an enzyme for use in an assay, while a second container contains oligonucleosides. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

4.2 Exemplary Embodiments

The present disclosure provides reagents that can be used to chemically synthesize oligonucleotides bearing label moieties that comprise rhodamine dyes. Traditionally, it has been difficult to chemically synthesize rhodamine-labeled oligonucleotides owing, in part, to the lack of availability of rhodamine-containing synthesis reagents that are stable to the synthesis and/or deprotection conditions commonly employed in the step-wise chemical synthesis of oligonucleotides. It has now been discovered that protecting the exocyclic amine groups of NH-rhodamine dyes with base-labile protecting groups, such as acetyl groups, provides N-protected NH-rhodamine dyes that are stable to the chemical synthesis and deprotection conditions commonly employed in the solid-phase synthesis of oligonucleotides. As a consequence, the N-protected NH-rhodamines can be incorporated into reagents that can be used to synthesize oligonucleotides labeled with label moieties that comprise rhodamine dyes, thereby obviating the need to attach the labels post-synthesis. Because the labels are attached during synthesis, the resultant labeled oligonucleotide can be purified for use without the use of HPLC.

The reagents take advantage of various features of reagents and chemistries that are well-known for the step-wise solid phase synthesis of oligonucleotides, and can be in the form of synthesis reagents that are coupled to a hydroxyl group during the step-wise solid phase synthesis of an oligonucleotide chain, or in the form of solid support reagents to which nucleoside monomer reagents, such as nucleoside phosphoramidite reagents, and/or optionally other reagents, are coupled in a step-wise fashion to yield a synthetic oligonucleotide.

The synthesis and solid support reagents can be nucleosidic in nature in that they can include a nucleoside moiety, or they can be non-nucleosidic in nature.

All of the reagents described herein include a label moiety that comprises an N-protected NH-rhodamine dye or moiety. The N-protected NH-rhodamine dye can be the only dye comprising the label moiety or, alternatively, it can be one of two or more dyes comprising a larger dye network. The solid support reagents additionally include a solid support and one or more synthesis handles to which additional groups can be coupled. The synthesis reagents additionally include a PEP group useful for coupling the reagent to a primary hydroxyl group, and may optionally include one or more synthesis handles. The various moieties and groups comprising the reagents can be linked together in any fashion and/or orientation that permits them to carry out their respective functions. They can be linked to one another through linking groups included on the moieties, or they can be linked to one another with the aid of linkers.

The various moieties, groups and linkers comprising the reagents described herein are described in more detail below.

4.3 Linkers and Linking Groups

The various groups and moieties comprising the reagents described herein are typically connected to one another with linkers. The identity of any particular linker will depend, in part, upon the identities of the moieties being linked to one another. In general, the linkers include a spacing moiety that can comprise virtually any combination of atoms or functional groups stable to the synthetic conditions used for the synthesis of labeled oligonucleotides, such as the conditions commonly used to synthesize oligonucleotides by the phosphite triester method, and can be linear, branched, or cyclic in structure, or can include combinations of linear, branched and/or cyclic structures. The spacing moiety can be monomeric in nature, or it can be or include regions that are polymeric in nature. The spacing moiety can be designed to have specified properties, such as the ability to be cleaved under specified conditions, or specified degrees of rigidity, flexibility, hydrophobicity and/or hydrophilicity.

As will be described in more detail below, many embodiments of the reagents described herein are synthesized by condensing synthons to one another in specified fashions to yield the desired reagents. Each synthon typically includes one or more linking groups suitable for forming the desired linkages. Generally, the linking group comprises a functional group $F^y$ that is capable of reacting with, or that is capable of being activated so as to be able to react with, another functional group $F^z$ to yield a covalent linkage Y—Z, where Y represents the portion of the linkage contributed by $F^y$ and Z the portion contributed by $F^z$. Such groups $F^y$ and $F^z$ are referred to herein as "complementary functional groups."

Pairs of complementary functional groups capable of forming covalent linkages with one another are well-known in the art. In some embodiments, one of $F^y$ or $F^z$ comprises a nucleophilic group and the other one of $F^y$ or $F^z$ comprises an electrophilic group. Complementary nucleophilic and electrophilic groups useful for forming linkages (or precursors thereof that are or that can be suitably activated so as to form linkages) that are stable to a variety of synthesis and other conditions are well-known in the art. Examples of suitable complementary nucleophilic and electrophilic groups that can be used to effect linkages in the various reagents described herein, as well as the resultant linkages formed therefrom, are provided in Table 1, below:

TABLE 1

| Electrophilic Group | Nucleophilic Group | Resultant Covalent Linkage |
|---|---|---|
| activated esters* | amines/anilines | caboxamides |
| acyl azides** | amines/anilines | caboxamides |
| acyl halides | amines/anilines | caboxamides |
| acyl halides | alchohol/phenols | esters |
| acyl nitrites | alchohol/phenols | esters |
| acyl nitrites | amines/anilines | caboxamides |
| aldehydes | amines/anilines | imines |
| aldehydes or ketones | hydrazines | hydrazines |
| aldehydes or ketones | hydroxylamines | oximes |
| Alkyl halides | amines/anilines | alkyl amines |
| Alkyl halides | carboxylic acids | esters |
| Alkyl halides | thiols | thioethers |
| Alkyl halides | alchohol/phenols | esters |
| Alkyl sulfonates | thiols | thioethers |
| Alkyl sulfonates | carboxylic acids | esters |
| Alkyl sulfonates | alchohol/phenols | esters |
| anhydrides | alchohol/phenols | esters |
| anhydrides | amines/anilines | caboxamides |
| aryl halides | thiols | thiophenols |
| aryl halides | amines | aryl amines |
| aziridines | thiols | thioethers |
| boronates | glycols | boronate esters |
| carboxylic acids | amines/anilines | caboxamides |
| carboxylic acids | alcohols | esters |
| carboxylic acids | hydrazines | hydrazides |
| carbodiimides | carboxylic acids | N-acylureas or anhydrides |
| diazoalkanes | carboxylic acids | esters |
| epoxides | thiols | thioethers |
| haloacetamides | thiols | thioethers |
| halotriazines | amines/anilines | aminotriazines |
| halotriazines | alchohol/phenols | triazinyl ethers |
| imido esters | amines/anilines | amidines |
| isocyanates | amines/anilines | ureas |
| isocyanates | alchohol/phenols | urethanes |

Figure 2:
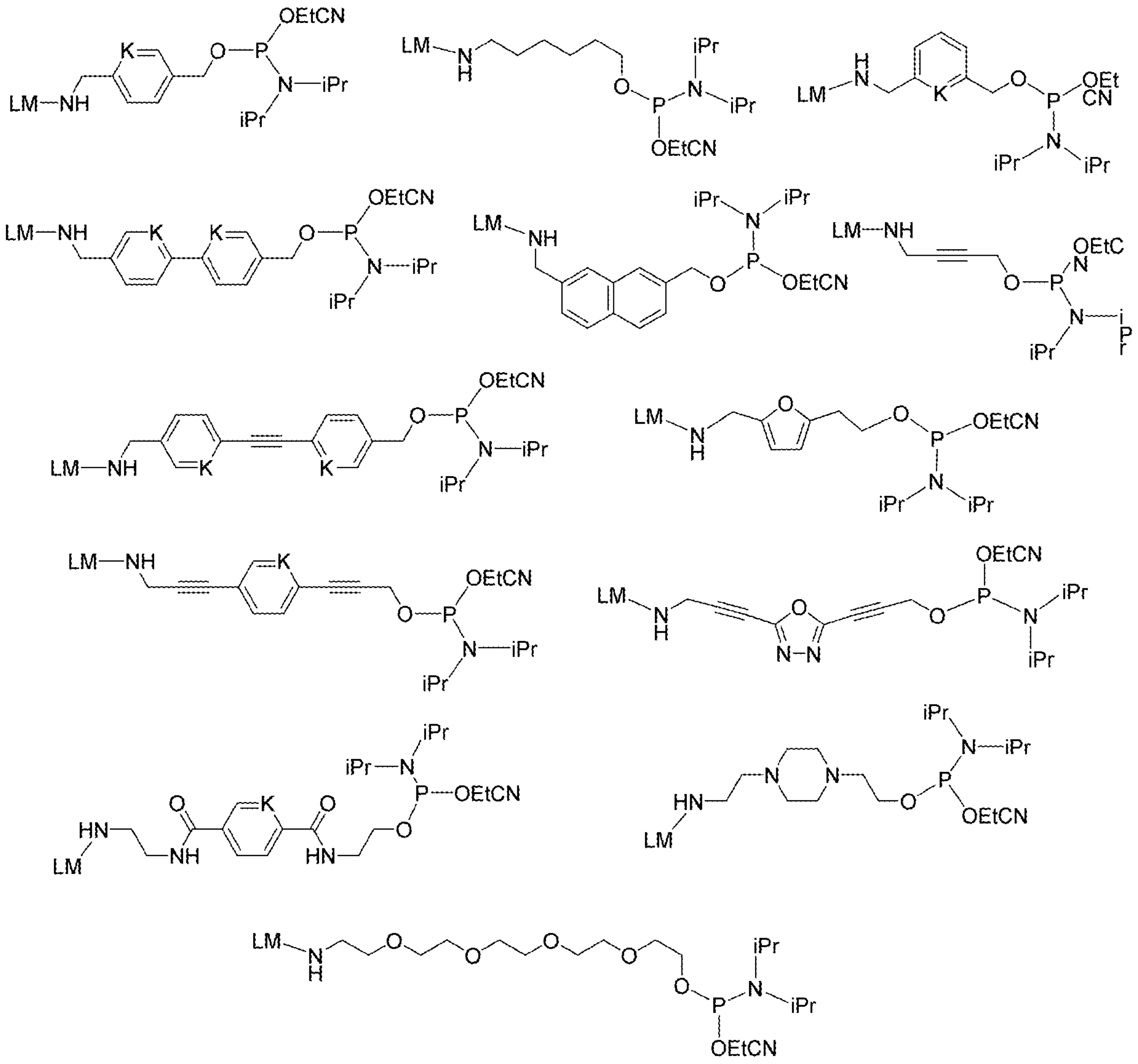

Thus, linker synthons can generally be described by the formula LG-Sp-LG, where each LG represents, independently of the other, a linking group, and Sp represents the spacing moiety. In some embodiments, linker synthons can be described by the formula $F^z$-Sp-$F^z$, where each $F^z$ represents, independently of the other, one member of a pair of complementary nucleophilic or electrophilic functional groups as described above. In specific embodiments, each $F^z$ is, independently of the other, selected from the groups listed in Table 1, supra. Linker synthons of this type form linker moieties of the formula —Z-Sp-Z—, where each Z represents, independently of the other, a portion of a linkage as described above. Specific linkers suitable for linking specified groups and moieties to one another in the reagents described herein will be discussed in more detail in connection with exemplary embodiments of the reagents. Non-limiting exemplary embodiments of linkers that can be used to link the various groups and moieties comprising the reagents described herein to one another are illustrated in FIG. 2. In FIG. 2, $Z^1$ and $Z^2$ each represent, independently of one another, a portion of a linkage contributed by a functional group $F^z$, as previously described, and K is selected from —CH— and —N—. In some specific embodiments of the linkers illustrated in FIG. 2, one of $Z^1$ or $Z^2$ is —NH— and the other is selected from —O—, —C(O)— and —$S(O)_2$—.

4.4 Label Moiety

The reagents described herein can include a label moiety that comprises an NH-rhodamine dye that is protected at one of the exocyclic amine groups with a protecting group having specified properties. Generally, rhodamine dyes are characterized by four main features: (1) a parent Xanthene ring; (2) an exocyclic amine substituent; (3) an exocyclic imminium substituent; and (4) a phenyl group substituted at the ortho position with a carboxyl group. In some embodiments, the NH-rhodamine dye of the disclosure can be generally described by the formula (Ia). In some embodiments, the exocyclic amine and/or imminium groups are typically positioned at the C3' and C6' carbon atoms of the parent Xanthene ring, although "extended" rhodamines in which the parent xanthene ring comprises a benzo group fused to the C3' and C4' carbons and/or the C5' and C6' carbons are also known. In these extended rhodamines, the characteristic exocyclic amine and imminium groups are positioned at the corresponding positions of the extended Xanthene ring.

The carboxyl-substituted phenyl group is attached to the C1 carbon of the parent Xanthene ring. As a consequence of the ortho carboxyl substituent, rhodamine dyes can exist in two different forms: (1) the open, acid form; and (2) the closed, lactone form. While not intending to be bound by any theory of operation, because NMR spectra of exemplary N-protected NH-rhodamine dyes described herein are consistent with the closed spiro lactone form of the dye, it is believed that the N-protected NH-rhodamine dyes comprising the label moiety of the reagents described herein are in the closed, spiro lactone form. Thus, the various rhodamines, as well as their unprotected counterparts, are illustrated herein in their closed, spirolactone form. However, it is to be noted that this is for convenience only and is not intended to limit the various reagents described herein to the lactone form of the dyes. In certain embodiments, the open, acid form of the compound is fluorescent (or exhibits an increase in fluorescence) relative to the closed, spirolactone form of the compound. The amine groups of the compounds described herein are protectable in the closed, spirolactone form and can be made into and used as phosphoramidites for high yield and high purity labeling of nucleic acids. Thus, also provided herein are fluorescently-labeled nucleic acid probes and primers that include compounds in deprotected, open lactone form. Representative examples of the open lactone form after deprotection of the amine groups and cleavage of the nucleic acid probe from a solid support are shown in FIGS. 8 and 9.

In the closed, spiro lactone form, the A and C rings of the parent xanthene ring are aromatic, and both the C3' and C6' substituents are amines. The exocyclic amine groups of the rhodamine dyes included in the label moieties described herein are either unsubstituted or mono-substituted such that these amine groups are primary or secondary amines. Such rhodamine dyes are referred to herein as "NH-rhodamines." Thus, as used herein, an "NH-rhodamine' generally comprises the following parent NH-rhodamine ring structure:

(Ia)

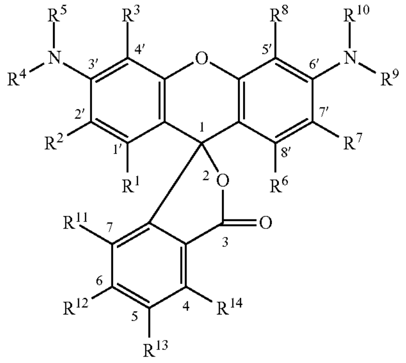

wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$, and $R^{14}$ are as defined herein. In the parent NH-rhodamine ring depicted above, the various carbon atoms are numbered using an arbitrary numbering convention adopted from a numbering convention commonly used for the closed, spiro lactone form of rhodamine dyes. This numbering system is being used for convenience only, and is not intended to be limiting in any way.

In any of the embodiments described herein, exemplary label moieties can be of the formula (II.1), (II.2), (II.3), (II.4)

(II.1)

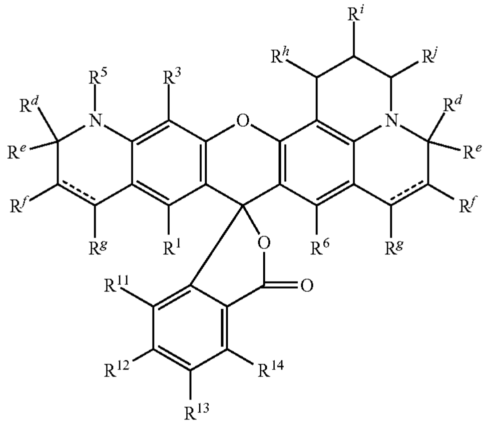

(II.2)

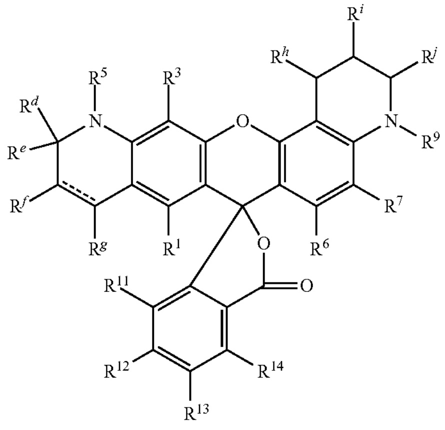

-continued (II.3)

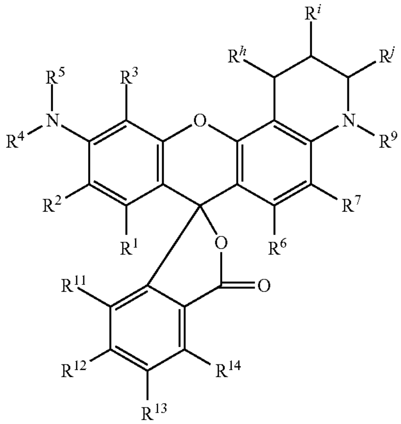

(II.4)

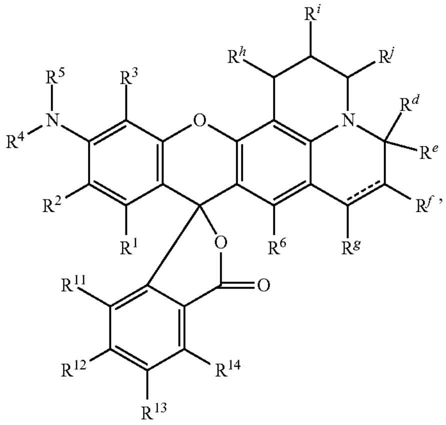

and the like.

One of skill in the art will readily appreciate that the present disclosure describes other label moieties within the formula I, such as those of the formula (II.1), (II.2), and (II.3), wherein the optional double bond between $R^f$ and $R^g$ is alternatively between $R^e$ and $R^f$. Further one of skill in the art will readily appreciate that an additional $R^d$ group can be present on each of $R^e$ and $R^f$, when the double bond between $R^e$ and $R^f$ is not present, or the additional groups on $R^e$ and $R^f$ are H. Additionally, one of skill in the art will appreciate that further embodiments wherein an optional double bond between $R^h$ and $R^i$ or $R^i$ and $R^j$ can be present.

In the NH-rhodamines rings of structural formula (Ia) and other formulas described herein, $R^5$ represents hydrogen or substituent groups substituting the exocyclic amine to which $R^5$ is attached. In some embodiments, $R^5$ can be substituted or unsubstituted alkylaryl or arylalkyl group. In some embodiments, $R^5$ can be a protecting group.

In some embodiments, $R^4$, $R^9$, and/or $R^{10}$ can comprise a substituent that is bridged to an adjacent carbon atom such that the illustrated nitrogen atom is included in a ring that contains 5- or 6-ring atoms. The ring may be saturated or unsaturated, and one or more of the ring atoms can be substituted. When the ring atom(s) are substituted, the substituents are typically, independently of one another, selected from lower alkyl, C6-C14 aryl and C7-C20 arylalkyl groups.

Alternatively, two adjacent ring atoms may be included in an aryl bridge, such as a benzo or naphtho group. Non-limiting exemplary embodiments of rhodamine dyes that include a parent NH-rhodamine ring according to structural formula (Ia) in which the $R^4$, $R^9$, and/or $R^{10}$ group is hydrogen or lower alkyl groups or are included in optionally substituted rings with adjacent carbon atoms. One or more of the carbon atoms at positions C1, C4, C5, C6, C7, C1', C2', C4', C5' C7', and C8' of the parent NH rhodamine rings according to structural formula (Ia) can be, independently of one another, unsubstituted or substituted with substituent groups as defined herein. And, groups useful for substituting rhodamine dyes at these positions are well known in the art, and are described, for example, in U.S. Pat. No. 4,622,400. U.S. Pat. Nos. 5,750,409, 5,847,162, 6,017,712, 6,080,852, 6,184,379 and 6,248,884, the disclosures of which are incorporated herein by reference.

In some embodiments, the substituent groups are, independently of one another, selected from lower alkyl, (C6-C14) aryl, (C7-C20) arylalkyl, 5-14 membered heteroaryl, 6-20 membered heteroarylalkyl, $R^b$ and $—(CH_2)_xR^b$, where x is an integer ranging from 1 to 10 and $R^b$ is independently selected from —X, —OH, $—OR^a$, —SH, $—SR^a—NH_2$, $—NHR^a$, $—NR^cR^c$, $—N^+R^cR^cR^c$, perhalo lower alkyl, trihalomethyl, trifluoromethyl, $—P(O)(OH)_2$, $—P(O)(OR^a)_2$, $P(O)(OH)(OR^a)$, $—OP(O)(OH)_2$, $—OP(O)(OR^a)_2$, $—OP(O)(OR^a)(OH)$, $—S(O)_2OH$, $—S(O)_2R^a$, —C(O)H, $—C(O)R^a$, —C(S)X, $—C(O)OR^a$, —C(O)OH, $—C(O)NH_2$, $—C(O)NHR^a$, $—C(O)NR^cR^c$, $—C(S)NH_2$, $—C(O)NHR^a$, $—C(O)NR^cR^c$, $—C(NH)NH_2$, $—C(NH)NHR^a$, and $—C(NH)NR^cR^c$, wherein X is a halo (preferably fluoro or chloro), each $R^a$ is, independently of the others, selected from lower alkyl, (C6-C14) aryl, (C7-C20) arylalkyl, 5-14 membered heteroaryl and 6-20 membered heteroarylalkyl, and each $R^c$ is, independently of the others, an $R^a$, or, alternatively, two $R^c$ bonded to the same nitrogen atom may be taken together with that nitrogen atom to form a 5- to 8-membered saturated or unsaturated ring that may optionally include one or more of the same or different ring heteroatoms, which are typically selected from O, N and S. Alternatively, the C1' and C2' substituents, and/or the C7' and C8' substituents can be taken together to form substituted or unsubstituted aryl bridges. Such as benzo bridges, with the proviso that the C1' and C2' substituents, and C7' and C8' substituents are not simultaneously included in an aryl bridge. In some embodiment, the groups used to substitute the C1, C4, C5, C6, C7, C1', C2', C4', C5', C7', and C8' carbons do not promote quenching of the rhodamine dye, although in some embodiments quenching substituents may be desirable. Substituents capable of quenching rhodamine dyes include carbonyl, carboxylate, heavy metals, nitro, bromo and iodo. The carbon atoms at positions C4, C5, C6 and C7 of the parent NH-rhodamine rings of structural formula (Ia) can also, independently of one another, include optional substituents. These substituents can be selected from the various substituents described above. In some embodiments, the carbon atoms at positions C4 and C7 are substituted with chloro groups such that the parent NH-rhodamine dye is an NH-4,7-dichlororhodamine dye. A vast number of rhodamine dyes that include parent NH rhodamine rings according to structural formula (Ia) that can be included in the label moiety of the reagents described herein are known in the art, and are described, for example, in U.S. Pat. Nos. 6,248,884; 6,111,116; 6,080,852; 6,051,719, 6,025,505; 6,017,712; 5,936,087; 5,847,162; 5,840,999; 5,750,409: U.S. Pat. Nos. 5,366,860; 5,231,191; 5,227,487; WO97/36960; WO99/27020; Lee et al., 1992, Nucl. Acids Res. 20:2471-2483; Arden-Jacob, "Neue Lanwellige Xanthen Farbstoffe für FluoreszenZSonden und Farbstoff Lauer, Springer-Verlag, Germany, 1993; Sauer et al., 1995, Fluorescence 5:247-261; Lee et al., 1997, Nucl. Acids Res.

25:2816 2822; and Rosenblum et al., 1997, Nucl. Acids Res. 25:4500 4504, the disclosures of which are incorporated herein by reference. Any of the dyes described in these references in which the exocyclic amines are primary or secondary amines as described herein, or 4,7-dichloro analogues of such NH rhodamine dyes, can be included in the label moiety of the reagents described herein.

Because the reagents described herein will be used to chemically synthesize labeled oligonucleotides, $R^5$ can be a protecting group that is stable to the organic synthesis conditions used to synthesize oligonucleotides. As mentioned above, $R^5$ can be a protecting that protects the amine in the form of an amide, for example, a carboxamide, a sulfonamide or a phosphoramide, can be selected as protecting the exocyclic amine in this manner, and is believed to "lock" the protected NH-rhodamine in the closed, lactone, form, contributing to the stability of the reagents described herein. Although not required, it can be convenient to utilize an $R^5$ protecting group that is labile under the conditions used to remove the groups protecting the exocyclic amines of a nucleobase of the synthetic oligonucleotide, so that the protecting group can be removed in a single step.

The conditions used to synthesize and deprotection of synthetic oligonucleotides are well-known in the art, and are described, for example, in Current Protocols in Nucleic Acid Chemistry, Vol. I, Beancage et al., Eds. John Wiley & Sons, 2002, the disclosure of which are incorporated herein by reference. Briefly, synthesis methods that employ phosphoramidite reagents involve multiple rounds of: (i) DMT deprotection to reveal a free hydroxyl, which can be effected by treatment with 2.5% or 3% di- or tri-chloroacetic acid in dichloromethane; (ii) coupling of nucleoside or other phosphoramidite reagents to the free hydroxyl, which can be carried out in acetonitrile containing 0.45 M or 0.5 M tetrazole; (iii) oxidation, which can be carried out by treatment with $I_2$/2,6-lutidine/H2O, and capping, which can be carried out by treatment with 6.5% acetic anhydride in tetrahydrofuran (THF) followed by treatment with 10% 1-methylimidazole (MI) in THF.

Other conditions for carrying out the various steps in the synthesis are also known in the art. For example, phosphoramidite coupling can be carried out in acetonitrile containing 0.25 M 5-ethylthio-1H-tetrazole, 0.25 M 4,5-dicyanoimidazole (DCI) or 0.25 M 5-benzylthio-1H-tetrazole (BTT). Oxidation can be carried out in 0.1 M, 0.05 M or 0.02 M $I_2$, in THF/$H_2O$/pyridine (7:2:1). Capping can be carried out by treatment with THF/lutidine/acetic anhydride followed by treatment with 16% NMI in THF: by treatment with 6.5% DMAP in THF followed by treatment with 10% Melm in THF; or by treatment with 10% Melm in THF followed by treatment with 16% Melm in THF.

Removing any protecting groups and cleavage from the synthesis reagent can typically be effected by treatment with concentrated ammonium hydroxide at 60° C. for 1-12 hr., although nucleoside phosphoramidite reagents protected with groups that can be removed under milder conditions, such as by treatment with concentrated ammonium hydroxide at room temperature for 4-17 hrs or treatment with 0.05 M potassium carbonate in methanol, or treatment with 25% t-butylamine in HO/EtOH, are also known in the art. Skilled artisans will be readily able to select protecting groups having properties suitable for use under specific synthesis and deprotection and/or cleavage conditions. A wide variety of amine protecting groups are taught, for example in, Greene & Wuts, "Protective Groups In Organic Chemistry." 3d Edition, John Wiley & Sons, 1999 (hereinafter "Green & Wuts") at for example, pages 309-405. Skilled artisans can readily select protecting groups $R^5$ or $R^{10}$ having suitable properties from amongst those taught in Green & Wuts. In some embodiments, the protecting groups $R^5$ or $R^{10}$ are acyl groups of the formula —C(O)$R^{15}$, where $R^{15}$ is selected from hydrogen, lower alkyl, methyl, —$CX_3$. —$CHX_2$. —$CH_2X$, —CH, $O_d$ and phenyl optionally mono-substituted with a lower alkyl, methyl, X, $OR^d$, cyano or nitro group, where R" is selected from lower alkyl, phenyl and pyridyl, and each X is a halo group, typically fluoro, or chloro. In some embodiments, $R^{15}$ is methyl. In some embodiments, $R^{15}$ is trifluoromethyl. Acyl protecting groups such as those defined by —C(O)$R^{15}$ can be removed under a variety of basic conditions, including the mild conditions used to remove protecting groups from oligos synthesized with "base labile' phosphoramidite reagents, as are well-known in the art. In some embodiments, $R^5$ is —C(O)$R^{15}$ wherein $R^{15}$ is selected from the group consisting of hydrogen, a lower alkyl, —$CX_3$, —$CHX_2$, —$CH_2X$, —$CH_2$—$OR^d$, and phenyl optionally mono-substituted with a lower alkyl, —X, —$OR^d$, cyano or nitro group, wherein $R^d$ is selected from the group consisting of a lower alkyl, phenyl and pyridyl, and each X is a halo group. Exemplary conditions that can be used are specified above. As will be described in more detail in later sections, the N-protected NH-rhodamine moiety comprising the label moiety may be linked to other groups or moieties. For example, the N-protected NH-rhodamine may be linked to another dye comprising the label moiety, to a PEP group, to a linker, to a synthesis handle, to a quenching moiety, to a moiety that functions to stabilize base-pairing interactions (such as, for example an intercalating dye or a minor-groove-binding molecule), or to other moieties. Such linkages are typically effected via linking groups LG (described above in connection with the linkers) attached to the N-protected NH-rhodamine synthons used to synthesize the reagents.

The linking group LG can be attached to any available carbon atom of the N-protected NH-rhodamine synthon, or to a Substituent group attached to one of these carbon atoms. The positions of the linking groups may depend, in part, on the group or moiety to which the N-protected NH-rhodamine synthon will be attached. In some embodiments, the linking group is attached at the C1', C2', C4', C5', C7', C8', C5, C6, or C7 position of the N-protected NH-rhodamine synthon. In a specific embodiment, the linking group is attached at the C4', C5'. C5 or C6 position.

The N-protected NH-rhodamine synthon can include a single linking group LG, or it can include more than one linking group LG. In embodiments that employ more than one linking group, the linking groups may be the same, or they may be different. N-protected NH-rhodamine synthons that include multiple linking groups LG that are different from one another can have different groups or moieties attached to different positions of the parent NH-rhodamine ring using orthogonal chemistries. The identity of a linking group may, in some instances, depend upon its location on the parent NH-rhodamine ring. In some embodiments in which the linking group LG is attached at the C4'- or C5'-position of the parent NH-rhodamine ring, the linking group LG is a group of the formula —$(CH)_n$—$F^y$, where n is an integer ranging from 0 to 10 and $F^y$ is as described herein. In some embodiments, n is 1 and $F^y$ is —NH.

In some embodiments in which the linking group LG is attached at the 5- or 6-position of the parent NH-rhodamine ring, the linking group LG is a group of the formula —$(CH_2)_n$, —C(O)$OR^f$, where $R^f$ is selected from hydrogen and a good leaving group and n is as previously defined. In some specific embodiments, the linking group LG comprises an NHS ester. In some specific embodiments, n is 0 and $R^f$ is NHS.

As discussed previously, the label moiety can comprise one or more additional dyes such that the N-protected NH-rhodamine, once deprotected, is a member of a larger, energy transfer dye network. Such energy transfer dye networks are well-known in the art, and include combinations of fluorescent dyes whose spectral properties are matched, and/or whose relative distances to one another are adjusted, so that one fluorescent dye in the network, when excited by incident irradiation of an appropriate wavelength, transfers its excitation energy to another fluorescent dyes in the network, which then transfers its excitation energy to yet another fluorescent dye in the network, and so forth, resulting in fluorescence by the ultimate acceptor dye in the network. Dye networks provide label moieties having long Stoke's shifts. In such networks, fluorophores that transfer, or donate, their excitation energy to another fluorophore in the network are referred to as "donors." Fluorophores that receive, or accept, excitation energy from another fluorophore are referred to as "acceptors." In dye networks containing only two fluorescent dyes, one acts as the donor and the other as the acceptor. In dye networks containing three or more fluorescent dyes, at least one dye acts as both a donor and acceptor. The principles of how dye networks work, as well as the criteria for selecting and linking individual dyes suitable for creating such networks are well known, and are described, for example, in Hung et al., 1997, Anal. Biochem. 252:78-88.

In the label moieties described herein that comprise dye networks, the N-protected NH-rhodamine dye, once deprotected, may act as a donor or an acceptor, or as both a donor and acceptor, depending upon the identities of the other dyes comprising the network and the desired incident and fluorescent wavelengths. Numerous dyes suitable for use as donors and/or acceptors for NH-rhodamine dyes are known in the art, and include by way of example and not limitation, xanthene dyes (such as, for example, fluorescein, rhodamine and rhodol dyes), pyrene dyes, coumarin dyes (for example, hydroxy- and amino-coumarins), cyanine dyes, phthalocyanine dyes and lanthenide complexes. Specific, non-limiting examples of these dyes in the context of energy transfer dye networks are described in Hung et al., 1996, Anal. Biochem. 238:165-170; Medintz et al., 2004, Proc. Nat'l Acad. Sci. USA 101(26):9612-9617; U.S. Pat. No. 5,800,996; Sudhaker et al., 2003, Nucleosides, Nucleotides & Nucleic Acids 22:1443-1445; U.S. Pat. No. 6,358,684; Majumdar et al., 2005, J. Mol. Biol. 351:1123-1145; Dietrich et al., 2002, Reviews Mol. Biotechnology. 82(3):211-231; Tsuji et al., 2001, Biophysical J. 81(1):501-515; Dickson et al., 1995, J. Photochemistry & Photobiology 27(1):3-19; and Kumar et al., 2004, Developments in Nucl. Acid Res. 1:251-274, the disclosures of which are incorporated herein by references. Any of these dyes that can be suitably protected in accordance with the principles described herein can be used as donor and acceptor dyes in label moieties that comprise dye networks. In some embodiments, one or more of the donor and/or acceptor dyes comprising the network can be an N-protected NH-rhodamine dye as described herein. Specific positions for attaching donor and/or acceptor dyes to rhodamine dyes to form dye networks, as well as specific linkages and linkers useful for attaching such dyes, are well-known in the art. Specific examples are described, for example, in U.S. Pat. Nos. 6,811,979; 6,008,379; 5,945,526; 5,863,727; and 5,800,996, the disclosures of which are incorporated herein by reference.

In some embodiments, the linker linking the donor and acceptor dyes is an anionic linker as described in U.S. Pat. No. 6,811,979, the disclosure of which is incorporated herein by reference (see, e.g., the disclosure at Col. 17, line 25 through Col. 18, line 37 and FIGS. 1-17).

In some embodiments of the reagents described herein, the label moiety includes a donor dye for the NH-rhodamine dye. In some embodiments, the donor dye is a fluorescein or rhodamine dye, such as, for example, one of the NH-rhodamine dyes described herein. In a specific embodiment, the donor dye is a fluorescein dye. Fluorescein dyes are similar in structure to rhodamine dyes, with the exception that the 3- and 6-positions of the parent xanthene ring (corresponding to the 3'- and 6'-positions of the NH-rhodamine rings of structural formula (Ia)), are substituted with a hydroxyl groups. Like the rhodamines, the fluoresceins can also have extended ring structures in which the carbon atoms at positions C3' and C4' and/or C5' and C6' of the parent xanthene ring are included in aryl bridges such as benzo groups. Thus, the fluoresceins generally include compounds according to structural formulae (IVa), (IVb) and (IVc), below:

(IVa)

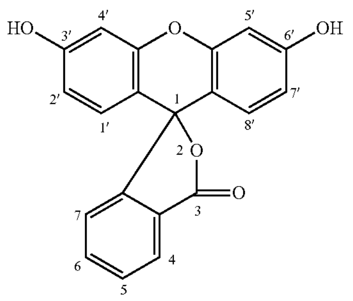

(IVb)

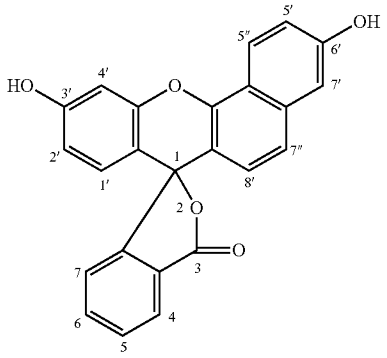

(IVc)

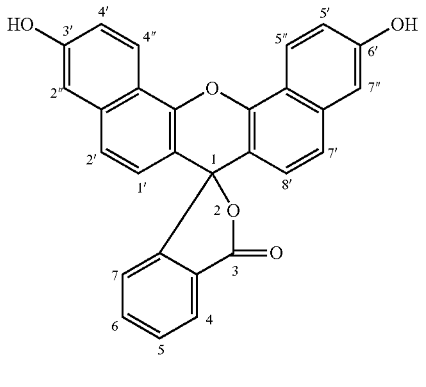

Like the NH-rhodamines, the carbons at positions C1', C2', C2", C4', C4", C5', C5", C7', C7", C8', C4, C5, C6 and C7 of the fluoroescein rings of structural formulae (IVa), (IVb) and (IVc) can be substituted with a variety of different substituents, such as those described previously for the NH-rhodamines.

When included in the label moieties described herein, the hydroxyls at the C3' and C6' positions should be protected with protecting groups having the same general properties as the groups protecting the exocyclic amines of the NH-rhodamines, discussed above. Thus, in specific embodiments the protecting groups are stable to the conditions used to synthesize oligonucleotides, such as the conditions used to synthesize and oxidize oligonucleotides via the phosphite triester method, and are labile under the conditions typically used to deprotect and/or cleave synthetic oligonucleotides from the synthesis resin, such as, for example, incubation in concentrated ammonium hydroxide at room temperature or 55° C.

Fluoresceins in which the C3' and C6' exocyclic hydroxyls include protecting groups are referred to herein as "O-protected fluoresceins." O-protected fluoresceins corresponding to the fluoresceins of structural formulae (IVa), (IVb) and (IVc), respectively, are illustrated as structural formulae (Va), (Vb) and (Vc), below:

(Va)

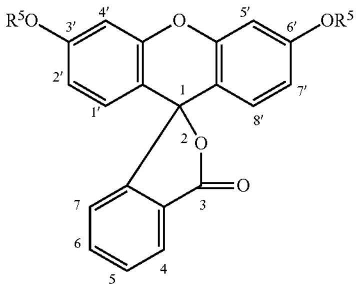

(Vb)

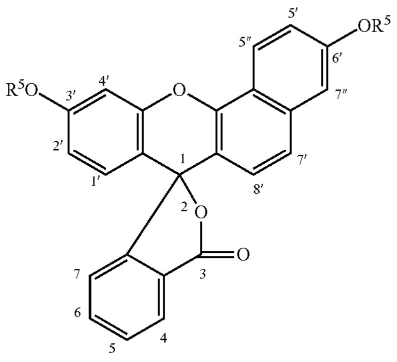

-continued (Vc)

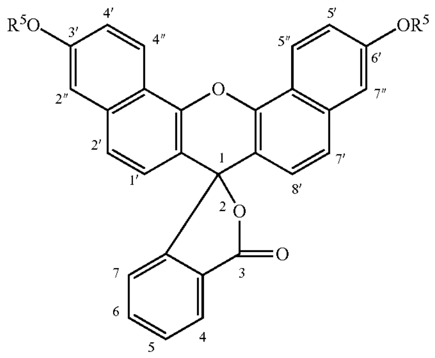

wherein $R^5$ represents the protecting group.

A variety of different fluorescein dyes that can be suitably protected and incorporated into label moieties for use as a donors for the NH-rhodamine moiety are known in the art. Specific exemplary fluorescein dyes are described, for example, in U.S. Pat. Nos. 6,221,604; 6,008,379; 5,840,999; 5,750,409; 5,654,441; 5,188,934; 5,066,580; 4,481,136; 4,439,356; WO 99/16832; and EP 0 050 684, the disclosures of which are incorporated herein by reference. Skilled artisans will be able to select a fluorescein having spectral properties suitable for use as a donor for a specific NH-rhodamine.

The donor and N-protected NH-rhodamine acceptor can be linked to one another in a variety of orientations, either directly or with the aid of a linker. In some embodiments in which the donor is an O-protected fluorescein or an N-protected NH-rhodamine, the donor is linked to the C2'-, C4'-, C5'-, C7'-, C5- or C6-position of the N-protected NH-rhodamine acceptor via its C2'-, C2"-, C4'-, C5'-, C7'-, C7"-, C5- or C6-position.

Specific exemplary linkage orientations are provided in Table 2, below:

TABLE 2

| Donor/Acceptor | Acceptor/Donor | Name |
|---|---|---|
| C4' or C5' | C4' or C5' | head-to-head |
| C4' or C5' | C5 or C6 | head-to-tail |
| C5 or C6 | C5 or C6 | tail-to-tail |
| C2' or C7' | C2', C2", C7' or C7" | side-to-side |
| C2' or C7' | C4' or C5' | side-to-head |
| C2' or C7' | C5 or C6 | side-to-tail |

Label moieties comprising dye networks, such as the donor-acceptor dye networks of Table 2, can be linked to the remainder of the reagent at any available position. In some embodiments, label moieties comprising head-to-head linked acceptor/donor pairs are attached to the remainder of the reagent via the C5- or C6-position of the donor or acceptor moiety. In some embodiments, label moieties comprising head-to-tail linked acceptor/donor pairs are attached to the remainder of the reagent via an available C4'-, C5'-, C5- or C6-position of the donor or acceptor moiety. In some embodiments, label moieties comprising tail-to-tail linked acceptor/donor pairs are attached to the remainder of the reagent via the C4'- or C5'-position of the donor or acceptor. In some embodiments, label moieties comprising side-to-side linked acceptor/donor pairs are attached to the remainder of the reagent via the C4'-, C5'-, C5- or C6-position of the donor or acceptor. In some embodiments, label moieties comprising side-to-head linked acceptor/donor pairs are attached to the remainder of the reagent via an available C4'-, C5'-, C5- or C6-position of the donor or acceptor. In some embodiments, label moieties comprising side-to-tail linked acceptor/donor pairs are attached to the remainder of the reagent via an available C4'-, C5'-, C5- or C6-position of the donor or acceptor.

Regardless of their orientation, the O-protected fluorescein or N-protected NH-rhodamine donor and the N-protected NH-rhodamine acceptor are typically linked to one another via a linker. It has been discovered previously that it may be advantageous to link such donor and acceptor dyes via linkers that are rigid in nature and/or that are relatively long, for example, in the range of approximately 12-20 Angstroms in length (as used herein, the "length" of a linker refers to the distance between the linked moieties as determined by calculating the sum of the lengths of the chemical bonds defining the shortest continuous path between the moieties). Without intending to be bound by any theory of operation, it is believed that linkers that tend to hold the donor and acceptor in close proximity to one another without permitting their chromophores to touch one another yield suitably efficient energy transfer. In this regard, the rigidity and length of the linker are coupled parameters. Generally, shorter linkers (for example linkers having a length of about 5 to 12 Angstroms) should include a greater degree of rigidity. Longer linkers (for example linkers having a length in the range of about 15 to 30 Angstroms) can include a lesser degree of rigidity, or even no rigidity. Short, non-rigid (floppy) linkers should be avoided.

Figure 1:
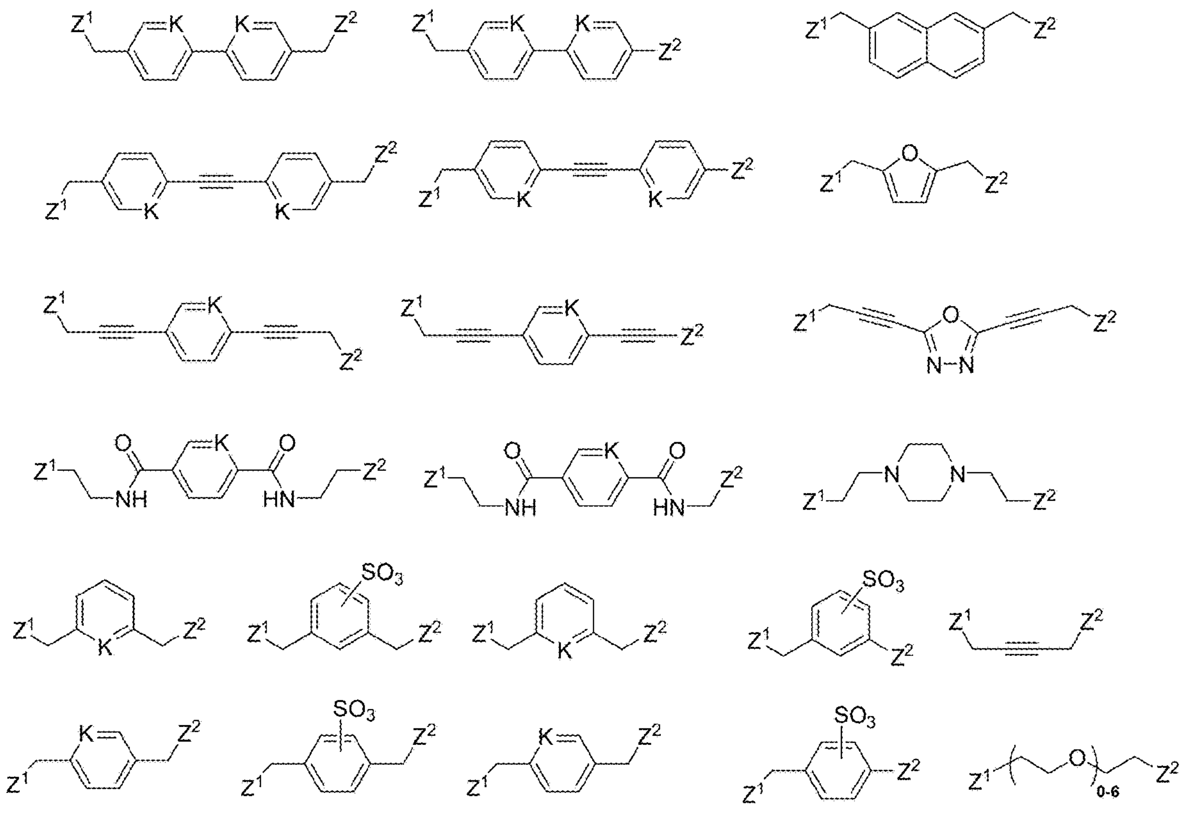

Rigidity can be achieved through the use of groups that have restricted angles of rotation about their bonds, for example, through the use of arylene or heteroarylene moieties, and/or alkylene moieties that comprise double and/or triple bonds. A variety of linkers useful for linking rhodamine and fluorescein dyes to one another in the context of energy transfer dyes are known in the art, and are described, for example, in U.S. Pat. No. 5,800,996, the disclosure of which is incorporated herein by reference. Specific examples of linkers useful for linking O-protected fluorescein or N-protected NH-rhodamine donors to N-protected NH-rhodamine acceptors in the label moieties described herein include, by way of example and not limitation, groups of the formula:

$$—Z—(CH_2)_a—[(Ar)_b—(CH_2)_a]_c—Z—; \quad (L.1)$$

$$—Z—(CH_2)_a—[C{\equiv}C—(CH_2)_a]_c—Z—; \quad (L.2)$$

$$—Z—(CH_2)_a—[C{\equiv}C—(Ar)_b]_c—(CH_2)_a—Z—; \quad (L.3)$$

$$—Z—(CH_2)_d—NH—C(O)—[(CH_2)_a—(Ar)—(CH_2)_a—C(O)—NH]_c—(CH_2)_d—Z—; \text{ and} \quad (L.4)$$

$$—Z—[CH_2(CH_2)_eO]_f—CH_2(CH_2)_eO—, \quad (L.5)$$

where each Z represents, independently of the others, a portion of a linkage contributed by a linking group $F^z$, as previously described, each a represents, independently of the others, an integer ranging from 0 to 4; each b represents, independently of the others, an integer ranging from 1 to 2; each c represents, independently of the others, an integer ranging from 1 to 5; each d represents, independently of the others, an integer ranging from 1 to 10; each e represents, independently of the others, an integer ranging from 1 to 4; each f represents, independently of the others, an integer ranging from 1 to 10; and each Ar represents, independently of the others, an optionally substituted monocyclic or polycyclic cycloalkylene, cycloheteroalkynene, arylene or heteroarylene group. Non-limiting exemplary embodiments of Ar include groups derived from lower cycloalkanes, lower cycloheteroalkanes, parent aromatic ring systems and parent heteroaromatic ring systems, as described previously. Specific, non-limiting exemplary embodiments of Ar include cyclohexane, piperazine, benzene, napthalene, phenol, furan, pyridine, piperidine, imidazole, pyrrolidine and oxadizole. Specific, non-limiting exemplary embodiments of linkers are illustrated in FIG. 1. In FIG. 1, $Z^1$ and $Z^2$ each represent, independently of one another, a portion of a linkage contributed by a functional group $F^z$, as previously described, and K is selected from —CH— and —N—. In some specific embodiments of the linkers illustrated in FIG. 2, one of $Z^1$ or $Z^2$ is —NH— and the other is selected from —O—, —C(O)— and —$S(O)_2$—.

In some embodiments, the linker linking the donor and acceptor dyes is an anionic linker as described in U.S. Pat. No. 6,811,979, the disclosure of which is incorporated herein by reference (see, e.g., the disclosure at Col. 17, line 25 through Col. 18, line 37 and FIGS. 1-17). Specific, non-limiting exemplary embodiments of suitable anionic linkers include the linkers of formulae (L.1) through (L.4), above, in which one or more of the Ar groups are substituted with one or more substituent groups having a negative charge under the conditions of use, such as, for example, at a pH in the range of about pH 7 to about pH 9. Specific, non-limiting examples of suitable substituent groups include phosphate esters, sulfate esters, sulfonate and carboxylate groups.

In some embodiments, t the linker linking the donor and acceptor dyes is an anionic linker as described in U.S. Pat. No. 6,811,979, the disclosure of which is incorporated herein by reference (see, e.g., the disclosure at Col. 17, line 25 through Col. 18, line 37 and FIGS. 1-17). Specific, non-limiting exemplary embodiments of suitable anionic linkers include the linkers of formulae (L.1) through (L.4), above, in which one or more of the Ar groups are substituted with one or more substituent groups having a negative charge under the conditions of use, such as, for example, at a pH in the range of about pH 7 to about pH 9. Specific, non-limiting examples of suitable substituent groups include phosphate esters, sulfate esters, sulfonate and carboxylate groups.

In some embodiments, the label moiety is of the formula (VI):

$$A\text{-}Z^1\text{-}Sp\text{-}Z^2\text{-}D \quad (VI)$$

where A represents the N-protected NH-rhodamine acceptor, D represents the donor, for example, an N-protected NH-rhodamine or O-protected fluorescein donor, $Z^1$ and $Z^2$ represent portions of linkages provided by linking moieties comprising a functional group $F^z$, as previously described, and Sp represents a spacing moiety, as previously described. In some specific embodiments, A is a N-protected NH-rhodamine moiety as described herein, and D is selected from the group consisting of moieties having structural formulae D.1, D.2, D.3, D.4, D.5, D.6, D.7, D.8, D.9, D.10, D.11 and D.12:

(D.1)
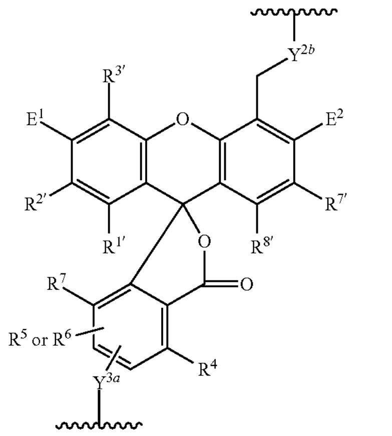
(D.2)
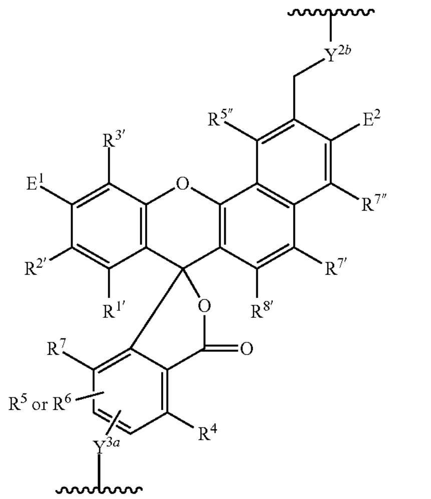
(D.3)
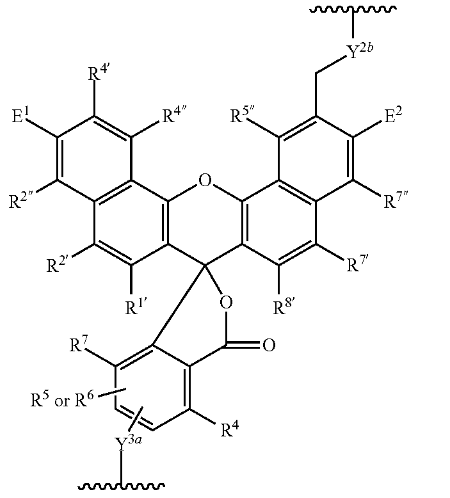
-continued
(D.4)
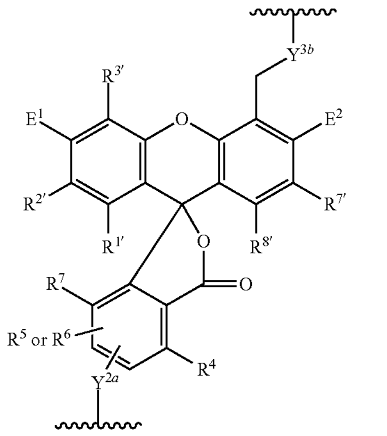
(D.5)
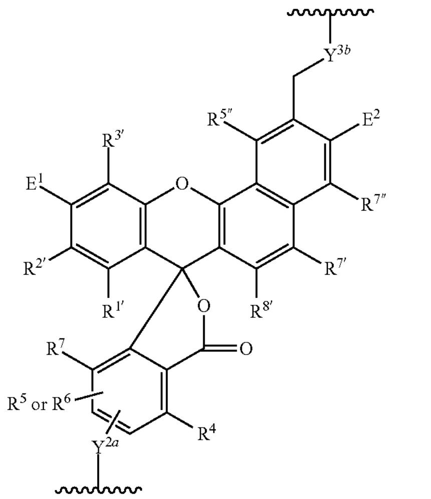
(D.6)
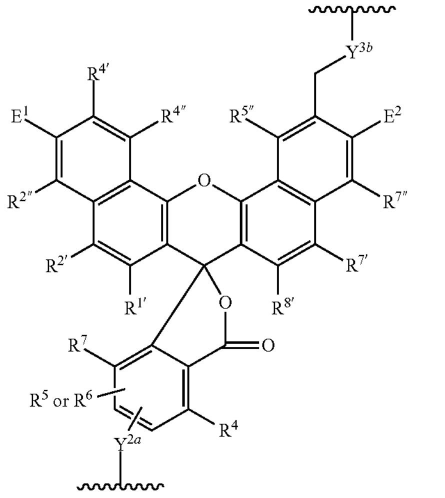

-continued (D.7)

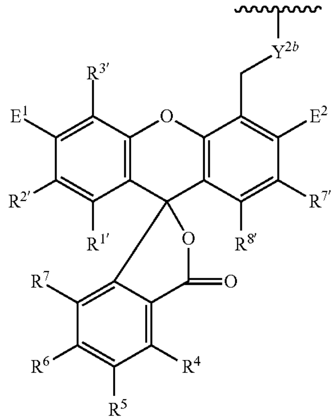

(D.8)

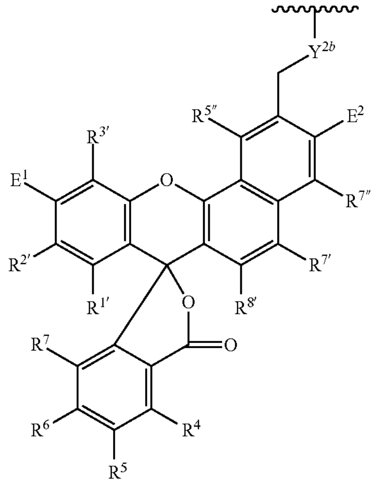

(D.9)

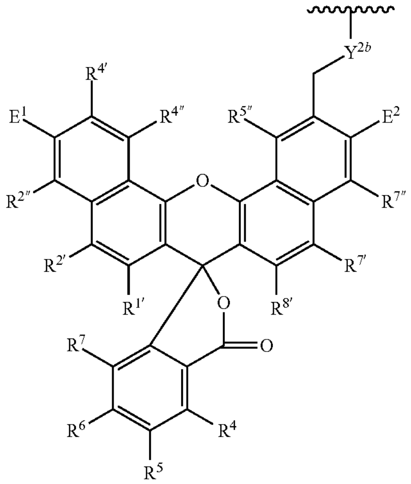

-continued (D.10)

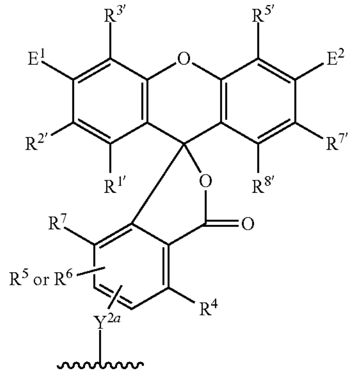

(D.11)

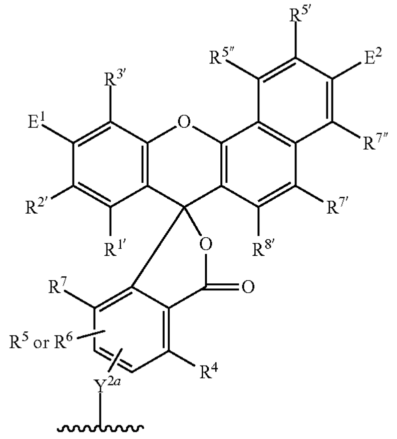

(D.12)

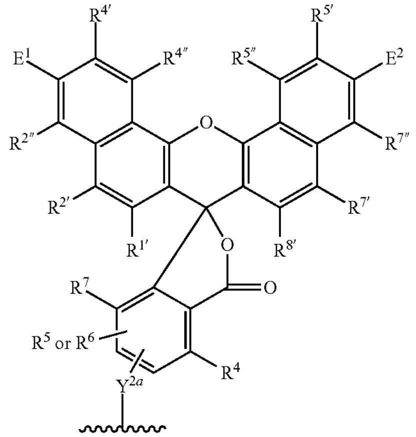

wherein, in each of D.1-D.12:

each of $R^{1'}$, $R^{2'}$, $R^{2''}$, $R^{4'}$, $R^{4''}$, $R^{5'}$, $R^{5''}$, $R^{7'}$, $R^{7''}$ and $R^{8'}$, when taken alone, is independently selected from the group consisting of hydrogen, a lower alkyl, a (C6-C14) aryl, a (C7-C20) arylalkyl, a 5-14 membered heteroaryl, a 6-20 membered heteroarylalkyl, —$R^b$ and —$(CH_2)_x$—$R^b$, wherein x is an integer having the value between 1 and 10 and $R^b$ is selected from the group consisting of —X, —OH, —$OR^a$—SH, —$SR^a$—$NH_2$, —$NHR^a$—$NR^cR^c$, —$N^+R^cR^cR^c$, perhalo lower alkyl, trihalomethyl, trifluoromethyl, —$P(O)(OH)_2$, —$P(O)(OR^a)_2$, $P(O)(OH)(OR^a)$, —$OP(O)(OH)_2$, —$OP(O)(OR^a)_2$, —$OP(O)(OR^a)(OH)$, —$S(O)_2OH$, —$S(O)_2R^a$, —C(O)H, —$C(O)R^a$, —C(S)X, —$C(O)OR^a$, —C(O)OH, —$C(O)NH_2$, —$C(O)NHR^a$, —$C(O)NR^cR^c$, —C(S)$NH_2$, —C(O)$NHR^a$, —C(O)$NR^cR^c$, —C(NH)$NH_2$, —C(NH)$NHR^a$, and —C(NH)$NR^cR^c$, wherein X is halo, each $R^a$ is independently selected from the group consisting of a lower alkyl, a (C6-C14) aryl, a (C7-C20) arylalkyl, a 5-14 membered heteroaryl and a 6-20 membered heteroarylalkyl, and each $R^c$ is independently an $R^a$, or, alternatively, two $R^c$ bonded to the same nitrogen atom may be taken together with that nitrogen atom to form a 5- to 8-membered saturated or unsaturated ring that may optionally include one or more of the same or different ring heteroatoms selected from the group consisting of 0, N, and S;

or, alternatively, $R^{1'}$ and $R^{2'}$ or $R^{7'}$ and $R^{8'}$ are taken together with the carbon atoms to which they are bonded to form an optionally substituted (C6-C14) aryl bridge and/or $R^{4'}$ and $R^{4''}$ and/or $R^{5'}$ and $R^{5''}$ are taken together with the carbon atoms to which they are bonded to form a benzo group; and $R^4$, $R^5$, $R^6$, and $R^7$ are each, independently of one another, selected from hydrogen, lower alkyl, (C6-C14) aryl, (C7-C20) arylalkyl, 6-14 membered heteroaryl, 7-20 membered heteroarylalkyl, —$R^b$ and —$(CH_2)_x$—$R^b$;

$E^1$ is selected from the group consisting of —$NHR^9$, —$NR^9R^{10}$ and —$OR^{9b}$;

$E^2$ is selected from the group consisting of —$NHR^9$, —$NR^9R^{10}$ and —$OR^{9b}$;

$R^9$ and $R^{10}$ are as described herein;

$R^{9b}$ is $R^9$;

each of $Y^{1a}$, $Y^{1b}$, $Y^{2a}$, $Y^{2b}$, $Y^{3a}$ and $Y^{3b}$ is independently selected from the group consisting of —O—, —S—, —NH—, —C(O—) and —$S(O)_2$—, with the proviso that when each of $E^1$ and $E^2$ is —$OR^{9b}$, then $R^{1'}$ and $R^{2'}$ and/or $R^{7'}$ and $R^{8'}$ may only be taken together with the carbon atoms to which they are bound to form an optionally substituted (C6-C14) aryl bridge.

As used herein, "asymmetric rhodamines" are compounds in which E1 and E2 is independently —NHR9 or —NR9R10 and E1 is not the same as E2.

In some specific embodiments of label moieties according to structural formula (VI), $Y^{1a}$, $Y^{2a}$ and $Y^{3a}$ are —NH—; $Y^{1b}$, $Y^{2b}$ and $Y^{3b}$ are selected from —C(O)— and —$S(O)_2$—; Z1 is selected from —C(O)— and —$S(O)_2$—; $Z^2$ is —NH— and Sp is a group selected from:

$$—(CH_2)_a—[(Ar)_b—(CH_2)_a]_c—; \quad (Sp.1)$$

$$—(CH_2)_a—[C{\equiv}C—(CH_2)_a]_c—; \quad (Sp.2)$$

$$—(CH_2)_a—[C{\equiv}C—(Ar)_b]_c—(CH_2)_a—; \quad (Sp.3)$$

$$—(CH_2)_d—NH—C(O)—[(CH_2)_a—(Ar)—(CH_2)_a—C(O)—NH]_c—(CH_2)_d— \quad (Sp.4); \text{ and}$$

$$—[CH_2(CH_2)_eO]_f—CH_2(CH_2)—, \quad (Sp.5)$$

where a, b, c, d, e, f and Ar are as previously defined.

In some specific embodiments of label moieties according to structural formula (VI), R9 is selected from —C(O)$CH_3$ and C(O)$CF_3$ and $R^{9a}$ is —C(O)$C(CH_3)_3$.

4.5 PEP Group

Many embodiments of the reagents described herein include a PEP group ("PEP"). When used in a step-wise synthesis to synthesize a labeled oligonucleotide, the PEP group is coupled to any available hydroxyl group, which may be the 5'-hydroxyl group of a nascent synthetic oligonucleotide, ultimately contributing, after any required oxidation and/or deprotection steps, a linkage linking the label moiety to the synthetic oligonucleotide. The linkage formed may be a phosphate ester linkage or a modified phosphate ester linkage as is know in the art.

A variety of different groups suitable for coupling reagents to primary hydroxyl groups to yield phosphate ester or modified phosphate ester linkages are well-known in the art. Specific examples include, by way of example and not limitation, phosphoramidite groups (see, e.g., Letsinger et al., 1969, J. Am. Chem. Soc. 91:3350-3355; Letsinger et al., 1975 J. Am. Chem. Soc. 97:3278; Matteucci & Caruthers, 1981, J. Am. Chem. Soc. 103:3185; Beaucage & Caruthers, 1981, Tetrahedron Lett. 22:1859; the disclosures of which are incorporated herein by reference), 2-chlorophenyl- or 2,5-dichlorophenyl-phosphate groups (see, e.g., Sproat & Gait, "Solid Phase Synthesis of Oligonucleotides by the Phosphotriester Method," In: Oligonucleotide Synthesis, A Practical Approach, Gait, Ed., 1984, IRL Press, pages 83-115), the disclosures of which are incorporated herein by reference), and H-phosphonate groups (see, e.g., Garegg et al., 1985, Chem. Scr. 25:280-282; Garegg et al., 1986, Tet. Lett. 27:4051-4054; Garegg et al. 1986, Tet. Lett. 27:4055-4058; Garegg et al., 1986, Chem. Scr. 26:59-62; Froehler & Matteucci, 1986, Tet. Lett. 27:469-472; Froehler et al., 1986, Nucl. Acid Res. 14:5399-5407, the disclosures of which are incorporated herein by reference). In a specific embodiment, the PEP group is a phosphoramidite group of the formula (P.1):

(P.1)

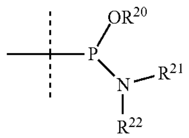

wherein $R^{20}$ is selected from a linear, branched or cyclic saturated or unsaturated alkyl containing from 1 to 10 carbon atoms, 2-cyanoethyl, an aryl containing from 6 to 10 ring carbon atoms and an arylalkyl containing from 6 to 10 ring carbon atoms and from 1 to 10 alkylene carbon atoms; and $R^{21}$ and $R^{22}$ are each, independently of one another, selected from a linear, branched or cyclic, saturated or unsaturated alkyl containing from 1 to 10 carbon atoms, an aryl containing from 6 to 10 ring carbon atoms and an arylalkyl containing from 6 to 10 ring carbon atoms and from 1 to 10 alkylene carbon atoms, or, alternatively, $R^{21}$ and $R^{22}$ are taken together with the nitrogen atom to which they are bonded to form a saturated or unsaturated ring that contains from 5 to 6 ring atoms, one or two of which, in addition to the illustrated nitrogen atom, can be heteroatom selected from O, N and S.

In a specific embodiment, $R^{20}$ is 2-cyanoethyl and $R^{21}$ and $R^{22}$ are each isopropyl.

4.6 Synthesis Handles

Many embodiments of the reagents described herein include one or more synthesis handles that provide, after suitable deprotection, if necessary, sites that can be used for the attachment of additional groups or moieties to the synthetic labeled oligonucleotide. The groups can be attached to a synthesis handle during the course of synthesizing the labeled oligonucleotide, or, alternatively, the synthesis handle can be deprotected post-synthesis to reveal a functional group to which additional groups or moieties can be attached. For example, a synthesis handle could comprise a primary amine group that is protected with a protecting group that is stable to the conditions used to carry out the synthesis of the labeled oligonucleotide. Removal of the protecting group following synthesis, either concurrently with, or separately from, the removal of the various other protecting groups on the synthetic oligonucleotide, provides a primary amino group to which additional groups and/or moieties can be attached.

A variety of different types of reactive groups protected with protecting groups suitable for use in oligonucleotide synthesis are known in the art, and include by way of example and not limitation, amino groups (protected with, for example, trifluoroacetyl or 4-monomethoxytrityl groups), hydroxyl groups (protected with, for example, 4,4'-dimethoxytrityl groups), thiol groups (protected with, for example, trityl or alkylthiol groups) and aldehyde groups (protected with, for example, an acetal protecting group). All of these protected reactive groups can comprise the synthesis handle of the reagents described herein.

In some embodiments, the synthesis handle comprises a protected primary hydroxyl of the formula —$OR^k$, where $R^k$ represents an acid-labile protecting group that can be selectively removed during the course of synthesizing an oligonucleotide. Acid labile protecting groups suitable for protecting primary hydroxyl groups in the context of oligonucleotide synthesis are known in the art, and include, by way of example and not limitation, triphenylmethyl (trityl), 4-monomethoxytrityl, 4,4'-dimethoxytrityl, 4,4',4"-trimethoxytrityl, bis(p-anisyl)phenylmethyl, naphthyldiphenylmethyl, p-(p'-bromophenacyloxy)phenyldiphenylmethyl, 9-anthryl, 9-(9-phenyl)xanthenyl and 9-(9-phenyl-10-oxo) anthryl. All of these groups can be removed by treatment with mild acid, such as by treatment with 2.5% or 3% di- or trichloro acid and in dichoromethane. Methods of protecting primary hydroxyl groups with the above-listed acid-labile protecting groups are well-known.

4.7 Solid Supports

Many embodiments of the reagents described herein comprise solid supports to which the other moieties and/or groups are attached. The solid supports are typically activated with functional groups, such as amino or hydroxyl groups, to which linkers bearing linking groups suitable for attachment of the other moieties are attached.

A variety of materials that can be activated with functional groups suitable for attachment to a variety of moieties and linkers, as well as methods of activating the materials to include the functional groups, are known in the art, and include by way of example, controlled pore glass, polystyrene and graft co-polymers. Any of these materials be used as solid supports in the reagents described herein.

4.8 Synthesis Regents Useful for Terminal Hydroxyl Labeling

Some embodiments of the synthesis reagents described herein are described by structural formula (VII):

LM-L-PEP (VII)

where LM represents a label moiety as described herein, L represents an optional linker as described herein and PEP represents a PEP group as described herein. The reagents can include additional groups or moieties, such as synthesis handles. In some embodiments, the synthesis reagents comprise a label moiety and a PEP group, and do not include additional moieties or groups. Such synthesis reagents can be coupled to a hydroxyl group during the step-wise synthesis of an oligonucleotide, and are useful for, among other things, attaching a label moiety to a terminal hydroxyl group of a synthetic oligonucleotide, which is commonly the 5'-hydroxyl.

In some embodiments, the label moiety can be of the formula (III.1)

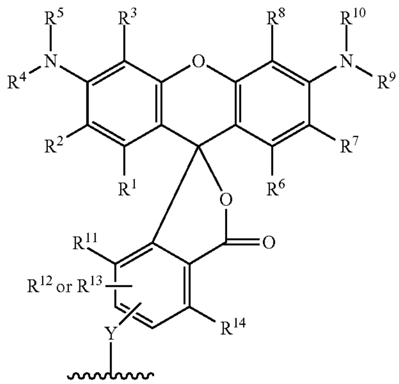

(III.2)

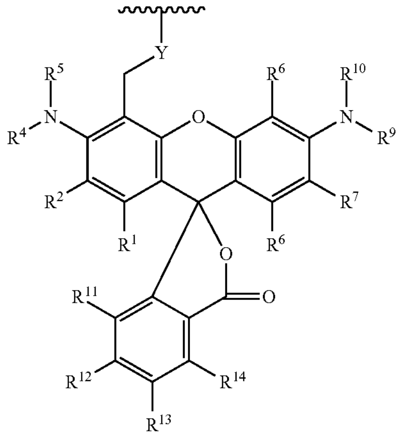

(III.3)

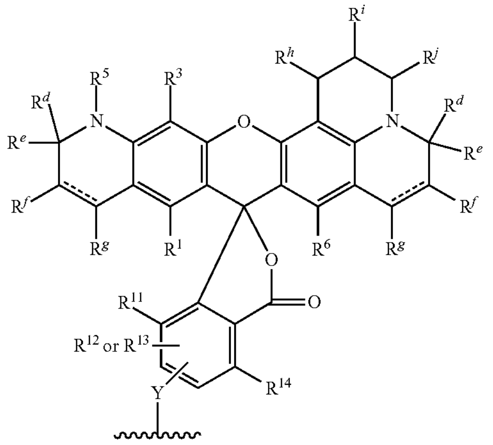

or

-continued (III.4)

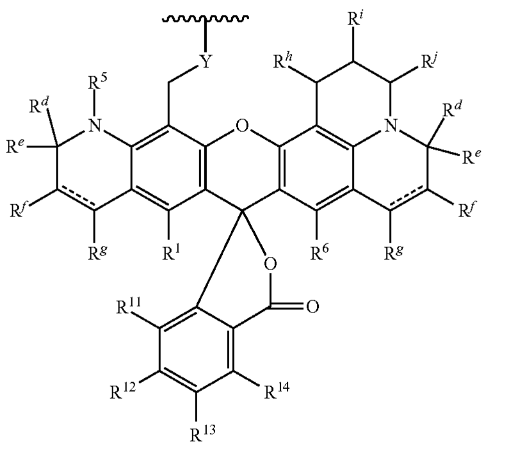

wherein, $R^1$-$R^{14}$, $R^a$-$R^j$, and Y are as defined herein.

The PEP group can be attached directly to the label moiety, or it may be attached to the label moiety with the aid of a linker. As PEP groups are generally linked to molecules by coupling suitable reagents to primary hydroxyl groups, in embodiments in which the PEP group is attached directly to the label moiety, the label moiety should include a substituent group that comprises a primary hydroxyl group. In embodiments in which the PEP group is linked to the label moiety with the aid of a linker, the linker synthon should include a linking group suitable for forming a linkage with a linking group on the label moiety synthon and a primary hydroxyl group suitable for attachment to the PEP group. Suitable linker synthons include, but are not limited to, synthons of the formula $F^z$-Sp-OH, where $F^z$ is a functional group complementary to a functional group on the label moiety synthon and Sp represents a spacing moiety. The spacing moiety can comprise any combination of atoms and/or functional groups stable to the conditions that will be used to synthesize and deprotect the labeled synthetic oligonucleotide. Non-limiting exemplary linkers are illustrated in FIG. 1, where $Z^2$ is O. In some embodiments, Sp is an optionally substituted alkylene chain that contains from 1 to 10 chain atoms. In a specific embodiment, Sp is an unsubstituted alkylene chain containing from 1 to 9 carbon chain atoms.

In some embodiments, the synthesis reagents are compounds according to structural formula (VII) in which:

LM is one of the embodiments of label moieties specifically exemplified above;

L is selected from —Z—$(CH_2)_{3-6}$—O—, —Z—$(CH_2)_a$—$[(Ar)_b$—$(CH_2)_a]_c$—O—, —Z—$(CH_2)_a$—[C≡C—$(CH_2)_a]_c$—O—, —Z—$(CH_2)_a$—[C≡C—$(Ar)_b]_c$—$(CH_2)_a$O—, —Z—$(CH_2)_d$—NH—C(O)—$[(CH_2)_a$—(Ar)—$(CH_2)_a$C(O)—NH$]_c$—$(CH_2)_d$—O—, —Z—$[CH_2(CH_2)_eO]_f$—$CH_2(CH_2)_e$O— and one of the linkers illustrated in FIG. 1 in which $Z_2$ is O; and PEP is a phosphoramidite group, such as for example, a phosphoramidite group of structural formula P.1, as described above. In some specific embodiments, Z in linker L is —NH—.

In some embodiments, the linker in synthesis reagents according to structural formula (VII) comprises a nucleoside, such that the synthesis reagent is nucleosidic. In some embodiments, nucleosidic synthesis reagents are compounds according to structural formula (VII.1):

(VII.1)

Figure 3:
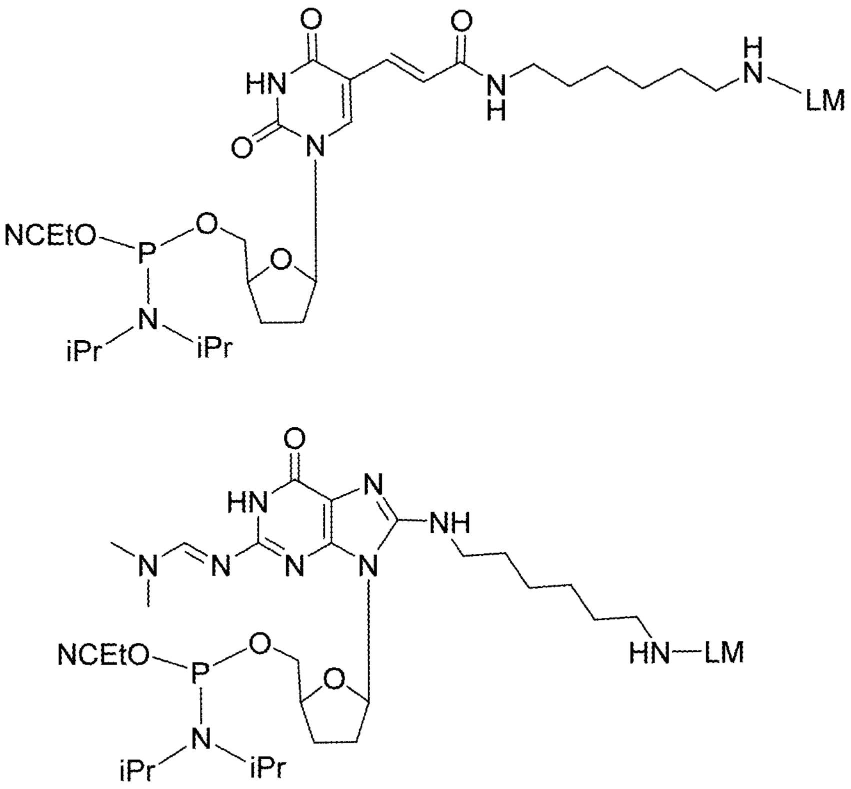

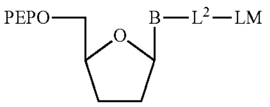

where PEP represents the phosphate ester precursor group, B represents a nucleobase, LM represents the label moiety and L2 represents a linker linking nucleobase B to linker LM. The features and properties of nucleobase B and linker L are described in more detail, below. Non-limiting exemplary nucleosidic synthesis reagents according to structural formula (VII.1) are illustrated in FIG. 3.

An exemplary scheme for synthesizing embodiments of synthesis reagents in which the PEP group is linked to the label moiety via an optional linker is provided in Scheme (I), below, where the various R, $F^y$, $F^z$, Y, Z and Sp groups are as previously defined:

Scheme I

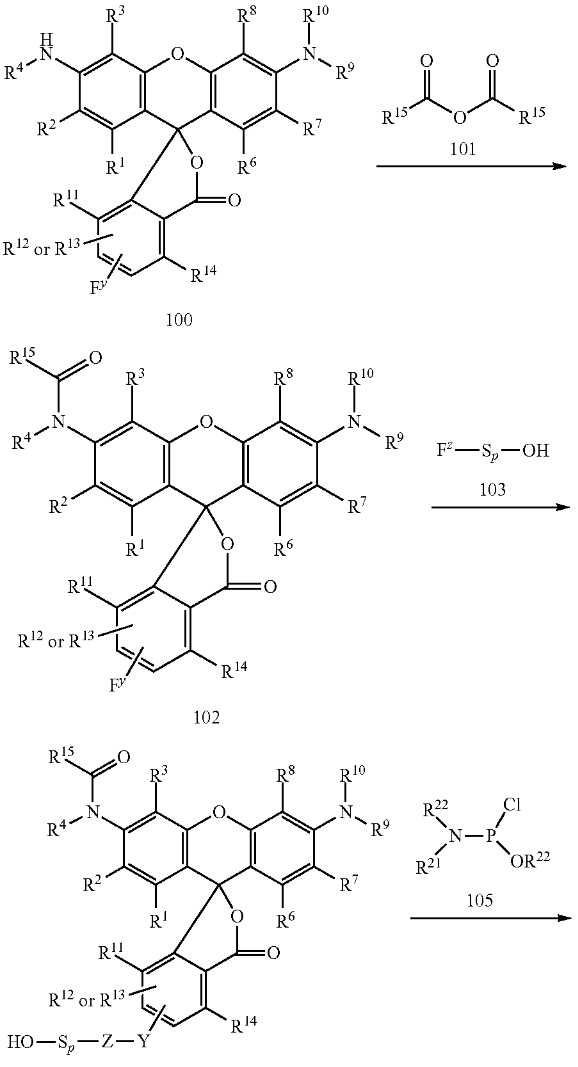

104

-continued

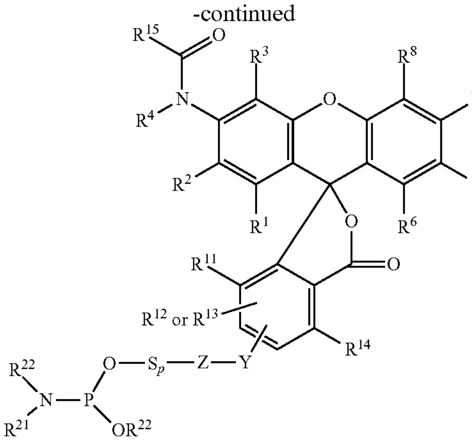

106

In Scheme (I) parent NH-rhodamine synthon 100, which includes a linking group that comprises functional group $F^y$, is acetylated with anhydride 101 to yield N-acetyl-protected NH-rhodamine synthon 102. Synthon 102 is then coupled to linker synthon 103 to yield compound 104. Depending upon the identity of $F^y$, synthon 102 may require activation prior to coupling. For example, if $F^y$ is a carboxyl group, it can be activated as an ester, such as an NHS ester, prior to coupling. In compound 104, —Y—Z— represents the linkage formed by complementary functional groups $F^y$ and $F^z$, where Y represents the portion contributed by $F^y$ and Z represents the portion contributed by $F^z$, as previously described. Compound 104 is then reacted with PEP synthon 105, which in the specific embodiment illustrated is a phosphine, to yield phosphoramidite synthesis reagent 106.

4.9 Synthesis Reagents Useful for Internal or 3'-End Labeling

The synthesis reagents described herein may optionally include one or more synthesis handles useful for the attachment of additional groups and/or moieties. Synthesis reagents that include a synthesis handle of the formula $—OR^k$, where $R^k$ represents an acid-labile protecting group as previously described, provide a primary hydroxyl group to which additional nucleotides can be attached. As a consequence, synthesis reagents that include such a synthesis handle can be used to label synthetic oligonucleotides at the 5'-hydroxyl, the 3'-hydroxyl or at one or more internal positions. They can also be coupled to one another, or to other phosphoramidite labeling reagents, permitting the synthesis of oligonucleotides containing a plurality of label moieties.

The label moiety, PEP group and synthesis handle $—OR^k$ comprising the synthesis reagent can be linked together in any fashion and/or orientation that permits them to perform their respective functions. As a specific example, the PEP group and synthesis handle can each be linked to the label moiety, optionally via linkers. In some embodiments, such synthesis reagents are compounds according to structural formula (VIII):

$R^kO$-L-LM-L-PEP (VIII)

where each L represents, independently of the other, an optional linker, LM represents the label moiety and PEP represents the PEP group. Non-limiting examples of suitable protecting groups $R^k$, linkers L, label moieties LM and PEP groups include those specifically exemplified above.

As another specific example, the PEP group and synthesis handle $—OR^k$ may be attached to a branched linker that is attached to the label moiety. In some embodiments, such synthesis reagents are compounds according to structural formula (IX):

(IX)

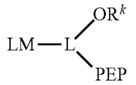

where L represent a linker, LM represents the label moiety and PEP represents the PEP group.

In a specific embodiment, synthesis reagents according to structural formula (IX) are compounds according to structural formula (IX.1):

(IX.1)

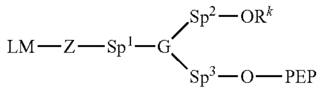

where LM represents the label moiety, —Z— represents a portion of a linkage contributed by a functional $F^z$ on the linker, $Sp^1$, $Sp^2$ and $Sp^3$, which can be the same or different, each represent spacing moieties, G represents CH, N, or a group comprising and arylene, phenylene, heteroarylene, lower cycloalkylene, cyclohexylene, and/or lower cycloheteroalkylene, and PEP represents the PEP group. In some embodiments, LM is one of the embodiments of label moities specifically exemplified above, $Sp^1$, $Sp^2$ and $Sp^3$ are each, independently of one another, selected from an alkylene chain containing from 1 to 9 carbon atoms, Sp.1, Sp.2, Sp.3, Sp.4 and Sp.5 (defined above), and/or PEP is a phosphoramidite group according to structural formula P.1, supra. Non-limiting specific embodiments of exemplary synthesis reagents according to structural formula (IX.1) are illustrated in FIGS. 2 and 3.

In some embodiments, the synthesis handle $—OR^k$ is provided by a nucleoside, such that the synthesis reagent is nucleosidic. In such nucleosidic synthesis reagents, the label moiety is typically linked to the nucleobase of the nucleoside by way of a linker, and any exocyclic functional groups on the nucleobase that are reactive under the conditions used to synthesize the labeled oligonucleotide, such as, for example, exocyclic amines, are protected. Examples are provided in FIG. 5

The nucleoside can be any nucleoside that can be suitably protected for use in the synthesis of oligonucleotides, and may comprise a 2'-deoxyribose sugar moiety, a 3'-deoxyribose sugar moiety (useful for synthesizing labeled oligonucleotides including a 2'-5' internucleotide linkage), a suitably protected ribose moiety, a substituted version of any of these ribose moieties, or even a non-ribose sugar moiety.

In some embodiments, such nucleosidic synthesis reagents are compounds according to structural formulae (IX.2), (IX.3), (IX.4) and (IX.5):

(IX.2)

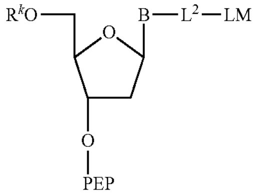

(IX.3)

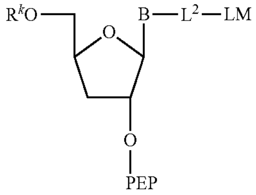

(IX.4)

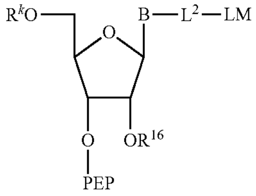

(IX.5)

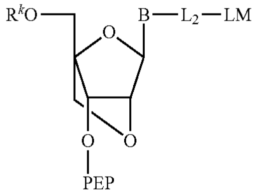

wherein LM represents the label moiety, B represents a suitably protected nucleobase, $L^2$ represents a linker linking the label moiety to the nucleobase, $R^k$ represents the acid-labile protecting group, PEP represents the PEP group, O is an oxygen atom and, in structural formula (IX.4), $R^{16}$ represents a 2'-hydroxyl protecting group.

In the synthesis reagents according to structural formulae (VII.1), (IX.2), (IX.3), (IX.4) and (IX.5), the nucleobase B can be virtually any heterocycle useful for incorporation into oligonucleotides. For example, the nucleobase may be one of the genetically encoding purines (adenine or guanine), one of the genetically encoding pyrimidines (cytosine, uracil or thymine), analogs and/or derivatives of the genetically encoding purines and/or pyrimidines (e.g., 7-deazadenine, 7-deazaguanine, 5-methylcytosine), non-genetically encoding purines and/or pyrimidines (e.g., inosine, xanthene and hypoxanthene) or other types of heterocycles. A wide variety of heterocycles useful for incorporating into oligonucleotides are known in the art and are described, for example, in *Practical Handbook of Biochemistry and Molecular Biology*, Fasman, Ed., 1989, CRC Press (see, e.g., pages 385-393 and the references cited therein), the disclosures of which are incorporated herein by reference. All of these various heterocycles, as well as those that are later discovered, can be included in the nucleosidic synthesis reagents described herein.

When B is a purine in the synthesis reagents according to structural formulae (VII.1), (IX.2), (IX.3), (IX.4) and (IX.5), the illustrated sugar moiety is typically attached to the N9 position of the purine, and when B is a pyrimidine, the illustrated sugar moiety is typically attached at the NI position of the pyrimidine. Attachment sites for other nucleobases will be apparent to those of skill in the art.

Any exocyclic amine or other reactive group(s) on the nucleobase are protected with protecting groups that are stable to the synthesis conditions used to synthesize the labeled oligonucleotide. A variety of groups that are suitable for protecting the exocyclic amine groups of nucleoside nucleobases in the context of oligonucleotide synthesis are well-known in the art, as are methods of preparing such protected nucleosides.

For example, groups that have been used to protect the exocyclic amine of adenine include benzyol (Bz), phenoxyacetyl (Pac) and isobutyryl (iBu). Groups that have been used to protect the exocyclic amine of cystosine include acetyl (Ac) and Bz. Groups that have been used to protect the exocyclic amine of guanine include iBu, dimethylformamide (Dmf) and 4-isopropyl-phenoxyacetyl (iPr-Pac). All of these protecting groups can be removed by treatment with ammonium hydroxide at 55-65° C. for 2-3 hr. However, certain of these protecting groups can be removed under milder conditions. For example, cleavage of the protecting groups from $A^{iBU}$, $A^{Pac}$, $C^{Ac}$ and $G^{iPr\text{-}Pac}$ can be effected in 4-17 hrs at room temperature with ammonium hydroxide, or with 0.05M potassium carbonate in methanol, or treatment with 25% t-butylamine in $H_2O$/EtOH. As some of the NH-rhodamine and/or other dyes comprising the reagents described herein may not be stable to the harsher deprotection conditions required by other protecting groups, nucleosidic reagents which utilize protecting groups that can be removed under these milder deprotection conditions are preferred.

The linker $L^2$ linking the label moiety LM to the nucleobase B may be attached to any position of the nucleobase. In some embodiments, when B is a purine, the linker is attached to the 8-position of the purine, when B is a 7-deazapurine, the linker is attached to the 7-position of the 7-deazapurine, and when B is a pyrimidine, the linker is attached to the 5-position of the pyrimidine.

In some embodiments, linkers $L^2$ useful for attaching LM to a nucleobase comprise an acetylenic or alkenic amino linkage, such as, for example, a linkage selected from $—C{\equiv}C—CH_2—NH—$, $—C{\equiv}C—C(O)—$, $—CH{=}CH—NH—$, $—CH{=}CH—C(O)—$, $—C{\equiv}C—CH_2—NH—C(O)—(CH_2)_{1\text{-}6}—NH—$, and $—CH{=}CH—C(O)—NH—(CH_2)_{1\text{-}6}—NH—C(O)—$, a propargyl-1-ethoxyamino linkage, such as, for example, a linkage having the formula $—C—CH—CH_2—O—CH_2CH_2—[O—CH_2CH_2]_{0\text{-}6}—NH—$ or a rigid linkage, such as for example, a linkage selected from $—C{\equiv}C—C{\equiv}C—CH_2—O—CH_2CH_2—[O—CH_2CH_2]_{0\text{-}6}—NH—$, $—C{\equiv}C—(Ar)_{1\text{-}2}—C{\equiv}C—CH_2—O—CH_2CH_2—[O—CH_2CH_2]_{0\text{-}6}—NH—$, $—C{\equiv}C—(Ar)_{1\text{-}2}—O—CH_2CH_2—[O—CH_2CH_2]_{0\text{-}6}—NH—$ and $—C{\equiv}C—(Ar)_{1\text{-}2}—O—CH_2CH_2—[O—CH_2CH_2]_{0\text{-}6}—NH—$, where Ar is as defined previously.

In some embodiments, linkers $L^2$ useful for attaching LM to a purine nucleobase comprise an alkylamine, such as, for example, a linkage of the formula $—NH—(CH_2)_{1\text{-}6}—NH—$.

In some embodiments, linkers $L^2$ useful for attaching LM to a purine or pyrimidine nucleobase are anionic linkers as described in U.S. Pat. No. 6,811,979, the disclosure of which is incorporated herein by reference (see, e.g., the disclosure at Col. 17, line 25 through Col. 18, line 37 and FIGS. 1-17).

Methods of synthesizing nucleosides derivatized with linkers such as those described above that are suitable for incorporating into the reagents described herein are described, for example, in Hobbs et al., 1989, J. Org. Chem.

54:3420; U.S. Pat. No. 5,151,507 to Hobbs et al., U.S. Pat. No. 5,948,648 to Khan et al.; and U.S. Pat. No. 5,821,356 to Khan et al., the disclosures of which are incorporated herein by reference. The derivatized nucleosides can be used as synthons to synthesize nucleosidic synthesis reagents as will be described in more detail, below.

Specific exemplary embodiments of linker-derivatized nucleobases that may comprise the nucleosidic reagents described herein are illustrated below:

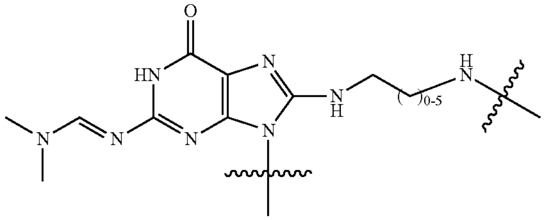

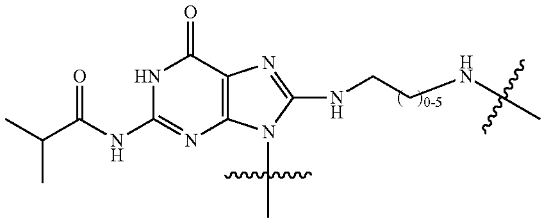

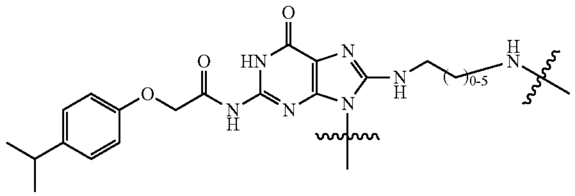

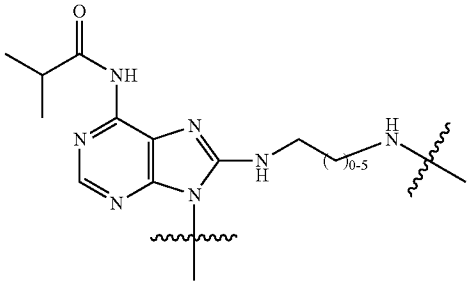

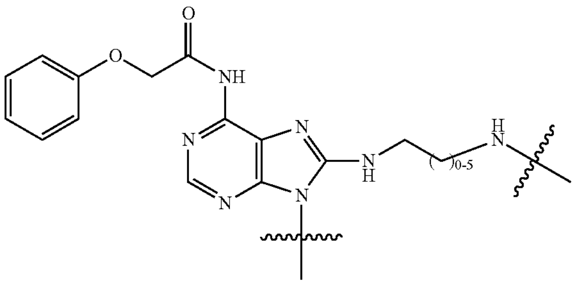

-continued

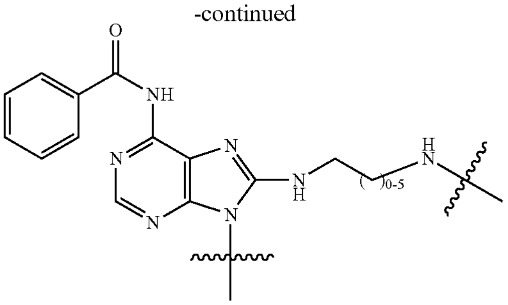

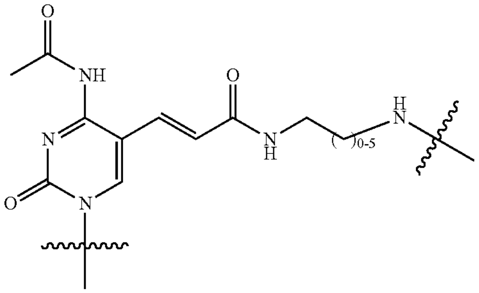

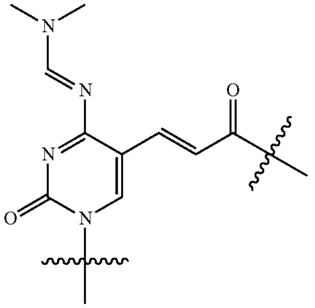

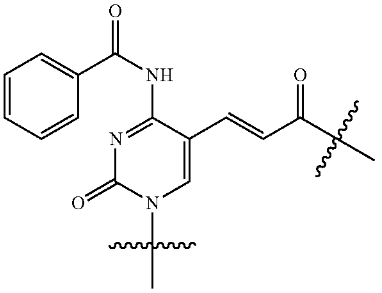

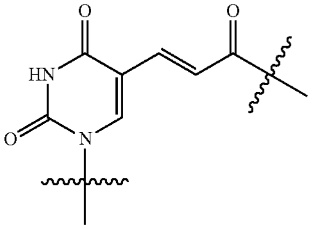

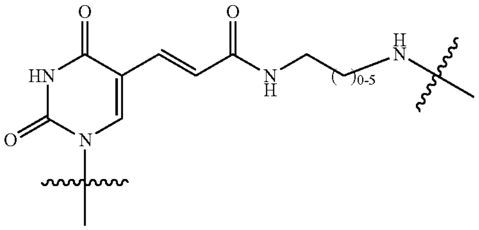

Nucleosidic synthesis reagents can be prepared from linker-derivatized nucleoside synthons as illustrated in Scheme (II), below:

Scheme II

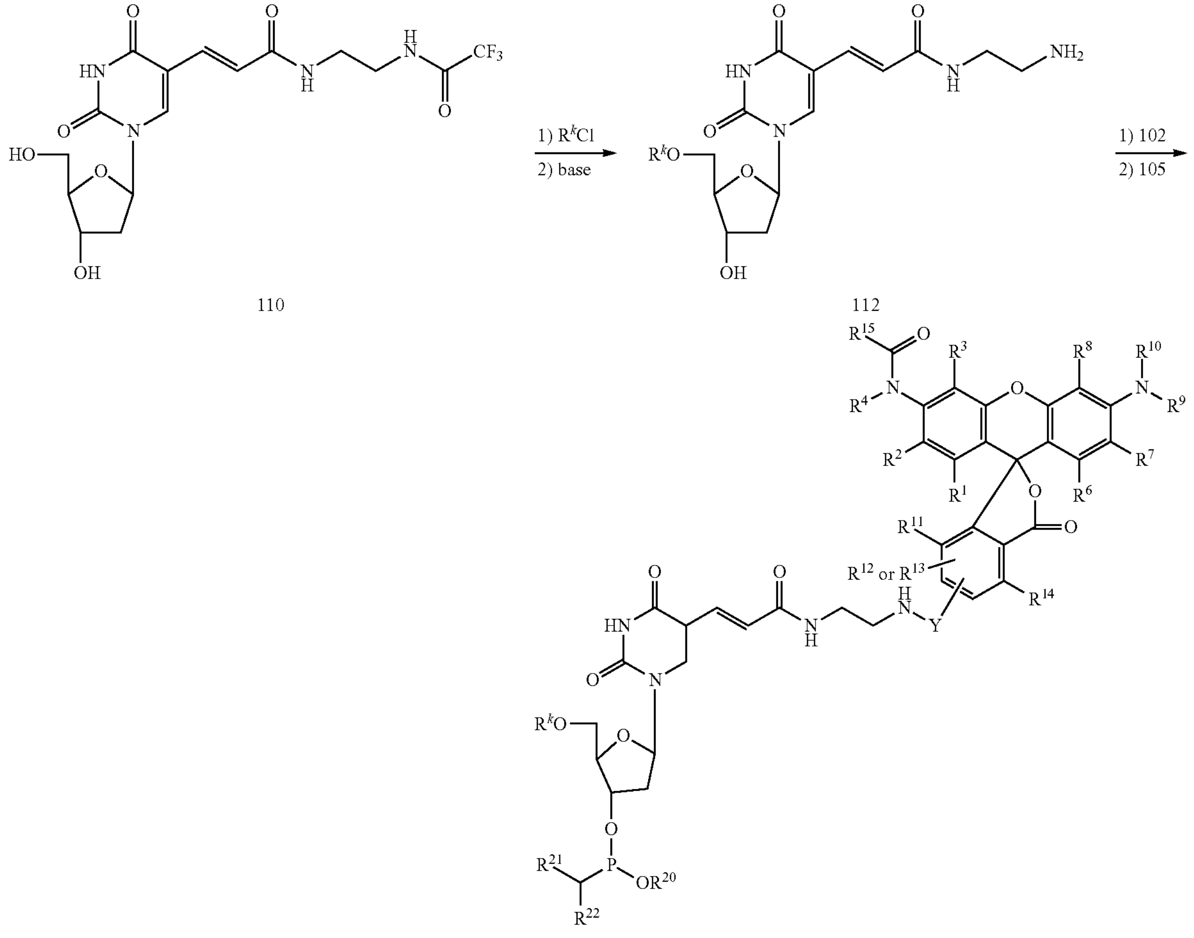

110

112

114

Figure 4:
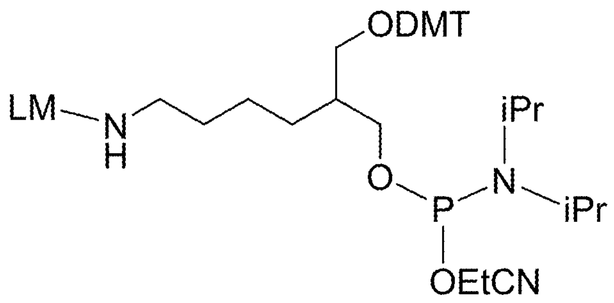
Figure 5:
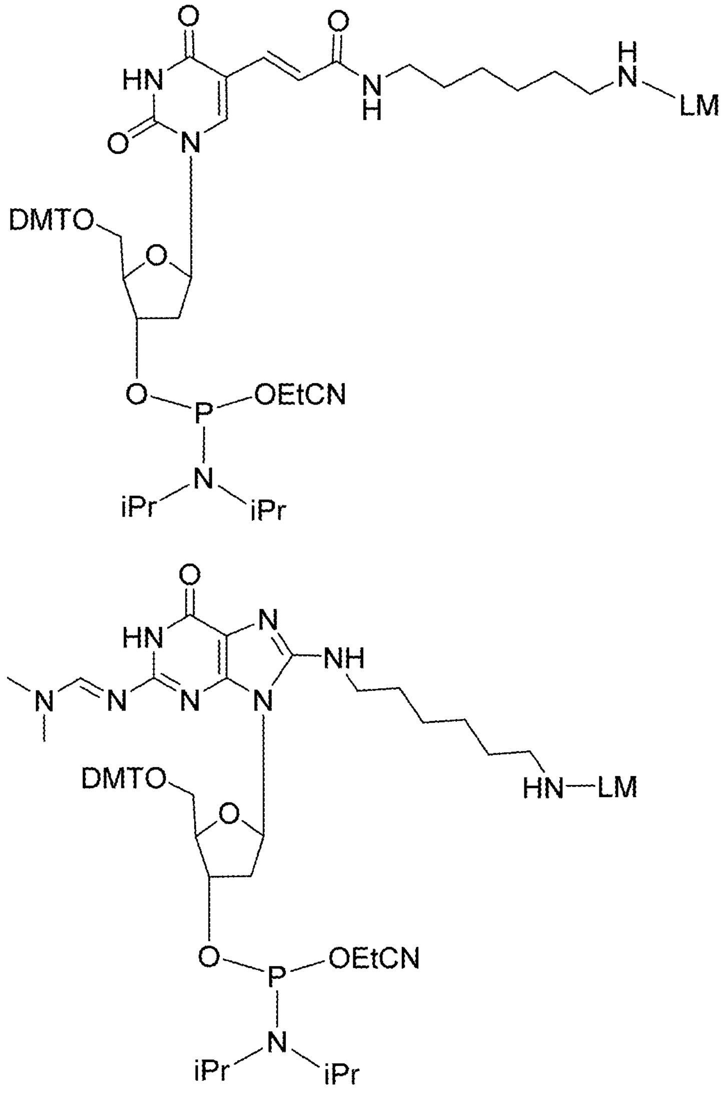

In Scheme (II), linker-derivatized nucleoside synthon 110 is protected at the 5'-hydroxyl with an acid-labile protecting group, which is illustrated in the Scheme with exemplary chloride reagent $R^kCl$, where $R^k$ is as previously defined. Treatment with base to remove the trifluoroacetyl protecting group yields synthon 112. Reaction of synthon 112 with label moiety synthon 102 (see Scheme (I), supra, followed by treatment with PEP synthon 105, which in this specific example illustrated is a phosphine (see Scheme (I), supra) yields nucleosidic synthesis reagent 114. Specific conditions for carrying out the various synthetic steps illustrated above are well known. Non-nucleosidic synthesis reagents that include a synthesis handle, such as shown in FIG. 4 or a synthesis handle of the formula —$OR^k$, can be prepared by routine adaptation of Scheme (II).

4.10 Solid Support Reagents

Many embodiments of the reagents described herein include solid supports. Such reagents generally comprise a solid support, a label moiety as described herein and a synthesis handle, and may include additional groups or moieties, such as additional label moieties, quenching moieties, synthesis handles and/or groups useful for, among other things, stabilizing oligonucleotide duplexes, such as, for example, agents that intercalate between base pairs (intercalating agents) and agent that bind the duplex minor groove (minor groove binding, or MGB, agents). The solid support, label moiety, synthesis handle and any optional additional moieties may be linked to one another in any fashion or orientation that permits them to perform their respective functions.

In some embodiments, the solid support is attached to the remainder of the reagent via a linker. Linkers attaching solid supports to the remainder of the reagent typically include linkages that are selectively cleavable under specified conditions such that, following synthesis, the synthesized labeled oligonucleotide can be released from the solid support. In some embodiments, the linkages are labile to the conditions used to deprotect the synthetic labeled oligonucleotide, such that the oligonucleotide is deprotected and cleaved from the solid support in a single step. Such linkers typically include ester linkages, but may include other linkages, such as, for example, carbonate esters, diisopropylsiloxy ethers, modified phosphates esters, etc.

Figure 6:
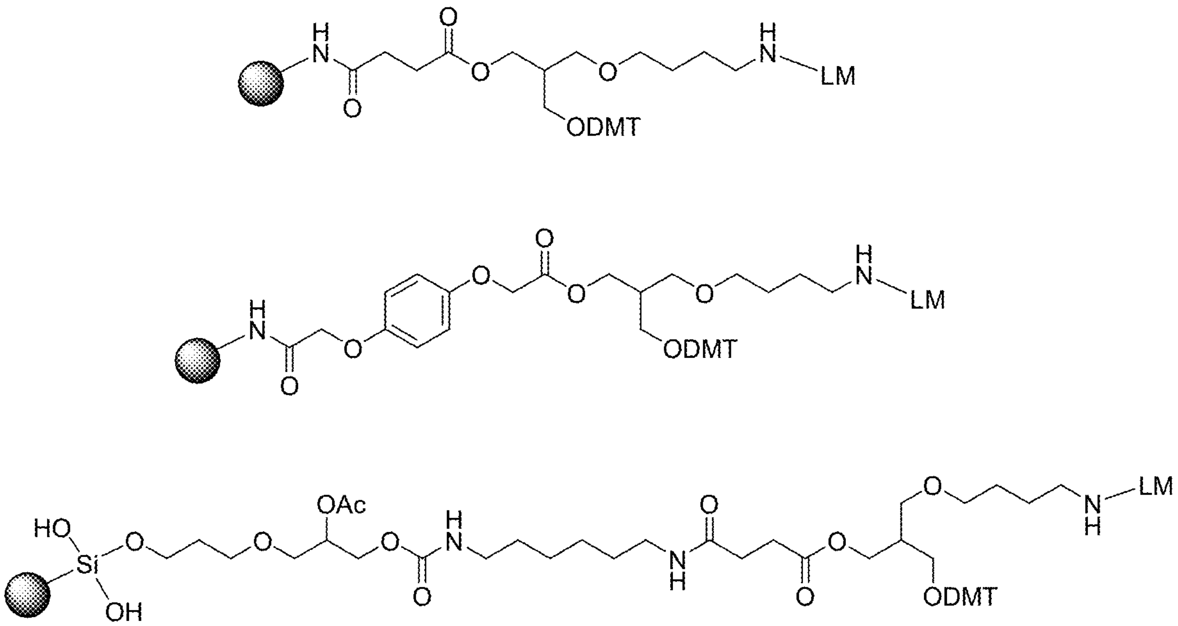

Myriad selectively cleavable linkers useful in the context of oligonucleotide synthesis are known in the art, as are methods of derivatizing solid supports with such linkers. All of these various linkers can be adapted for use in the solid support reagents described herein. Non limiting examples of solid support reagents comprising exemplary linkers that are cleavable under the basic conditions used to deprotect synthetic oligonucleotides are are illustrated in FIG. 6.

Like the synthesis reagents, the solid support reagents can be non-nucleosidic or nucleosidic in nature. Exemplary embodiments of non-nucleosidic solid support reagents include reagents according to structural formula (X):

(X)

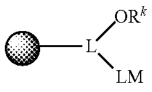

where LM represents the label moiety, L represents an optional selectively cleavable linker and —$OR^k$ represents the synthesis handle, where $R^k$ is an acid-labile protecting group, as previously described.

In some embodiments, the solid support synthesis reagents of structural formula (X) are non-nucleosidic reagents according to structural formula (X.1)

(X.1)

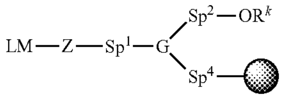

where Z, LM, G, $Sp^1$, $Sp^2$ and $R^k$ are as previously defined in connection with structural formula (IX.1) and $Sp^4$ represents a selectively cleavable spacing moiety. In some specific embodiments, selectively cleavable spacing moiety $Sp^4$ comprises an ester linkage.

In some embodiments, the solid support synthesis reagents of structural formula (X) are nucleosidic reagents according to structural formulae (X.2), (X.3), (X.4) or (X.5):

(X.2)

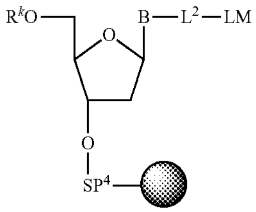

(X.3)

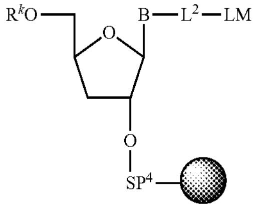

(X.4)

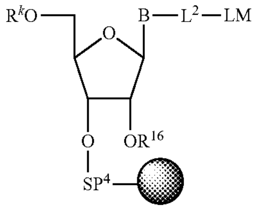

-continued (X.5)

Figure 7:
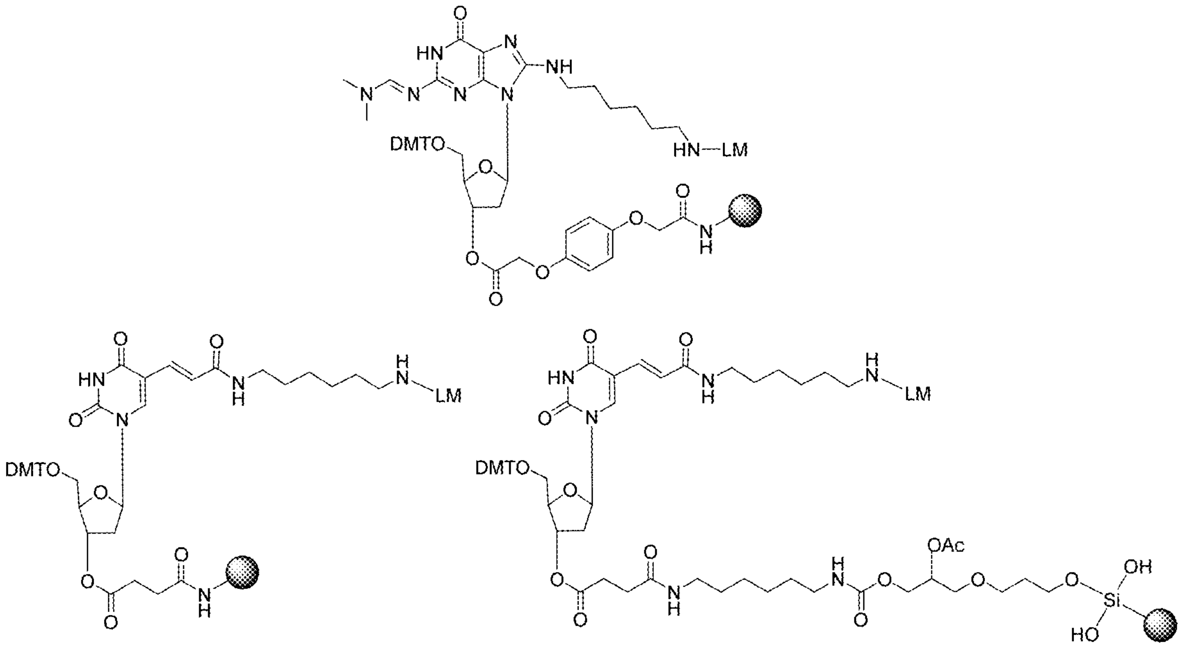

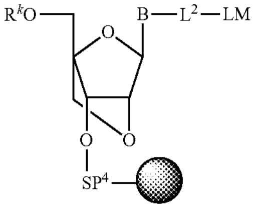

wherein LM, $R^k$, B, and $L^2$ are as previously defined for structural formulae (X.2), (X.3), (X.4) and/or (X.5), $R^{16}$ is as previously defined for structural formula (IX.4) and $Sp^4$ represents a selectively cleavable spacing moiety, as described above, which in some embodiments comprises an ester linkage. Specific examples of (X.2) are shown in FIG. 7.

4.11 Additional Exemplary Embodiments

It is to be understood that the specific embodiments of the various moieties, groups and linkers described throughout the disclosure can be included in all of the reagents described herein. Moreover, the various specific embodiments can be combined with one another in any combination as though the specific combination had been specifically exemplified. As a specific example, any one of the specific embodiments of label moiety LM described herein can be included in any of the specifically exemplified embodiments of non-nucleosidic and nucleosidic solid support and synthesis reagents described herein. As another specific example, any one of the specific embodiments of PEP group PEP, such as the phosphoramidite group of structural formula (P.1), supra, can be included in any of the synthesis reagents described herein.

4.12 Uses of the Reagents

The various reagents described herein can be used in the step-wise synthesis of oligonucleotides to synthesize oligonucleotides labeled with rhodamine dyes directly on the synthesis resin. Thus, the various reagents make available the ability to synthetically label oligonucleotides with myriad different rhodamines, obviating the need for laborious post-synthesis modifications. Using exemplary synthesis reagents to synthesize an oligonucleotide labeled with an NH rhodamine dye is illustrated in FIG. 8A.

As will be appreciated by skilled artisans, owing to the availability of phosphoramidite reagents that can act as donors, acceptors, or even quenchers for NH-rhodamine dyes, the reagents described herein permit the ability to synthesize oligonucleotides labeled with energy transfer dyes and/or NH-rhodamine-quencher dye pairs, that are synthesized in situ. Exemplary syntheses of oligonucleotides labeled with NH-rhodamine-fluorescein energy transfer dye pairs that illustrate the versatility provided by the reagents described herein are illustrated in FIGS. 8B and 9. Because the reagents described herein permit virtually any NH-rhodamine dye to be included in a solid support and/or synthesis reagent, oligonucleotides labeled with energy transfer dye pairs having spectral properties that are adjusted for specified applications can be conveniently synthesized in situ, without the need for post synthesis modification. Moreover, oligonucleotides labeled with myriad different energy transfer dye pair combinations can be synthesized from individual monomer reagents, obviating the need to make synthesis reagents containing specified dye pairs. Each member of the dye pair can be attached to the nascent oligonucleotide in a step-wise fashion, with or without the addition of intervening linking moieties.

Figure 8A:
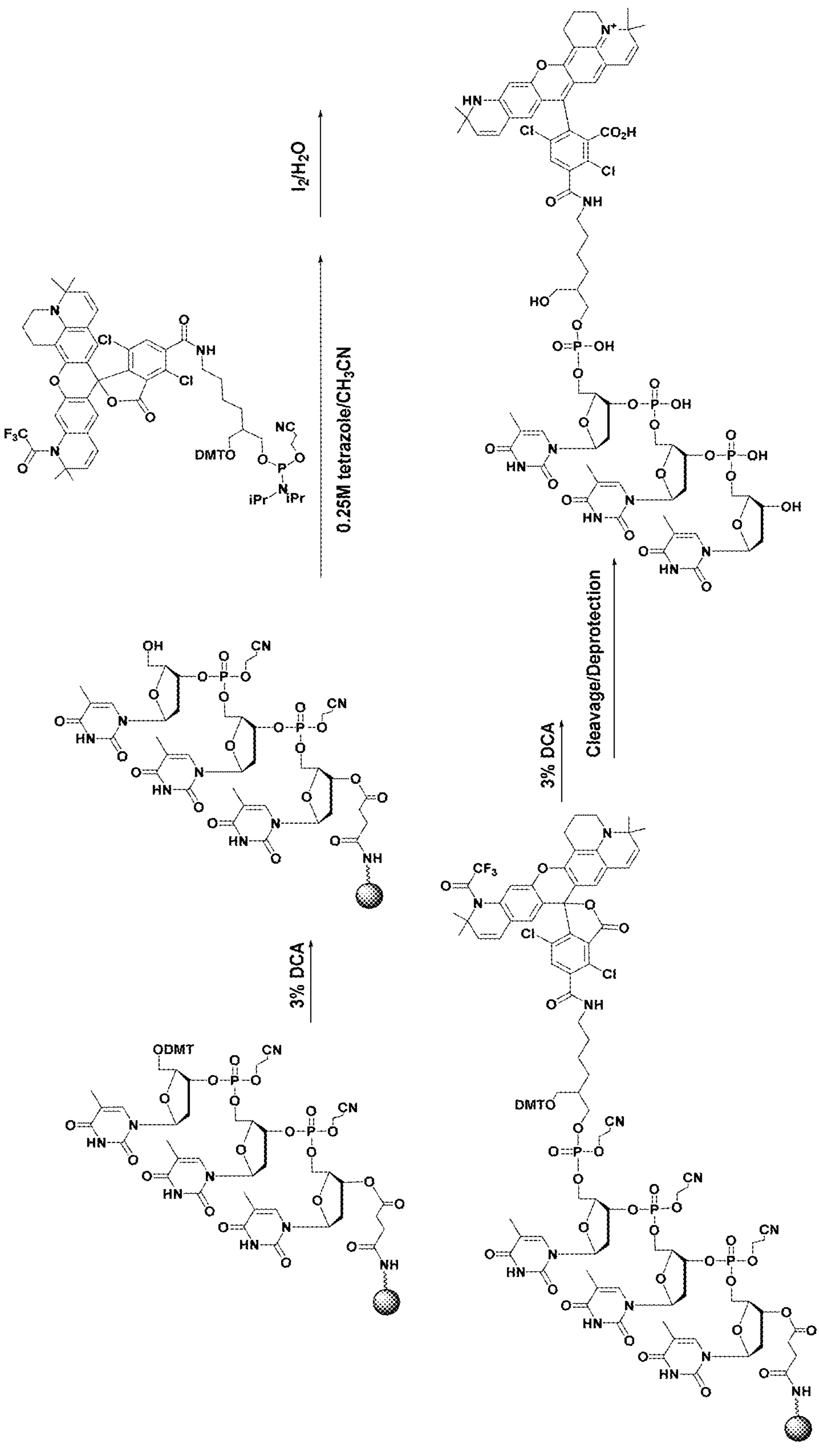
FIG. 8A illustrates the use of a specific embodiment of a synthesis reagent to synthesize an oligonucleotide labeled at its 5'-hydroxyl with an NH-rhodamine dye.
Figure 8B:
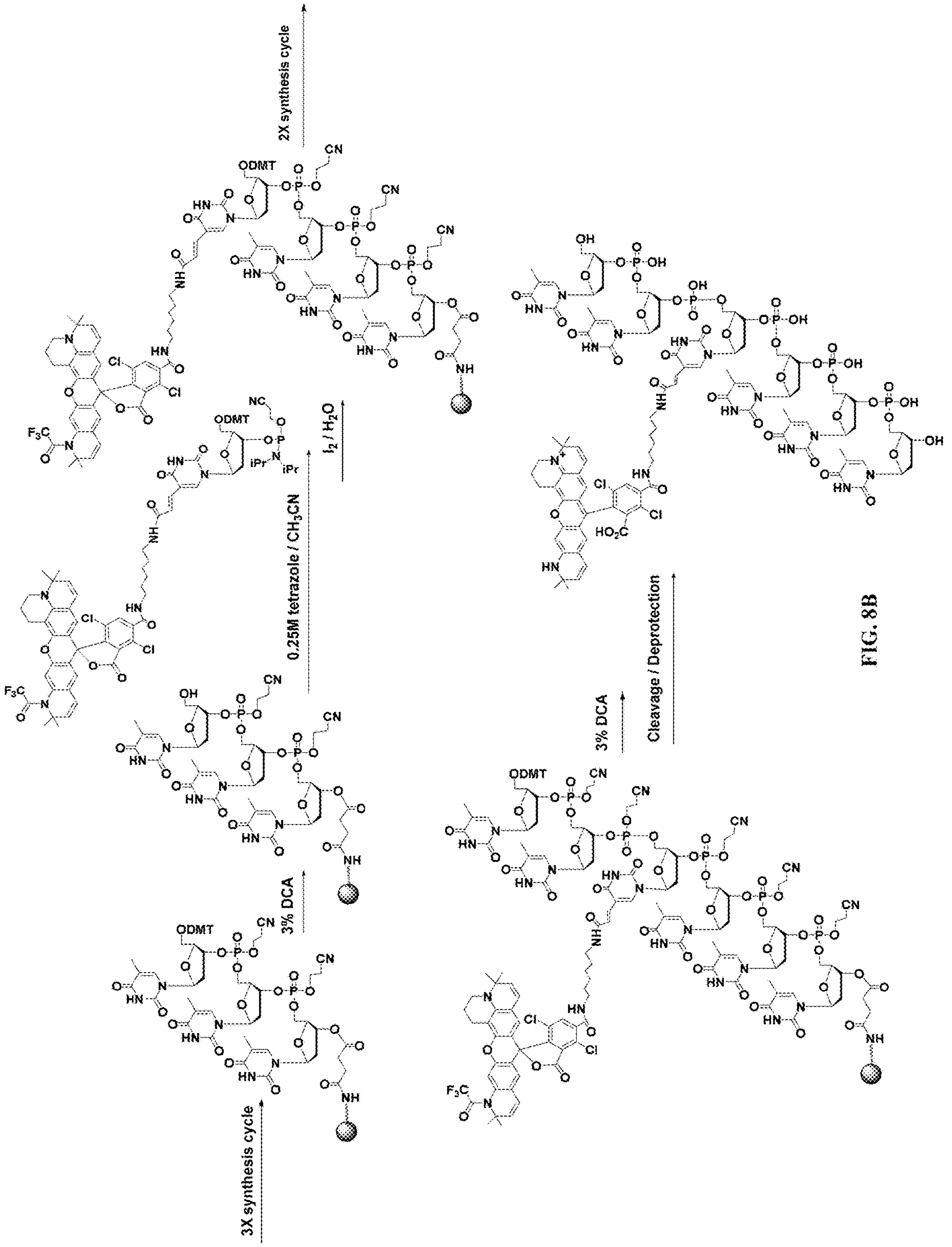
FIG. 8B illustrates the use of a linker phosphoramidite and a specific embodiment of a synthesis reagent to synthesize in situ an oligonucleotide labeled at its 5'-terminus with an energy transfer dye.
Figure 9:
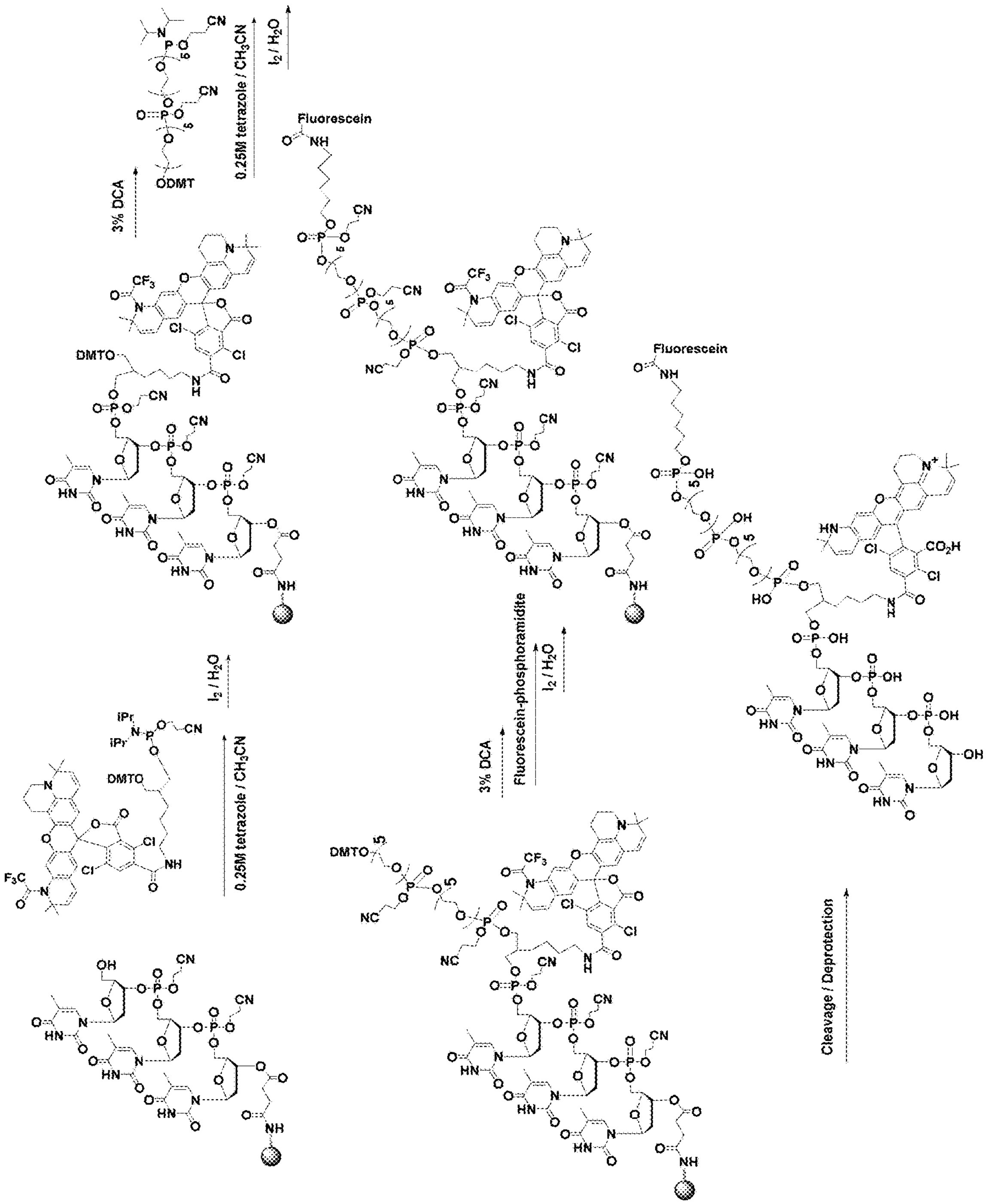
FIG. 9 illustrates the use of a specific embodiment of a synthesis reagent to synthesize an oligonucleotide labeled at its 3-hydroxyl with an energy-transfer dye.

Referring to FIG. 8A, support-bound synthetic oligonucleotide is treated with acid to remove the DMT group protecting its 5'-hydroxyl, yielding 5'-deprotected support-bound oligonucleotide. Coupling of N-protected NH-rhodamine phosphoramidite reagent followed by oxidation yields support-bound NH-rhodamine-labeled oligonucleotide in the lactone opened form. Treatment with concentrated ammonium hydroxide to remove any protecting groups and cleave the synthesized oligonucleotide from the solid support (resin) yields an oligonucleotide that is labeled with an NH-rhodamine dye.

Referring to FIG. 8B, nascent support-bound oligonucleotide can be labeled with an NH-rhodamine-fluorescein dye pair synthesized in situ by coupling N-protected NH-rhodamine phosphoramidite synthesis reagent to the 5'-hydroxyl of oligonucleotide, which, after oxidation, yields NH-rhodamine-labeled oligonucleotide. Removal of the DMT group followed by coupling with an O-protected phosphoramidite (which in the specific example illustrated is FAM-phosphoramidite) yields labeled, support-bound oligonucleotide. Cleavage and deprotection yields oligonucleotide, which is labeled with an NH-rhodamine-FAM energy transfer dye pair.

Referring to FIG. 9, solid support reagent, which includes a protected NH-rhodamine-fluorescein energy transfer dye pair as the label moiety, can undergo three cycles of synthesis to yield labeled support-bound oligonucleotide. Cleavage from the solid support yields deprotected, labeled oligonucleotide.

The length and character of the linkage linking the donor and acceptor dyes can also be manipulated through the use of phosphoramidite linker reagents. Coupling with FAM-phosphoramidite followed by oxidation, deprotection and cleavage yields an oligonucleotide, which is labeled with an NH-rhodamine-FAM energy transfer dye pair. In the linker phosphoramidite, "Sp" is a spacer, as previously defined. For example, "Sp" could represent ($Sp^1$), ($Sp^2$), ($Sp^3$), ($Sp^4$) or ($Sp^5$), as previously defined.

The length and properties of the linker linking the NH-rhodamine and FAM dyes can be adjusted by coupling additional linker phosphoramidites prior to coupling with the FAM-phosphoramidite. The linker phosphosphoramites could be the same, or they could be different. In this way, oligonucleotides labeled with energy transfer dye pairs in which the donor and acceptor dyes, as well as the linker linking the donor and acceptors, are tailored for specific purposes can be readily synthesized in situ.

Skilled artisan will appreciate that any N-protected NH-rhodamine reagent that acts as an acceptor for FAM could be used. Moreover, other O-protected fluoresceins could be used, as could other types of phosphormidite dyes. Because the dyes are added as monomers, the number of energy transfer dye labels available is greater than the number of phosphoramidite reagents necessary to synthesize them. For example, oligonucleotides labeled with 9 different energy-transfer dye pairs can be synthesized from 3 different N-protected NH-rhodamine phosphoramidite reagents (reagents A, B and C) and 3 different O-protected fluorescein phosphoramidite reagents (reagents 1, 2 and 3): oligo-A1, oligo-A2, oligo-A3, oligo-B1, oligo-B2, oligo-B3, oligo-C1, oligo-C2 and oligo-C3.

Current analyses of cell and tissue functionality often require extracting as much information as possible from materials that are often limited. For example, samples such as tumor biopsies are difficult to collect and usually yield only a small amount of usable nucleic acid. PCR detection and measurement of a single target analyte, referred to as a singleplex assay, has been the gold standard for analyzing clinical research samples on the nucleic acid level, and has been invaluable in extending the limits of biological knowledge for more than a quarter century.

However, the limited amount of nucleic acid obtained from clinical research specimens often forces choices to be made about how best to utilize these precious samples. Furthermore, if the sample is limited, the number of loci that can be analyzed is also limited, reducing the amount of information that can be extracted from the sample. Finally, the additional time and materials required to set up multiple single-assay reactions could increase the expense of a complex project significantly.

Multiplex PCR analysis of nucleic acids, a strategy where more than one target is amplified and quantified from a single sample aliquot, is an attractive solution to these problems. In multiplex PCR, a sample aliquot is queried with multiple probes that contain fluorescent dyes in a single PCR reaction. This increases the amount of information that can be extracted from that sample. With multiplex PCR, significant savings in sample and materials can be realized. To increase the utility of this method, multiplexed PCR using several pairs of gene-specific primers and probes to amplify and measure multiple target sequences simultaneously has been developed. Multiplexing PCR provides the following advantages: 1) Efficiency: multiplexed PCR helps conserve sample material and avoid well-to-well variation by combining several PCR assays into a single reaction. Multiplexing makes more efficient use of limited samples, such as those harboring a rare target that cannot be split into multiple aliquots without compromising the sensitivity; 2) Economy: even though the targets are amplified in unison, each one is detected independently by using a gene-specific probe with a unique reporter dye to distinguish the amplifications based on their fluorescent signal. Once optimized, a multiplexed assay is more cost effective than the same assays amplified independently.

However, currently there are limitations to the number of targets that can be analyzed in a single multiplex PCR assay. The experimental design for multiplex PCR is more complicated than for single reactions. The probes used to detect individual targets must contain unique reporter dyes with distinct spectra. The settings for excitation and emission filters of real-time detection systems vary from manufacturer to manufacturer; therefore, instruments must be calibrated for each dye as part of the experiment optimization process. Thus, one limitation in the development of multiplex PCR assays is the number of fluorophores, and hence probes, that can be effectively measured in a single reaction. For example, in multiplexed PCR, signal crosstalk between different fluorescence reporters can compromise quantification or cause false positives. It is therefore essential to select fluorophores with minimal spectral overlap. Additionally, the fluorophores, and specifically, their emission and excitation spectra, must also be compatible with the PCR instrument to be used, and specifically, the band-pass specifications for each filter-set.

In a further aspect, methods of performing singleplex or multiplex PCR, such as qPCR or end-point PCR, using the described probes are provided. End point PCR is the analysis after all cycles of PCR are completed. Unlike qPCR, which allows quantification as template is doubling (exponential phase), end point analysis is based on the plateau phase of amplification.

In particular, a method for amplifying and detecting multiple target DNA sequences comprising providing a composition or reaction mixture comprising the described probe, subjecting the reaction mixture to a thermocycling protocol such that amplification of said multiple target sequences can take place, and monitoring amplification by detecting the fluorescence of the described probe at least once during a plurality of amplification cycles.

The nucleic acid target(s) of the described method may be any nucleic acid target known to the skilled artisan. Further, the targets may be regions of low mutation or regions of high mutation. For example, one particularly valuable use of the methods disclosed herein involves targeting highly mutated nucleic acids, such as RNA viral genes, or regions of high genetic variability, such a single nucleotide polymorphisms (SNPs). In some embodiments, the targets may be fragmented or degraded, such as material from forensic samples and/or fixed tissues. The targets may be any size amenable to amplification. One particularly valuable use of the methods and compositions provided herein involves the identification of short fragments, such as siRNA and miRNA. Another particularly valuable use is for samples that may have fragmented and/or degraded nucleic acid, such as fixed samples or samples that have been exposed to the environment. Thus, the methods may be used for biopsy tissue and forensic DNA for example. The targets may be purified or unpurified. The targets may be produced in vitro (for example, a cDNA target) or can be found in biological samples (for example, an RNA or a genomic DNA (gDNA) target). The biological sample may be used without treatment or the biological samples may be treated to remove substances that may interfere with the methods disclosed herein.

The probes provided herein may be used in methods of diagnosis, e.g., SNP detection, identification of specific biomarkers, etc., whereby the probes are complementary to a sequence (e.g., genomic) of an infectious disease agent, e.g., of human disease including but not limited to viruses, bacteria, parasites, and fungi, thereby diagnosing the presence of the infectious agent in a sample having nucleic acid from a patient. The target nucleic acid may be genomic or cDNA or mRNA or synthetic, human or animal, or of a microorganisms, etc. In other embodiments, the probes may be used to diagnose or prognose a disease or disorder that is not caused by an infectious agent. For example, the probes may be used to diagnose or prognose cancer, autoimmune diseases, mental illness, genetic disorders, etc. by identifying the presence of a mutation, polymorphism, or allele in a sample from a human or animal. In some embodiments, the probe comprises the mutation or polymorphism. Additionally, the probes may be used to evaluate or track progression of treatment for a disease or disorder.

Another area that benefits from multiplex analysis is the use of genetic markers in the field of human identification. Genetic markers are generally a set of polymorphic loci having alleles in genomic DNA with characteristics of interest for analysis, such as DNA typing, in which individuals are differentiated based on variations in their DNA. Most DNA typing methods are designed to detect and analyze differences in the length and/or sequence of one or more regions of DNA markers known to appear in at least two different forms, or alleles, in a population. Such variation is referred to as "polymorphism," and any region of DNA in which such a variation occurs is referred to as a "polymorphic locus." One possible method of performing DNA typing involves the joining of PCR amplification technology (KB Mullis, U.S. Pat. No. 4,683,202) with the analysis of length variation polymorphisms. Short tandem repeats (STRs), minisatellites and variable number of tandem repeats (VNTRs) are some examples of length variation polymorphisms. STRs, containing repeat units of approximately three to seven nucleotides, are short enough to be useful as genetic markers in PCR applications, because amplification protocols can be designed to produce smaller products than are possible from the other variable length regions of DNA.

Several such systems containing multiple STR loci have been described. See, e.g., AMPFLSTR® SGMPLUS™ PCRAMPLIFICATION KIT USER'S MANUAL, Applied Biosystems, pp. i-x and 1-1 to 1-16 (2001); AMPFLSTR® IDENTIFILER® PCR AMPLIFICATION KIT USER'S MANUAL, Applied Biosystems, pp. i-x and 1-1 to 1-10 (2001); J W Schumm et al., U.S. Pat. No. 7,008,771.

The methods of the present teachings contemplate selecting an appropriate set of loci, primers, and amplification protocols to generate amplified alleles (amplicons) from multiple co-amplified loci, which amplicons can be designed so as not to overlap in size, and/or can be labeled in such a way as to enable one to differentiate between alleles from different loci which do overlap in size. In addition, these methods contemplate the selection of multiple STR loci which are compatible for use within a single amplification protocol.

Successful combinations in addition to those disclosed herein can be generated by, for example, trial and error of locus combinations, by selection of primer pair sequences, and by adjustment of primer concentrations to identify an equilibrium in which all loci for analysis can be amplified. Once the methods and materials of these teachings are disclosed, various methods of selecting loci, primer pairs, and amplification techniques for use in the methods and kits of these teachings are likely to be suggested to one skilled in the art. All such methods are intended to be within the scope of the appended claims.

Any of a number of different techniques can be used to select the set of loci for use according to the present teachings. Regardless of what methods may be used to select the loci analyzed by the methods of the present teaching, the loci selected for multiplex analysis in various embodiments share one or more of the following characteristics: (1) they produce sufficient amplification products to allow allelic evaluation of the DNA; (2) they generate few, if any, artifacts during the multiplex amplification step due to incorporation of additional bases during the extension of a valid target locus or the production of non-specific amplicons; and (3) they generate few, if any, artifacts due to premature termination of amplification reactions by a polymerase. See, e.g., J W Schumm et al. (1993), FOURTH INTERNATIONAL SYMPOSIUM ON HUMAN IDENTIFICATION, pp. 177-187, Promega Corp.

Generally, oligonucleotide primers can be chemically synthesized. Primer design and selection is a routine procedure in PCR optimization. One of ordinary skill in the art can easily design specific primers to amplify a target locus of interest, or obtain primer sets from the references listed herein. All of these primers are within the scope of the present teachings.

As an example, primers can be selected by the use of any of various software programs available and known in the art for developing amplification and/or multiplex systems. See, e.g., Primer Express® software (Applied Biosystems, Foster City, Calif.). In the example of the use of software programs, sequence information from the region of the locus of interest can be imported into the software. The software then uses various algorithms to select primers that best meet the user's specifications.

Samples of genomic DNA can be prepared for use in the methods of the present teaching using any procedures for sample preparation that are compatible with the subsequent amplification of DNA. Many such procedures are known by those skilled in the art. Some examples are DNA purification by phenol extraction (J. Sambrook et al. (1989), in MOLECULAR CLONING: A LABORATORY MANUAL, SECOND EDITION, Cold Spring Harbor Laboratory Press, Cold Spring Harbor, N.Y., pp. 9.14-9.19), and partial purification by salt precipitation (S. Miller et al. (1988), NUCL. ACIDS REs. 16:1215) or chelex (P S Walsh et al. (1991), BIOTECHNIQUES 10:506-513; C T Corney et al. (I 994), J. FORENSIC Ser. 39: 1254) and the release of unpurified material using untreated blood (J. Burckhardt (1994), PCR METHODS AND APPLICATIONS 3:239-243; RBE McCabe (1991), PCR METHODS AND APPLICATIONS 1:99-106; BY Nordvag (1992), BIOTECHNIQUES 12:4 pp. 490-492).

When the at least one DNA sample to be analyzed using the methods of this teaching is human genomic DNA, the DNA can be prepared from tissue samples such as, for example, one or more of blood, semen, vaginal cells, hair, saliva, urine, bone, buccal samples, amniotic fluid containing placental cells or fetal cells, chorionic villus, and/or mixtures of any of these or other tissues.

Samples containing blood or buccal samples can also be processed directly from FTA® paper (Whatman Inc., Piscataway, NJ), Bode Buccal Collector, or swabs. Examples of swabs include but are not limited to, Copan 4N6 Forensic Flocked Swab (Copan, P/N 3520CS01, Murrieta, CA), Omi Swab (Whatman Inc., P/N 10005) and Puritan Cotton Swab (Puritan, P/N 25-806 1WC EC, various medical suppliers).

Once a sample of genomic DNA is prepared, the target loci can be co-amplified in the multiplex amplification step of the present teaching. Any of a number of different amplification methods can be used to amplify the loci, such as, for example, PCR (R K Saiki et al. (1985), SCIENCE 230: 1350-1354), transcription based amplification (DY Kwoh and T J Kwoh (1990), AMERICAN BIOTECHNOLOGY LABORATORY, October, 1990) and strand displacement amplification (SDA) (GT Walker et al. (1992), PROC. NATL. ACAD. Ser., U.S.A. 89: 392-396). In some embodiments of the present teaching, multiplex amplification can be effected via PCR, in which the DNA sample is subjected to amplification using primer pairs specific to each locus in the multiplex. The chemical components of a standard PCR generally comprise a solvent, DNA polymerase, deoxyribonucleoside triphosphates ("dNTPs"), oligonucleotide primers, a divalent metal ion, and a DNA sample expected to contain the target(s) for PCR amplification. Water can generally be used as the solvent for PCR, typically comprising a buffering agent and non•buffering salts such as KCL The buffering agent can be any buffer known in the art, such as, but not limited to, Tris-HCl, and can be varied by routine experimentation to optimize PCR results. Persons of ordinary skill in the art are readily able to determine optimal buffering conditions. PCR buffers can be optimized depending on the particular enzyme used for amplification.

The enzyme that polymerizes the nucleotide triphosphates into the amplified products in PCR can be any DNA polymerase. The DNA polymerase can be, for example, any heat-resistant polymerase known in the art. Examples of some polymerases that can be used in this teaching are DNA polymerases from organisms such as *Thermus aquaticus, Thermus thermophilus, Thermococcus litoralis, Bacillus stearothermophilus, Thermotoga maritima* and *Pyrococcus* sp. The enzyme can be acquired by any of several possible methods; for example, isolated from the source bacteria, produced by recombinant DNA technology or purchased from commercial sources. Some examples of such commercially available DNA polymerases include AmpliTaq Gold® DNA polymerase; AmpliTaq® DNA Polymerase; AmpliTaq® DNA Polymerase Stoffel Fragment; rTth DNA Polymerase; and rTth DNA Polymerase, XL (all manufactured by Applied Biosystems, Foster City, Calif.). Other examples of suitable polymerases include Tne, Bst DNA polymerase large fragment from *Bacillus stearothermophilus*, Vent and Vent Exo− from *Thermococcus litoralis*, Tma from *Thermotoga maritima*, Deep Vent and Deep Vent Exo- and Pfu from *Pyrococcus* sp., and mutants, variants and derivatives of the foregoing.

Where fluorescent labeling of primers is used in a multiplex reaction, generally at least three different labels can be used to label the different primers. When a size marker is used to evaluate the products of the multiplex reaction, the primers used to prepare the size marker may be labeled with a different label from the primers that amplify the loci of interest in the reaction. With the advent of automated fluorescent imaging and analysis, faster detection and analysis of multiplex amplification products can be achieved.

In some embodiments of the present teaching, a fluorophore can be used to label at least one primer of the multiplex amplification, e.g., by being covalently bound to the primer, thus creating a fluorescent labeled primer. In some embodiments, primers for different target loci in a multiplex can be labeled with different fluorophores, each fluorophore producing a different colored product depending on the emission wavelength of the fluorophore. These variously labeled primers can be used in the same multiplex reaction, and their respective amplification products subsequently analyzed together. Either the forward or reverse primer of the pair that amplifies a specific locus can be labeled, although the forward may more often be labeled.

The PCR products can be analyzed on a sieving or non-sieving medium. In some embodiments of these teachings, for example, the PCR products can be analyzed by electrophoresis; e.g., capillary electrophoresis, as described in H. Wenz et al. (1998), GENOME REs. 8:69-80 (see also E. Buel et al. (1998), J. FORENSIC SCI. 43:(1), pp. 164-170)), or slab gel electrophoresis, as described in M. Christensen et al. (1999), SCAND. J. CLIN. LAB. INVEST. 59(3): 167-177, or denaturing polyacrylamide gel electrophoresis (see, e.g., J. Sambrook et al. (1989), in MOLECULAR CLONING: A LABORATORY MANUAL, SECOND EDITION, Cold Spring Harbor Laboratory Press, Cold Spring Harbor, N.Y., pp. 13.45-13.57). The separation of DNA fragments in electrophoresis is based primarily on differential fragment size. Amplification products can also be analyzed by chromatography; e.g., by size exclusion chromatography (SEC).

Once the amplified alleles are separated, these alleles and any other DNA in, for example, the gel or capillary (e.g., a DNA size markers or an allelic ladder) can then be visualized and analyzed. Oftentimes, the method for detection of multiplex loci can be by fluorescence. See, e.g., J W Schumm et al. in PROCEEDINGS FROM THE EIGHTH INTERNATIONAL SYMPOSIUM ON HUMAN IDENTIFICATION, pub. 1998 by Promega Corporation, pp. 78-84; E. Buel et al. (1998), supra. Where fluorescent-labeled primers are used for detecting each locus in the multiplex reaction, amplification can be followed by detection of the labeled products employing a fluorometric detector.

The size of the alleles present at each locus in the DNA sample can be determined by comparison to a size standard in electrophoresis, such as a DNA marker of known size. Markers for evaluation of a multiplex amplification containing two or more polymorphic STR loci may also comprise a locus-specific allelic ladder or a combination of allelic ladders for each of the loci being evaluated. See, e.g., C. Puers et al. (1993), AM. J. HUM. GENET. 53:953-958; C. Puers et al. (1994), GENOMICS 23:260-264. See also, U.S. Pat. Nos. 5,599,666; 5,674,686; and 5,783,406 for descriptions of some allelic ladders suitable for use in the detection of STR loci, and some methods of ladder construction disclosed therein. Following the construction of allelic ladders for individual loci, the ladders can be electrophoresed at the same time as the amplification products. Each allelic ladder co-migrates with the alleles from the corresponding locus.

The products of the multiplex reactions of the present teachings can also be evaluated using an internal lane standard; i.e., a specialized type of size marker configured to be electrophoresed, for example, in the same capillary as the amplification products. The internal lane standard can comprise a series of fragments of known length. The internal lane standard can also be labeled with a fluorescent dye, which is distinguishable from other dyes in the amplification reaction. The lane standard can be mixed with amplified sample or size standards/allelic ladders and electrophoresed with either, in order to compare migration in different lanes of gel electrophoresis or different capillaries of capillary electrophoresis. Variation in the migration of the internal lane standard can serve to indicate variation in the performance of the separation medium. Quantitation of this difference and correlation with the allelic ladders can provide for calibration of amplification product electrophoresed in different lanes or capillaries, and correction in the size determination of alleles in unknown samples.

Where fluorescent dyes are used to label amplification products, the electrophoresed and separated products can be analyzed using fluorescence detection equipment such as, for example, the ABI PRISM® 310 or 3 130xl genetic analyzer, or an ABI PRISM® 37 DNA Sequencer (Applied Biosystems, Foster City, Calif.); or a Hitachi FMBIO™ II Fluorescent Scanner (Hitachi Software Engineering America, Ltd., South San Francisco, Calif.). In various embodiments of the present teachings, PCR products can be analyzed by a capillary gel electrophoresis protocol in conjunction with such electrophoresis instrumentation as the ABI PRISM® 3130xl genetic analyzer (Applied Biosystems), and allelic analysis of the electrophoresed amplification products can be performed, for example, with GeneMapper® ID Software v3.2, from Applied Biosystems. In other embodiments, the amplification products can be separated by electrophoresis in, for example, about a 4.5%, 29: 1 acrylamide:bis acrylamide, 8 M urea gel as prepared for an ABI PRISM® 377 Automated Fluorescence DNA Sequencer.

The present teachings are also directed to kits that utilize the processes described above. In some embodiments, a basic kit can comprise a container having one or more locus•specific primers. A kit can also optionally comprise instructions for use. A kit can also comprise other optional kit components, such as, for example, one or more of an allelic ladder directed to each of the specified loci, a sufficient quantity of enzyme for amplification, amplification buffer to facilitate the amplification, divalent cation solution to facilitate enzyme activity, dNTPs for strand extension during amplification, loading solution for preparation of the amplified material for electrophoresis, genomic DNA as a template control, a size marker to insure that materials migrate as anticipated in the separation medium, and a protocol and manual to educate the user and limit error in use. The amounts of the various reagents in the kits also can be varied depending upon a number of factors, such as the optimum sensitivity of the process. It is within the scope of these teachings to provide test kits for use in manual applications or test kits for use with automated detectors or analyzers.

In a clinical setting, STR markers can be used, for example, to monitor the degree of donor engraftment in bone marrow transplants. In hospitals, these markers can also be useful in specimen matching and tracking. These markers have also entered other fields of science, such as population biology studies on human racial and ethnic group differences (DB Goldstein et al. (1995), PROC. NATL. ACAD. Ser. U.S.A. 92:6723-6727), evolution and species divergence, and variation in animal and plant taxa (MW Bruford et al. (1993), CURR. BIOL. 3:939-943).

Amplification of mini-STRs (loci of fewer than approximately 200 base pairs) allows for the profiling analysis of highly degraded DNA, as is demonstrated in MD Coble (2005), J. FORENSIC SCI. 50(1):43-53, which is incorporated by reference herein. Table 1 (see U.S. Patent Application No. 61/413,946, filed Nov. 15, 2010 and Patent Application No. 61/526,195, filed Aug. 22, 2011 for Table 1) also provides loci that can be considered mini-STR loci depending on the positioning of the primers used to amplify the STR marker within a primer amplification set.

DNA concentrations can be measured prior to use in the method of the present teaching, using any standard method of DNA quantification known to those skilled in the art. Such quantification methods include, for example, spectrophotometric measurement, as described by J. Sambrook et al. (1989), supra, Appendix E.5; or fluorometric methodology using a measurement technique such as that described by C F Brunk et al. (1979), ANAL. BIOCHEM. 92: 497-500. DNA concentration can be measured by comparison of the amount of hybridization of DNA standards with a human-specific probe such as that described by J S Waye et al. (1991), J. FORENSIC SCI. 36:1198-1203 (1991). Use of too much template DNA in the amplification reactions may produce amplification artifacts, which would not represent true alleles.

Where fluorescent labeling of primers is used in a multiplex reaction, generally at least three different labels, at least four different labels, at least five different labels, at least six different labels are used. For example, existing commercial assays utilize 6 unique dye labels (VeriFiler™ Plus PCR Amplification Kit, Thermo Fisher Scientific). Instruments used for the analysis of multiplex fluorescent dye based reactions are limited in the wavelengths of light they can emit to excite the fluorescent dyes and limited in in the wavelengths of light emitted from the dyes that they can detect. In order to design a multiplex assay using at least 8 labels, at least 10 labels or at least 16 labels there needs to be a range of dyes that have unique spectral emission properties such that their peak emission peaks are well resolved from each other with little to no overlap. In addition the fluorescent dye labels must all be detectable on an instrument capable of producing a specific set of excitation wavelengths and with a specific range of detectable emission wavelengths. The class of rhodamine derivatives described herein provides for dy labels with unique spectral properties that are not available with existing dye compounds and therefore opens up the possibility to increase the number of fluorescent dye labels used in multiplex reactions with up to 8, 10, 12, 16 or more different labels using existing laser technology commonly used for current multiplex assays. It is envisioned that with improvements in instrumental capabilities, multiplex assays implementing more than 8 labels (e.g., at least 10, at least 12, or at least 16 different labels) could be used to label the different primers. When a size marker is used to evaluate the products of the multiplex reaction, the primers used to prepare the size marker may be labeled with a different label from the primers that amplify the loci of interest in the reaction. With the advent of automated fluorescent imaging and analysis, faster detection and analysis of multiplex amplification products can be achieved.

The following are some examples of possible fluorophores well known in the art and suitable for use in combination with the compounds described in the present teachings to provide assays using multiple fluorescent labels. The list is intended to be exemplary and is by no means exhaustive. Some possible fluorophores include: fluorescein (FL), which absorbs maximally at 492 nm and emits maximally at 520 nm; N,N,N',N'-tetramethyl-6-carboxyrhodamine (TAMRA™), which absorbs maximally at 555 nm and emits maximally at 580 nm; 5-carboxyfluorescein (5-FAM™), which absorbs maximally at 495 nm and emits maximally at 525 nm; 2',7'-dimethoxy-4',5'-dichloro-6-carboxyfluorescein (JOE™), which absorbs maximally at 525 nm and emits maximally at 555 nm); 6-carboxy-X-rhodamine (ROX™), which absorbs maximally at 585 nm and emits maximally at 605 nm; CY3™ which absorbs maximally at 552 nm and emits maximally at 570 nm; CY5™, which absorbs maximally at 643 nm and emits maximally at 667 nm; tetrachloro-fluorescein (TET™) which absorbs maximally at 521 nm and emits maximally at 536 nm; and hexachloro-fluorescein (HEX™), which absorbs maximally at 535 nm and emits maximally at 556 nm; NED™ which absorbs maximally at 546 nm and emits maximally at 575 nm; 6-FAM™ which emits maximally at approximately 520 nm; VIC® which emits maximally at approximately 550 nm; PET® which emits maximally at approximately 590 nm; and LIZ™ which emits maximally at approximately 650 nm. See S R Coticone et al., U.S. Pat. No. 6,780,588; AMPFLSTR® IDENTIFILER™ PCR AMPLIFICATION KIT USER'S MANUAL, pp. 1-3, Applied Biosystems (2001). Note that the above listed emission and/or absorption wavelengths are typical and can be used for general guidance purposes only; actual peak wavelengths may vary for different applications and under different conditions. Additional fluorophores can be selected for the desired absorbance and emission spectra as well as color as is known to one of skill in the art and are provided below:

TABLE 3

Commercially Available Dyes

| Fluorophore | Abs (nm) | Em (nm) | Fluorophore | Abs (nm) | Em (nm) |
|---|---|---|---|---|---|
| Methoxycoumarin | 340 | 405 | Dansyl | 340 | 520 |
| Pyrene | 345 | 378 | Alexa Fluor ® 350 | 346 | 442 |
| CF ™ 350 | 347 | 448 | AMCA | 349 | 448 |
| DyLight 350 | 353 | 432 | Marina Blue ® dye | 365 | 460 |
| Dapoxyl ® dye | 373 | 551 | Dialkylamino-coumarin | 375 435 | 470- 475 |

TABLE 3-continued

Commercially Available Dyes

| Fluorophore | Abs (nm) | Em (nm) | Fluorophore | Abs (nm) | Em (nm) |
|---|---|---|---|---|---|
| Bimane | 380 | 458 | SeTau 380 | 381 | 480 |
| Hydroxycoumarin | 385 | 445 | ATTO 390 | 390 | 479 |
| Cascade Blue ® dye | 400 | 420 | Pacific Orange ® dye | 400 | 551 |
| DyLight ® 405 | 400 | 420 | Alexa Fluor ® 405 | 402 | 421 |
| SeTau 404 | 402 | 518 | Cascade Yellow ® dye | 402 | 545 |
| CF ™ 405S | 404 | 431 | CF ™ 405M | 408 | 452 |
| Pacific Blue ™ dye | 410 | 455 | PyMPO | 415 | 570 |
| DY-415 | 415 | 467 | SeTau 425 | 425 | 545 |
| Alexa Fluor ® 430 | 434 | 539 | ATTO 425 | 436 | 484 |
| ATTO 465 | 453 | 508 | NBD | 465 | 535 |
| Seta 470 | 409 | 521 | CF ™ 485 | 470-488 | 513 |
| DY-485XL | 485 | 560 | CF ™ 488A | 490 | 515 |
| DyLight ® 488 | 493 | 518 | DY 496 | 493 | 521 |
| Fluorescein | 494 | 518 | ATTO 495 | 495 | 527 |
| Alexa Fluor ® 488 | 495 | 519 | Oregon Green ® 488 | 496 | 524 |
| BODIPY ® 493/503 | 500 | 506 | CAL Fluor ® Green 520 | 500 | 522 |
| DY-480XL | 500 | 630 | ATTO 488 | 501 | 523 |
| Rhedamine Green dye | 502 | 527 | BODIPY ® FL | 505 | 513 |
| DY 505 | 505 | 530 | DY 510XL | 509 | 590 |
| 2',7'-Dichlorofluorescein | 510 | 532 | Oregon Green ® 514 | 511 | 530 |
| DY-481XL | 515 | 650 | ATTO 520 | 516 | 538 |
| Alexa Fluor ® 514 | 518 | 540 | CAL Fluor ® Gold 540 | 519 | 337 |
| DY 520XL | 520 | 644 | 4',5'-Dichlor-2',7'-dimethoxy-fluorescein (JOE) | 522 | 550 |
| DY-521XL | 523 | 668 | Eosin | 524 | 544 |
| Rhodamine 6G | 525 | 555 | BODIPY ® R6G | 528 | 550 |
| Alexa Fluor ® 532 | 531 | 554 | ATTO 532 | 532 | 553 |
| BODIPY ® 530/550 | 534 | 554 | CAL Fluor ® Orange 560 | 534 | 556 |
| DY-530 | 539 | 561 | BODIPY ® TMR | 542 | 574 |
| DY-555 | 547 | 572 | DY556 | 548 | 573 |
| Quasar ® 570 | 548 | 570 | Cy 3 | 550 | 570 |
| CF ™ 555 | 550 | 570 | DY-554 | 551 | 572 |
| DY 550 | 553 | 578 | ATTO 550 | 554 | 576 |
| Tetramethyl-rhodamine (TMR) | 555 | 580 | Alexa Fluor ® 555 | 555 | 565 |
| Seta 555 | 556 | 570 | Alexa Fluor ® 546 | 556 | 575 |
| DY-547 | 557 | 574 | DY-548 | 558 | 572 |
| BODIPY ® 558/568 | 558 | 569 | DY-560 | 559 | 578 |
| DY 549 | 560 | 575 | DyLight ® 549 | 562 | 618 |
| CF ™ 568 | 562 | 583 | ATTO 565 | 563 | 592 |
| BODIPY ® 564/570 | 565 | 571 | CAL Fluor ® Red 590 | 566 | 588 |
| Lissamine rhodamine B | 570 | 590 | Rhodamine Red dye | 570 | 590 |
| BODIPY ® 576/589 | 576 | 590 | Alexa Fluor ® 568 | 578 | 603 |
| X-rhodamine | 580 | 605 | DY-590 | 580 | 599 |
| BODIPY ® 581/591 | 584 | 592 | CAL Fluor ® Red 610 | 587 | 608 |
| BODIPY ® TR | 589 | 617 | Alexa Fluor ® 594 | 590 | 617 |
| ATTO 590 | 594 | 624 | CF ™ 594 | 594 | 614 |
| CAL Fluor ® Red 615 | 595 | 615 | Texas Red ® dye | 595 | 615 |
| Naphthofluorescein | 605 | 675 | DY-682 | 609 | 709 |
| DY-610 | 610 | 630 | CAL Fluor ® Red 635 | 611 | 631 |
| ATTO 611x | 611 | 681 | Alexa Fluor ® 610 | 612 | 628 |
| ATTO 610 | 615 | 634 | CF ™ 620R | 617 | 639 |
| ATTO 620 | 619 | 643 | DY-615 | 621 | 641 |
| BODIPY ® 630/650 | 625 | 640 | ATTO 633 | 629 | 657 |
| CF ™ 633 | 630 | 650 | Seta 632 | 632 | 641 |
| Alexa Fluor ® 633 | 632 | 647 | Alesa Fluor ® 635 | 633 | 647 |
| DY-634 | 635 | 658 | Seta 633 | 637 | 647 |

TABLE 3-continued

| Commercially Available Dyes | | | | | |
|---|---|---|---|---|---|
| Fluorophore | Abs (nm) | Em (nm) | Fluorophore | Abs (nm) | Em (nm) |
| DY-630 | 636 | 657 | DY-633 | 637 | 657 |
| DY-632 | 637 | 657 | DyLight ® 633 | 638 | 658 |
| Seta 640 | 640 | 656 | CF ™ 640R | 642 | 642 |
| ATTO 647N | 644 | 669 | Quasar ® 670 | 644 | 670 |
| ATTO 647 | 645 | 669 | DY-636 | 645 | 671 |
| BODIPY ® 650/665 | 646 | 660 | Seta 646 | 646 | 656 |
| DY 635 | 647 | 671 | Square 635 | 647 | 666 |
| Cy 5 | 649 | 650/670 | Alexa Fluor ® 647 | 650 | 668 |
| CF ™ 647 | 650 | 665 | Seta 650 | 651 | 671 |
| Square 650 | 653 | 671 | DY-647 | 653 | 672 |
| DY-648 | 653 | 674 | DY-650 | 653 | 674 |
| DyLight ® 649 | 654 | 673 | DY-652 | 654 | 675 |
| DY-649 | 655 | 676 | DY-651 | 656 | 678 |
| Square 660 | 658 | 677 | Seta 660 | 661 | 672 |
| Alexa Fluor ® 660 | 663 | 690 | ATTO 655 | 663 | 684 |
| Seta 665 | 667 | 683 | Square 670 | 667 | 685 |
| Set 670 | 667 | 686 | DY-675 | 674 | 699 |
| DY-677 | 673 | 604 | DY-676 | 674 | 699 |
| Alexa Fluor ® 680 | 679 | 702 | IRDye ® 700DX | 680 | 687 |
| ATTO 680 | 680 | 700 | CF ™ 680R | 680 | 701 |
| CF ™ 680 | 681 | 698 | Square 685 | 683 | 703 |
| DY-680 | 690 | 709 | DY-681 | 691 | 708 |
| DyLight ® 680 | 692 | 712 | Seta 690 | 693 | 714 |
| ATTO 700 | 700 | 719 | Alexa Fluor ® 700 | 702 | 723 |
| Seta 700 | 702 | 728 | ATTO 725 | 725 | 752 |
| ATTO 740 | 740 | 764 | Alexa Fluor ® 750 | 749 | 775 |
| Seta 750 | 750 | 779 | DyLight ® 750 | 752 | 778 |
| CF ™ 750 | 755 | 777 | CF ™ 770 | 770 | 797 |
| DyLight ® 800 | 777 | 794 | IRDye ® 800RS | 770 | 786 |
| IRDye ® 800 CW | 778 | 794 | Alexa Fluor ® 790 | 782 | 805 |
| CF ™ 790 | 784 | 806 | | | |

The asymmetric rhodamine compounds described herein can be used in combination with one or more additional fluorescent labels in a multiplex assay. Various embodiments of the present teachings may comprise a single multiplex reaction comprising at least eight different dyes. The at least eight dyes may comprise any eight of the above-listed dyes. In certain embodiments the set of eight dyes includes an asymmetric rhodamine compound as described herein along with an additional asymmetric rhodamine compound, such as described in PCT/US2019/67925. In other embodiments a single multiplex reaction comprising at least ten or at least twelve different dyes may be used, or any number of dyes within these ranges.

Also provided are compositions, such as a reaction mixture or master mix, comprising the described probe. In one embodiment, the composition for PCR, such as for real-time or quantitative PCR or end-point PCR, comprises at least one of the described probes. In one embodiment, the composition or reaction mixture or master mix for PCR (e.g., qPCR or end-point PCR) comprises probes for allowing for detection of 4 target nucleic acids and the described probe(s) allowing for detection of at least one of a 5th and/or a 6th target nucleic acid, each of the described probes consisting of a FRET donor moiety, i.e., fluorophore, and a FRET acceptor moiety, i.e., quencher, where the fluorophore has an emission maximum between about 650 and 720 nm. The absorbance maximum of the quencher as described herein is between 660-668 nm. The absorbance range of the quencher as described herein is 530-730 nm. In an alternate embodiment, labeling reagents are provided for conjugating the described fluorophore and quencher to an oligonucleotide of choice.

In addition, such a composition or reaction mixture or master mix may comprise one or several compounds and reagents selected from the following list: Buffer, applicable for a polymerase chain reaction, deoxynucleoside triphosphates (dNTPs), DNA polymerase having 5' to 3' exonuclease activity, at least one pair or several pairs of amplification primers and/or additional probes.

In some embodiments, the methods provided further comprise determining a genotype of the target polynucleotide using the amplification product. In some embodiments, the methods provided further comprise determining the copy number of the target polynucleotide using the amplification product.

The reference works, patents, patent applications, scientific literature and other printed publications, as well as accession numbers to Gen Bank database sequences that are referred to herein and specifically PCT/US2019/67925, are all hereby incorporated by reference in their entirety.

As those skilled in the art will appreciate, numerous changes and modifications may be made to the various embodiments of the present teachings without departing from the spirit of these teachings. It is intended that all such variations fall within the scope of these teachings.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001.

Chemical nomenclature for compounds described herein has generally been derived using the commercially-available ACD/Name 2014 (ACD/Labs) or ChemBioDraw Ultra 13.0 (Perkin Elmer).

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable subcombination. All combinations of the embodiments pertaining to the chemical groups represented by the variables are specifically embraced by the present disclosure and are disclosed herein just as if each and every combination was individually and explicitly disclosed, to the extent that such combinations embrace compounds that are stable compounds (i.e., compounds that can be isolated, characterized, and tested for biological activity). In addition, all subcombinations of the chemical groups listed in the embodiments describing such variables are also specifically embraced by the present disclosure and are disclosed herein just as if each and every such sub-combination of chemical groups was individually and explicitly disclosed herein.

Chemical Synthesis

Exemplary chemical entities useful in methods of the description will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups.

All general chemicals were purchased from commercial chemical companies such as Fisher Scientific, Acros, or Alfa Aesar. Silica gel (220-400 mesh) from Fisher Scientific was used for normal phase flash chromatography. Reverse phase chromatography was performed using octadecyl functionalized Silica gel from JT Baker. All chromatography solvent gradients were stepwise. Thin layer chromatography (TLC) was performed on aluminum backed silica gel slides from EM Science. Reverse phase TLC were performed on HPTLC RP18F Uniplate plates from Analtech. Developed spots were visualized with both long and short wavelength UV irradiation.

NMR spectra were determined on a Varian 400 MHz NMR referenced relative to a solvent peak. HPLC was performed on an Agilent 1200 HPLC with diode array detector and multiple channel wavelengths. Typical elutions were run at 1 ml/min with a gradient of acetonitrile and 0.1 M triethylammonium acetate (TEAA) through an Agilent Pursuit C8 150×4.6 mm 5μ column. LCMS data was obtained using an Agilent 1200 LC system coupled to a PE Sciex API 150 EX mass spectrometer. MS data was obtained by direct infusion on a API Sciex 4000 mass spectrometer.

Anhydrous solvents were manipulated under a nitrogen atmosphere with oven-dried syringes. As used herein, the term "aqueous workup' refers to a purification method comprising of the following steps: dissolving or diluting a reaction mixture in a stated organic solvent, washing with a stated aqueous solution or water, washing the combined organic layer once with saturated NaCl, drying the solution with anhydrous $Na_2SO_4$, filtering the drying agent, and removing the solvent in vacuo.

Example 1: Preparation of an Asymmetric Rhodamine Dye

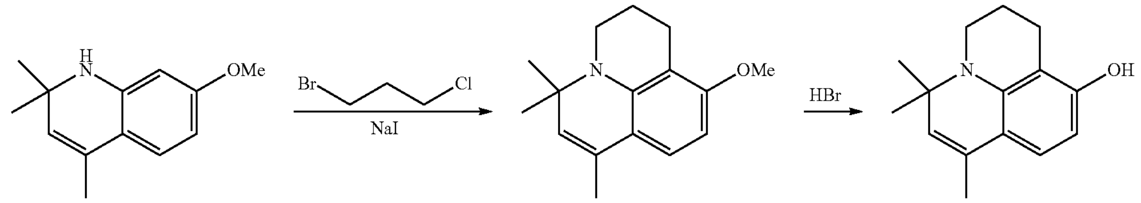

1 2 3

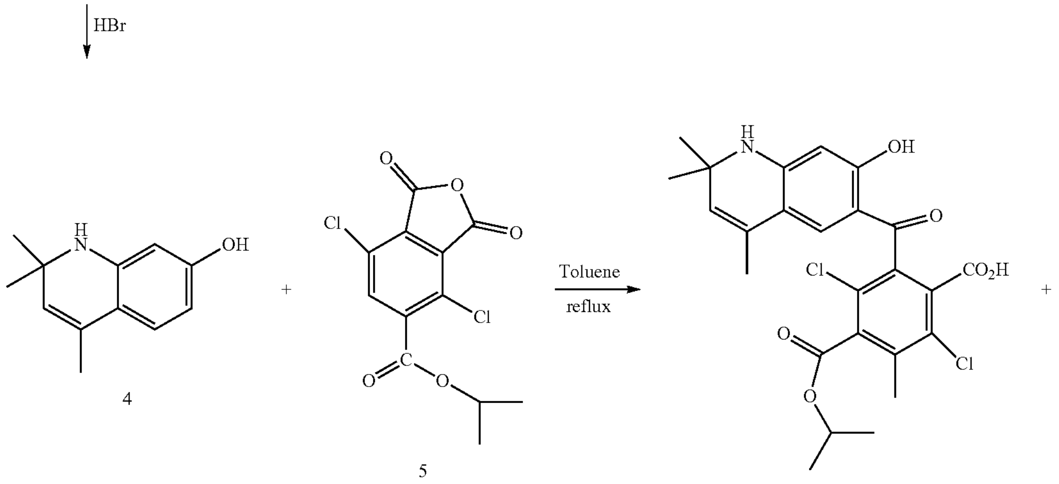

4 5 6

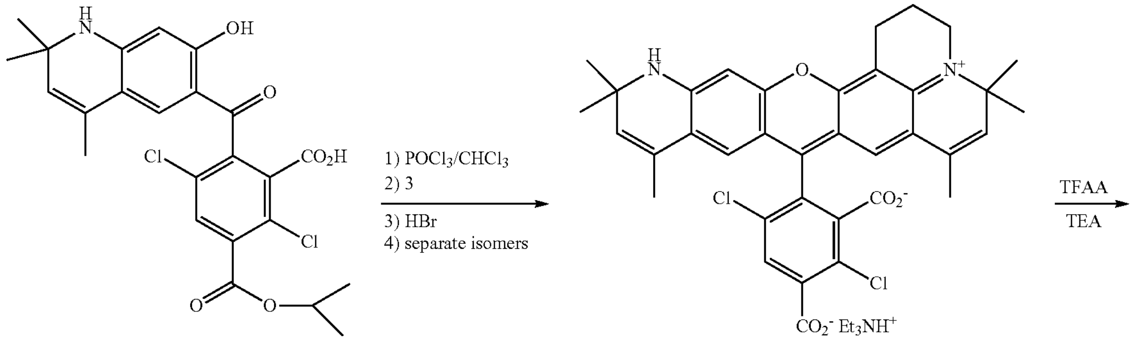

7 8

-continued

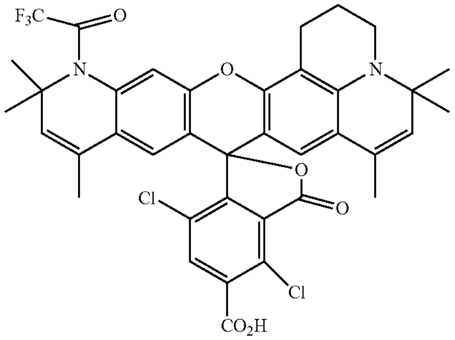

9

Step 1: Preparation of 10-methoxy-5,5,7-trimethyl-2,3-dihydro-1H,5H-pyrido[3,2,1-ij]quinoline, 2

7-Methoxy-2,2,4-trimethyl-1,2-dihydroquinoline, 1 (8.00 g, 39.4 mmol, A. Rosowsky, E. J. Modest, J O C, 1965, 30, 1832.), was dissolved in acetonitrile (125 ml) and mixed with 1-bromo-3-chloropropane (24.8 g, 157 mmol), sodium iodide (47.2 g, 315 mmol), and sodium carbonate (8.35 g, 78.8 mmol). The mixture was refluxed for 23 hr. The mixture was filtered, the filtrate concentrated, washed with water in DCM, and worked up. The crude residue was purified by silica gel flash chromatography eluting with 20% DCM/hexane to yield 2 as an off-white solid (8.28 g, 86%). $^1$H NMR (400 MHz, $CD_2Cl_2$): δ 6.85 (d, 1H), 6.15 (d, 1H), 5.15 (s, 1H), 3.75 (s, 3H), 3.22 (m, 2H), 2.59 (m, 2H), 1.90 (s, 3H), 1.87 (m, 2H), 1.28 (s, 6H). MS: calcd 244.17, observed 244.15 ($MH^+$).

Step 2: Preparation of 5,5,7-trimethyl-2,3-dihydro-1H,5H-pyrido[3,2,1-ij]quinolin-10-ol, 3

Compound 2 (8.28 g, 34.0 mmol) was refluxed with of hydrobromic acid (50 ml) for 1 hr. The solution was neutralized, in portions, with sodium bicarbonate. The mixture was extracted into EtOAc, the EtOAc layer washed with water and worked up to yield 3 as a pale orange solid (7.49 g, 98%). $^1$H NMR (400 MHz, $CD_2Cl_2$): δ 6.75 (d, 1H), 6.02 (d, 1H), 5.12 (s, 1H), 3.25 (m, 2H), 2.55 (m, 2H), 1.90 (m, 5H), 1.25 (s, 6H). MS: calcd 230.15, observed 230.13 ($MH^+$).

Step 3: Preparation of 2,2,4-trimethyl-1,2-dihydroquinolin-7-ol, 4

7-Methoxy-2,2,4-trimethyl-1,2-dihydroquinoline, 1 (10.00 g, 49.2 mmol) was refluxed with hydrobromic acid (50 ml) for 6 hr. The mixture was cooled to room temperature and then in an ice bath. The resulting solid was collected by suction filtration and washed with ice water. The solid was then mixed with 50% EtOAc/water and neutralized with sodium bicarbonate. The organic layer was retained, the aqueous layer extracted 2 times with EtOAc, the EtOAc layers combined, and worked up. The resulting solid was purified from hot DCM/hexane precipitation followed by silica gel flash chromatography eluting with 10%-20% EtOAc/hexane to yield 4 (Koelmel, Dominik K. et al., Organic & Biomolecular Chemistry, 2013, 11(24), 3954-3962) as an off-white/pale yellow solid (7.45 g, 80%). $^1$H NMR (400 MHz, $CD_2Cl_2$): δ 6.95 (m, 1H), 6.11 (m, 1H), 5.95 (s, 1H), 5.22 (s, 1H), 1.97 (s, 3H), 1.28 (s, 6H).

Step 4: Preparation 3,6-dichloro-2-(7-hydroxy-2,2,4-trimethyl-1,2-dihydroquinoline-6-carbonyl)-4-(isopropoxycarbonyl)benzoic acid, 6 and 7

2,2,4-Trimethyl-1,2-dihydroquinolin-7-ol, 4, (9.37 g, 49.5 mmol) and 3,6-dichlorotrimelletic acid isopropyl ester, 5, (18.01, 59.4 mmol; 5 was prepared according to the methods described in WO 2002/30944, incorporated herein by reference for the preparation of 5) were mixed in toluene (95 ml) and refluxed for 3.5 hr. After cooling, the toluene was removed and the resulting solid semi-purified by silica gel flash chromatography eluting with 5%-10% MeOH/DCM. The resulting solid was then further purified by silica gel flash chromatography eluting with 2% TEA/35% EtOAc/hexane followed by 100% EtOAc followed by 10%-15% MeOH/DCM. The resulting solid was then dissolved in DCM and washed twice with 1N HCl and worked up to yield 6/7 as a yellow-green solid (18.45 g, 71%). $^1$H NMR (400 MHz, $CD_2Cl_2$): δ 7.90 (d, 1H), 6.68 (d, 1H) 5.89 (s, 1H), 5.25 (m, 2H), 1.75 (d, 3H) 1.40 (m, 6H), 1.33 (s, 6H); MS: calcd 492.10 observed 492.08 ($MH^+$).

Step 4: Preparation of Asymmetric Rhodamine Dye 8

Compound 6 and 7 (19.79 g. 37.42 mmol) were dissolved in chloroform (400 ml) and mixed with phosphorous oxychloride (10.5 ml, 112 mmol) for 10 min at room temperature. Compound 3 (8.58 g, 37.4 mmol) was dissolved in chloroform (200 ml) and added to the compound 6/7/phosphorous oxychloride solution. A dark aqua-green color immediately forms. The solution was then refluxed for 3.5 hr to give a dark blue color. The solution was concentrated and the dark blue-black solid was then refluxed with hydrobromic acid (570 ml) with vigorous stirring for 1 hr. The hot solution was poured over ice to yield a fine blue solid which was collected by centrifugation and filtration and washed with water. The solid was mixed in a large volume of 2M triethylammonium acetate (TEAA), filtered to remove fine insolubles, and the isomers separated by loading onto a large reverse phase chromatography column and eluting with 50 mM TEAA followed by 60%-65%-70% MeOH/50 mM TEAA. The fractions were analyzed by HPLC before combining. The pool of dye 8 (second eluting dye by HPLC and RP-TLC) was diluted with an equal volume of water and desalted on a pad of C18 gel to yield, after concentration and drying, dye 8, a dark black-blue solid (8.79 g, 32%) as the TEA salt. $^{1}$H NMR (400 MHz, CD3OD): δ 7.55 (s, 1H), 6.92 (s, 1H), 6.81 (s, 1H), 6.61 (s, 1H), 5.60 (d, 2H), 3.61 (t, 2H), 3.16 (q, 6H), 2.94 (m, 2H), 2.02 (m, 2H), 1.87 (d, 6H), 1.50 (m, 6H), 1.39 (d, 6H), 1.27 (t, 9H); max absorbance wavelength 610 nm.

Step 5: Preparation of Asymmetric Rhodamine Dye 9

Dye 8 (5.25 g, 7.05 mmol) was dissolved in anhydrous DCM (300 ml), mixed with TEA (13.8 ml, 98.7 mmol), placed under nitrogen, and cooled in an ice bath. Trifluoroacetic anhydride (6.86 ml, 49.3 mmol) was added dropwise and the solution stirred for 0.5 hr. The now colorless solution was concentrated, re-dissolved in DCM and washed with sodium bicarbonate, 1N HCl, and worked up to yield compound 9.

Example 2: Preparation of Rhodamine Dye 9 Phosphoramidite

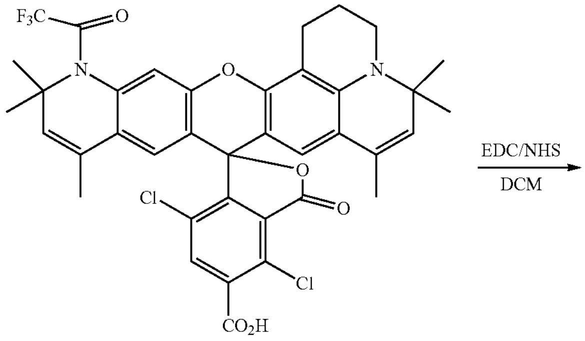

9

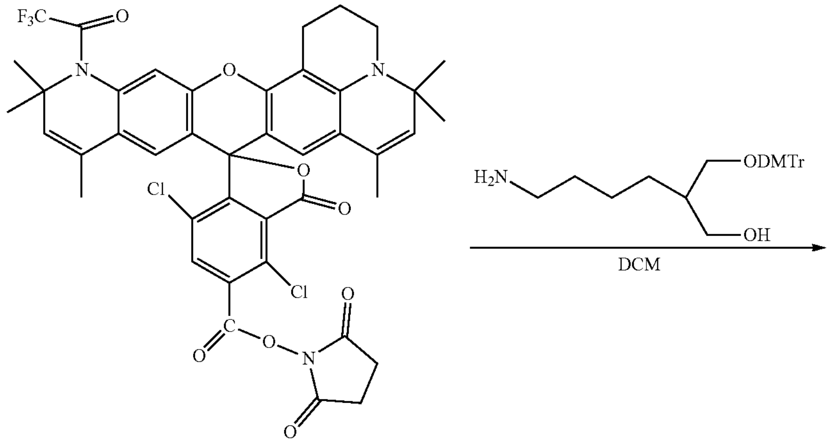

10

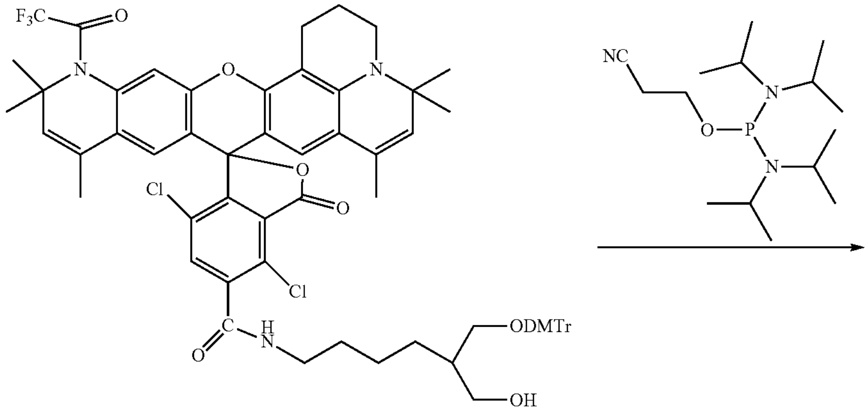

11

-continued

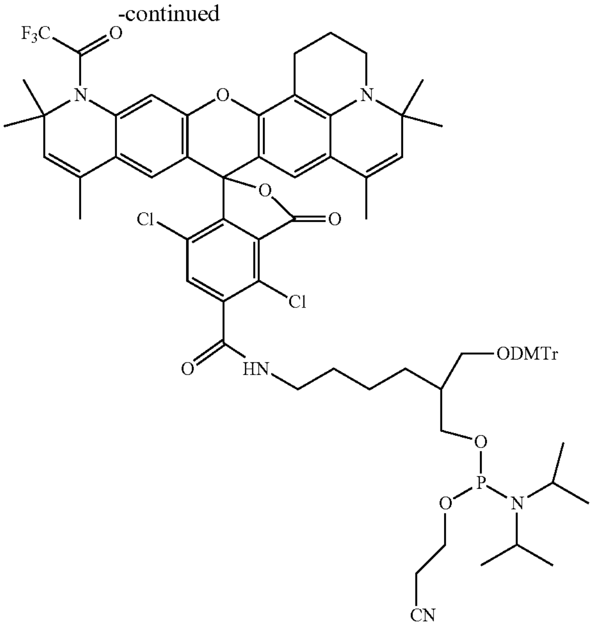

12

Step 1: Preparation of Rhodamine Dye 9 Activated Ester

Compound 9 was dissolved in anhydrous DCM (200 ml), mixed with N-hydroxysuccimide (1.62 g, 14.1 mmol), 1-ethyl-3-(3-dimethylaminopropyl)carbodiimide (EDC, 3.38 g, 17.6 mmol), and stirred for 1 hr. The solution was diluted with DCM, washed with 1N HCl, and worked up to compound 10.

Step 2: Preparation of N-Protected 6-amino-2-DMT hexan-1-ol Linker Rhodamine Dye, 11

Compound 10 was dissolved in anhydrous DMC (200 ml) and a solution of 6-amino-2-((bis(4-methoxyphenyl)(phenyl)methoxy)methyl)hexan-1-ol (4.12 g, 9.17 mmol) and triethylamine (1.47 ml, 10.6 mmol; TEA) was added dropwise. This was stirred at room temperature for 2 hr. The solution was diluted with DCM, washed with water, and worked up. The crude solid was purified using reverse phase column chromatography eluting with 95%-100% MeCN/water to yield compound 11 as a green solid (5.91 g, 72%). $^{1}$H NMR (400 MHz, $CD_2Cl_2$): δ 7.85 (s, 1H), 7.41 (m, 2H), 7.29 (m, 6H), 7.21 (m, 1H), 6.82 (m, 5H), 6.62 (s, 1H), 6.22 (s, 1H), 6.21 (m, 1H), 5.53 (s, 1H), 5.20 (s, 1H), 3.78 (s, 6H), 3.64 (m, 2H), 3.44 (m, 2H), 3.32 (m, 2H), 3.24 (m, 1H), 3.09 (m, 1H), 2.88 (t, 2H), 2.10 (broad t, 1H), 1.96 (m, 2H), 1.85 (d, 3H), 1.79 (m, 1H), 1.72 (d, 3H), 1.55 (m, 6H), 1.25-1.42 (m, 10H); MS: calcd 1170.40, observed 1170.34 ($MH^+$).

Step 3: Preparation of Rhodamine Dye 9 Phosphoramidite

Compound 11 (5.97 g, 5.10 mmol) and tetrazole amine (0.44 g, 2.54 mmol) were dissolved in anhydrous DCM (150 ml), stirred, and placed under nitrogen. 3A molecular sieves were added and further stirred 10 min. To this was added 2-cyanoethyl N,N,N',N'-tetraisopropylphosphorodiamidite (3.07 g, 10.2 mmol) and the mixture was stirred at room temperature for 1 hr. The molecular sieves were filtered off and the solution concentrated to a solid. This was purified by reverse phase column chromatography pre-treating the column with 20% TEA/MeCN and then washing well with MeCN. The sample was then dissolved in MeCN and eluted with MeCN. The pooled product-containing fractions were concentrated and dried to yield TFA-N-protected NH-asymmetric rhodamine dye phosphoramidite 12 as a dark yellow solid (6.13 g, 88%). $^{1}$H NMR (400 MHz, $CD_2Cl_2$): δ 7.77 (s, 1H), 7.43 (m, 2H), 7.30 (m, 6H), 7.20 (m, 1H), 6.82 (m, 5H), 6.66 (s, 1H), 6.31 (m, 1H), 6.24 (s, 1H), 5.53 (s, 1H), 5.21 (s, 1H), 3.78-3.64 (s and m, 10H), 3.57 (m, 2H), 3.43 (q, 2H), 3.32 (t, 2H), 3.11 (m, 2H), 2.89 (t, 2H), 2.54 (q, 2H), 1.97 (m, 2H), 1.92-1.84 (m, 4H), 1.73 (s, 3H), 1.61 (m, 2H), 1.51 (d, 6H), 1.45 (m, 2H), 1.40-1.28 (s and m, 8H), 1.50 (m, 12H); $^{31}$P NMR (400 MHz, $CD_2Cl_2$): δ 147.4 (s, 1P); MS calcd 1370.51, observed 1370.57 ($MH^+$)

Example 3: Solid Phase Synthesis of a Big Dye Asymmetric Rhodamine Labeled Oligonucleotide

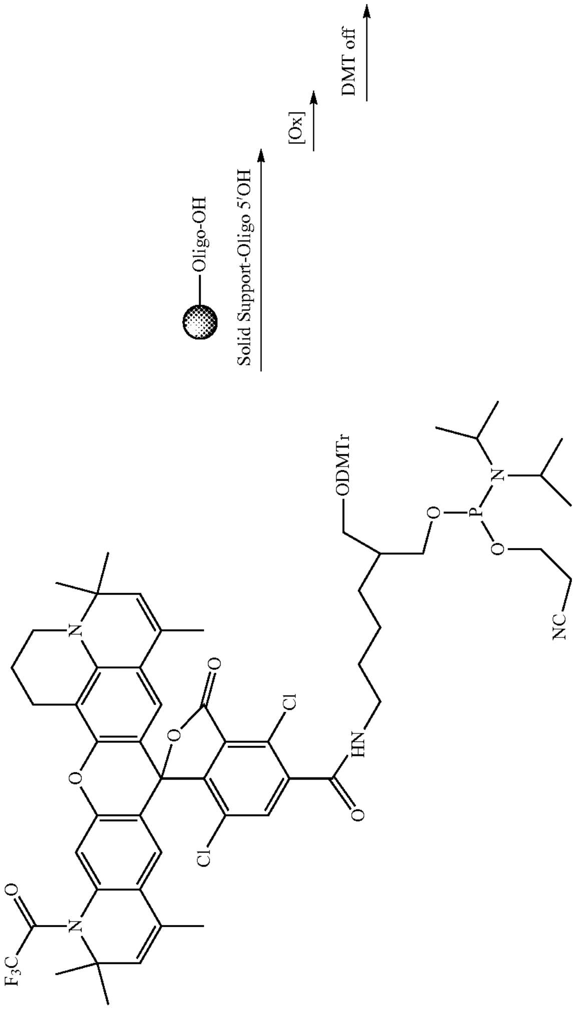
12

-continued
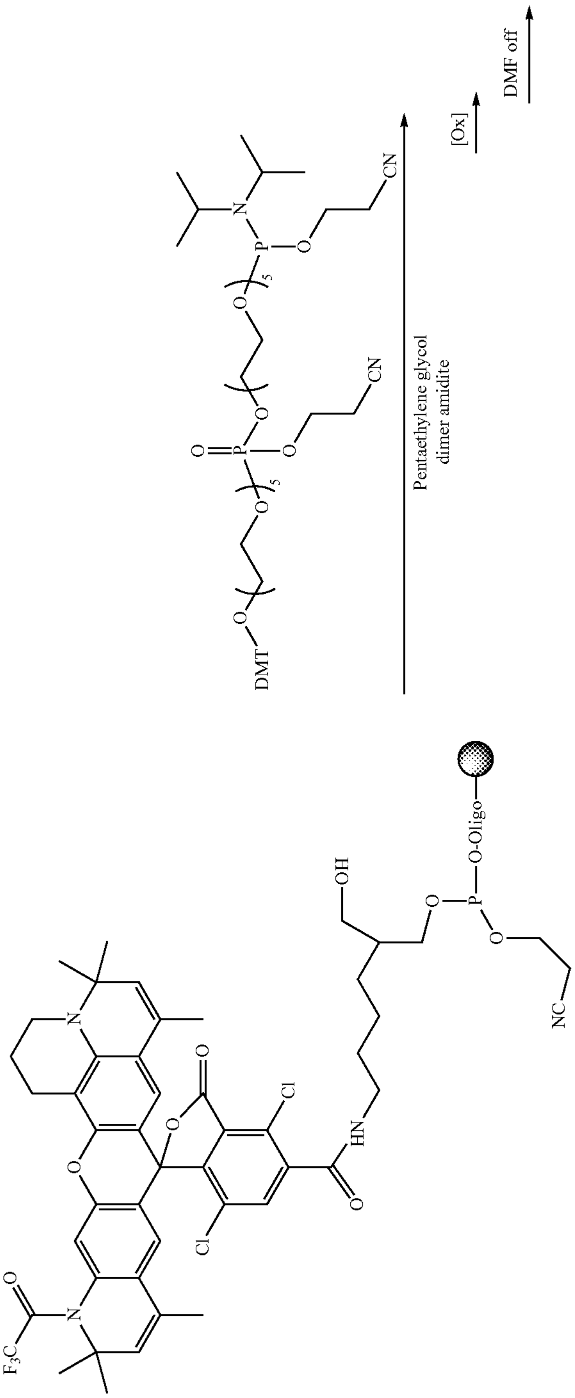
13

-continued
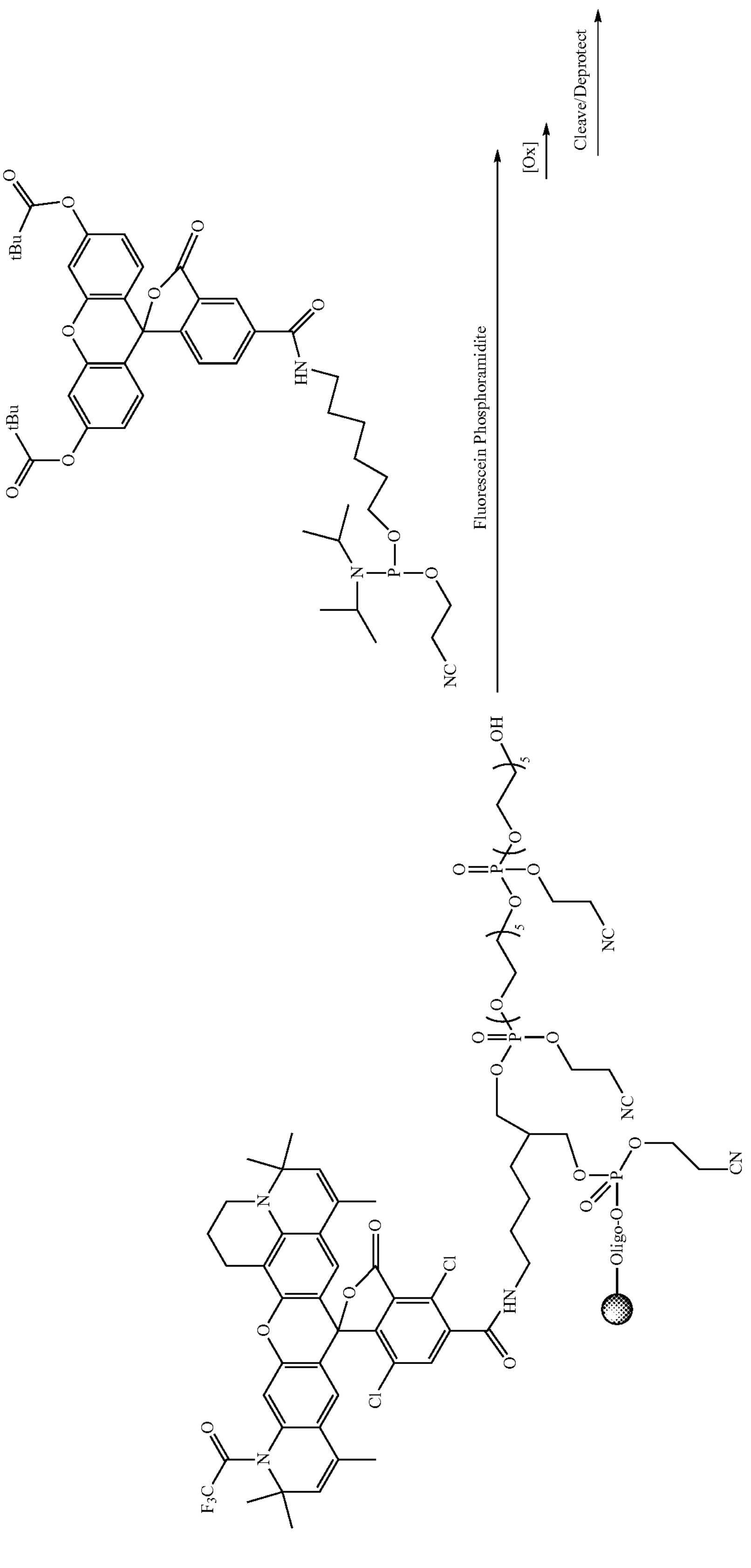
14

-continued
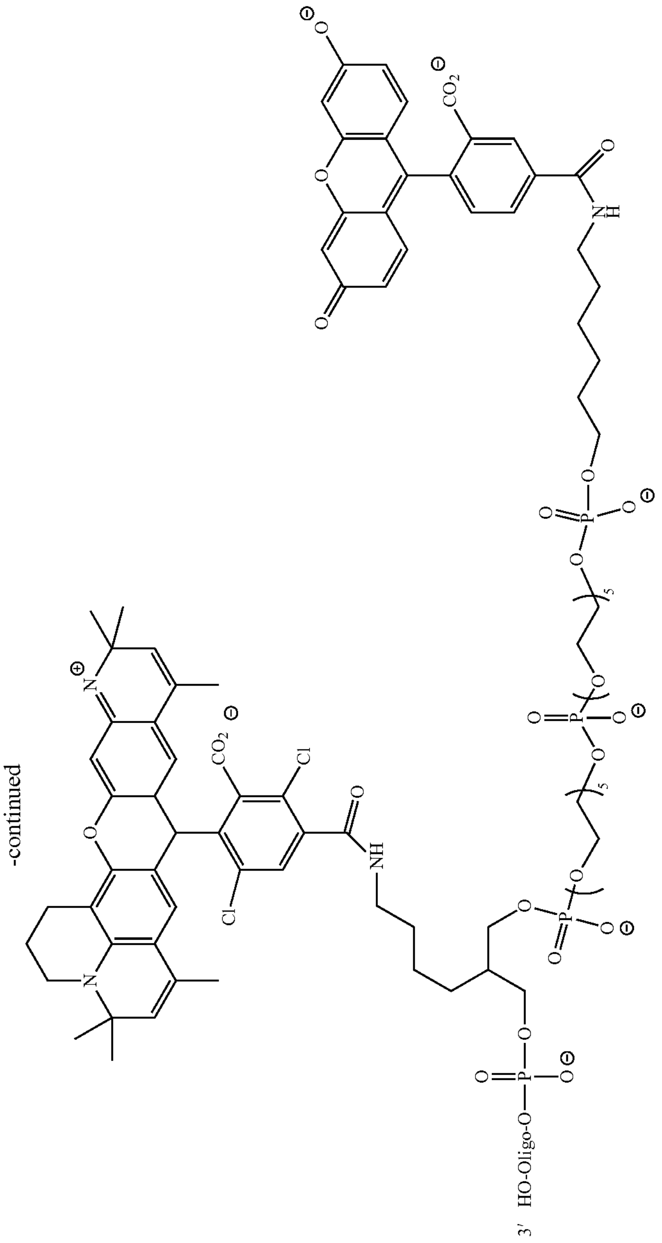

Oligonucleotides labeled with the N-protected asymmetric rhodamine phosphoramidite synthesis reagents were synthesized on polystyrene solid supports using the standard operating conditions on a Biolytic 3900 automated DNA synthesizer. The N-protected asymmetric rhodamine phosphoramidite 12 was dissolved in acetonitrile solvent for the coupling reactions, and the N-protected asymmetric rhodamine dye adducts were stable to repeated synthesis cycles which employed removal of DMT with trichloroacetic acid, addition of other specialty phosphoramidites, capping with acetic anhydride, and oxidation with iodine to generate the internucleotide phosphodiester linkages. This class of asymmetric rhodamine was also found to be stable to the conditions used to deprotect and cleave the synthesized labeled oligonucleotide from the solid support (treatment with a solution containing t-butylamine/methanol/water at 65° C. for five hours). The overall scheme used to synthesize the labeled oligonucleotide is illustrated in the scheme above. By this process, mono TFA-asymmetric rhodamine DMT phosphoramidite 12 was coupled to the 5'-hydroxyl of a support-bound oligo nucleotide to give the phosphodiester intermediate 13 after oxidation and removal of the DMT group. PEG dimer phosphoramidite was coupled to the free hydroxyl of intermediate 13 to give intermediate 14 after oxidation, capping, and removal of DMT. Fluorescein phosphoramidite (ThermoFisher) was coupled to the free hydroxyl of intermediate 14. The resultant labeled oligo was oxidized, capped, cleaved, and deprotected from the support to yield labeled oligonucleotide 15. Oligo 15 was purified using standard chromatographic protocols.

The disclosure may be further described by the following numbered clauses.

1. A compound of the formula wherein

R1, R2, R3, R6, R7, R8, R11, R12, R13, and R14, when taken alone, are each independently of one another selected from hydrogen, lower alkyl, (C6-C14) aryl, (C7-C20) arylalkyl, 5-14 membered heteroaryl, 6-20 membered heteroarylalkyl, —Rb, or —$(CH_2)$n-Rb; or alternatively, R1 and R2 and/or R6 and R7 are taken together with the carbon atoms to which they are bonded to form an optionally substituted benzo group;

R4, when taken alone, is selected from hydrogen, lower alkyl, (C6-C14) aryl, (C7-C20) arylalkyl, 5-14 membered heteroaryl, 6-20 membered heteroarylalkyl; or R4 and one of R2 or R3 are taken together with the atoms to which they are bonded to form an optionally substituted heterocycloalkyl group, an optionally substituted heterocycloalkenyl group, or an optionally substituted heteroaryl group;

R5 is H or a protecting group;

R9, when taken alone, is selected from hydrogen, lower alkyl, (C6-C14) aryl, (C7-C20) arylalkyl, 5-14 membered heteroaryl, 6-20 membered heteroarylalkyl; or R7 and R9 are taken together with the atoms to which they are bonded to form an optionally substituted heterocycloalkyl group, an optionally substituted heterocycloalkenyl group, or an optionally substituted heteroaryl group;

R10 is H or protecting group; or R8 and R10 are taken together with the atoms to which they are bonded to form an optionally substituted heterocycloalkyl group, an optionally substituted heterocycloalkenyl group, or an optionally substituted heteroaryl group;

at least one of R7 and R9 or R8 and R10 are taken together with the atoms to which they are bonded to form an optionally substituted heterocycloalkyl group, an optionally substituted heterocycloalkenyl group, or an optionally substituted heteroaryl group, and optionally, R4 and one of R2 or R3 are taken together with the atoms to which they are bonded to form an optionally substituted heterocycloalkyl group, an optionally substituted heterocycloalkenyl group, or an optionally substituted heteroaryl group, with the proviso that compound is not of the formula, or;

each Ra is independently selected from lower alkyl, (C6-C14) aryl, (C7-C20) arylalkyl, 5-14 membered heteroaryl, —CX3 and 6-20 membered heteroarylalkyl;

each Rb is independently selected from —X, —OH, —$OR^a$, —SH, —SRa—NH2, —NHRa, —NRcRc, —N+RcRcRc, perhalo lower alkyl, trihalomethyl, trifluoromethyl, —P(O)(OH)2, —P(O)(ORa)2, P(O)(OH)(ORa), —OP(O)(OH)2, —OP(O)(ORa)2, —OP(O)(ORa)(OH), —S(O)2OH, —S(O)2Ra, —C(O)H, —C(O)Ra, —C(S)X, —C(O)ORa, —C(O)OH, —C(O)NH2, —C(O)NHRa, —C(O)NRcRc, —C(S)NH2, —C(O)NHRa, —C(O)NRcRc, —C(NH)NH2, —C(NH)NHRa, and —C(NH)NRcRc;

each Rc is independently an $R^a$, or, alternatively, two Rc bonded to the same nitrogen atom may be taken together with that nitrogen atom to form a 5- to 8-membered saturated or unsaturated ring that may optionally include one or more of the same or different ring heteroatoms selected from O, N, and S;

each Rd and Re, when taken alone, is independently selected from hydrogen, lower alkyl, (C6-C14) aryl, (C7-C20) arylalkyl, 5-14 membered heteroaryl, 6-20 membered heteroarylalkyl, —Rb, or —$(CH_2)$n-Rb;

X is halo; and n is an integer ranging from 1 to 10.

2. The compound of clause 1 wherein the spirolactone ring is in open, acid form and the amine groups are not protected. In certain embodiments, the open, acid form of the compound is fluorescent (or exhibits an increase in fluorescence) relative to the closed, spirolactone form of the compound. The amine groups of the compounds described herein are protectable in the closed, spirolactone form and can be made into and used as phosphoramidites for high yield and high purity labeling of nucleic acids. Thus, also provided herein are fluorescently-labeled nucleic acid probes and primers that include a compound of clause 1 in deprotected, open lactone form. Representative examples of compounds of clause 1 in the open lactone form after deprotection of the amine groups and cleavage of the nucleic acid probe from a solid support are shown in FIGS. 8 and 9.

Thermo Fisher Scientific offers an HID kit that includes reagents for labeling nucleic acids with 5 reporter dyes (i.e., FAM, VIC, TED, TAZ, and SID) and a size standard LIZ (NGM Detect™ PCR Amplification Kit). Certain dyes provided herein have unique spectral properties that complement those in the existing dye set and can be used to expand the number of reporter dyes that can be included for HID applications. In particular, it was found that certain asymmetric rhodamines described in clause 1 exhibit a peak emission wavelength and a narrow spectral width such that they can be resolved from other dyes within the existing commercial dye set. For example, representative compounds that exhibit a peak emission wavelength (e.g., ~634 nm) belong to the class of asymmetric rhodamine compounds shown in structure D.1. Applicant further discovered that by replacing VIC with two new dyes, the existing HID dye set could be expanded to include 7 or more reporter dyes. In certain embodiments, an asymmetric rhodamine having a structure as described in PCT/US2019/67925 (Cmpd A) and TET (~536 nm) are used as a replacement for VIC in a kit that further includes the asymmetric rhodamine of structure D.1 (Cmpd B) and FAM, TED, TAZ, and SID (FIG. 10). Such compounds are well resolved from the neighboring emission peaks of SID (~617) and LIZ (~653 nm) in the proposed dye set. Thus, certain kits provided herein can include nucleic acids labeled with (or reagents for labeling nucleic acids) a compound as described in clause 1 (e.g., a compound having structure D.1) with emission at ~634 nm, FAM, TET, TED, TAZ and SID.

3. An oligonucleotide comprising a label moiety produced by reacting an oligonucleotide attached to a solid support with a reagent have a structure of formula:

LM-L-PEP wherein PEP is a phosphate ester precursor group, L is an optional linker linking the label moiety to the PEP group, and LM comprises an N-protected NH-rhodamine moiety of the formula (I) wherein R1, R2, R3, R6, R7, R8, R11, R12, R13, and R14, when taken alone, are each independently of one another selected from hydrogen, lower alkyl, (C6-C14) aryl, (C7-C20) arylalkyl, 5-14 membered heteroaryl, 6-20 membered heteroarylalkyl, —Rb, or —$(CH_2)$n-Rb; or alternatively, R1 and R2 and/or R6 and R7 are taken together with the carbon atoms to which they are bonded to form an optionally substituted benzo group; and one of R2, R3, R7, R8, R12, or R13 comprises a group of the formula —Y—, wherein Y is selected from the group consisting of —C(O)—, —S(O)2-, —S— and —NH—;

R4, when taken alone, is selected from hydrogen, lower alkyl, (C6-C14) aryl, (C7-C20) arylalkyl, 5-14 membered heteroaryl, 6-20 membered heteroarylalkyl; or R4 and one of R2 or R3 are taken together with the atoms to which they are bonded to form an optionally substituted heterocycloalkyl group, an optionally substituted heterocycloalkenyl group, or an optionally substituted heteroaryl group;

R5 is H or a protecting group;

R9, when taken alone, is selected from hydrogen, lower alkyl, (C6-C14) aryl, (C7-C20) arylalkyl, 5-14 membered heteroaryl, 6-20 membered heteroarylalkyl; or R7 and R9 are taken together with the atoms to which they are bonded to form an optionally substituted heterocycloalkyl group, an optionally substituted heterocycloalkenyl group, or an optionally substituted heteroaryl group;

R10 is H or protecting group; or R8 and R10 are taken together with the atoms to which they are bonded to form an optionally substituted heterocycloalkyl group, an optionally substituted heterocycloalkenyl group, or an optionally substituted heteroaryl group;

at least one of R7 and R9 or R8 and R10 are taken together with the atoms to which they are bonded to form an optionally substituted heterocycloalkyl group, an optionally substituted heterocycloalkenyl group, or an optionally substituted heteroaryl group, and optionally, R4 and one of R2 or R3 are taken together with the atoms to which they are bonded to form an optionally substituted heterocycloalkyl group, an optionally substituted heterocycloalkenyl group, or an optionally substituted heteroaryl group, with the proviso that compound is not of the formula, or;

each Ra is independently selected from lower alkyl, (C6-C14) aryl, (C7-C20) arylalkyl, 5-14 membered heteroaryl, —CX3 and 6-20 membered heteroarylalkyl;

each Rb is independently selected from X, —OH, —ORa—SH, —SRa—NH2, —NHRa—NRcRc, —N+RcRcRc, perhalo lower alkyl, trihalomethyl, trifluoromethyl, —P(O)(OH)2, —P(O)(ORa)2, P(O)(OH)(ORa), —OP(O)(OH)2, —OP(O)(ORa)2, —OP(O)(ORa)(OH), —S(O)2OH, —S(O)2Ra, —C(O)H, —C(O)Ra, —C(S)X, —C(O)ORa, —C(O)OH, —C(O)NH2, —C(O)NHRa, —C(O)NRcRc, —C(S)NH2, —C(O)NHRa, —C(O)NRcRc, —C(NH)NH2, —C(NH)NHRa, and —C(NH)NRcRc;

each Rc is independently an Ra, or, alternatively, two Rc bonded to the same nitrogen atom may be taken together with that nitrogen atom to form a 5- to 8-membered saturated or unsaturated ring that may optionally include one or more of the same or different ring heteroatoms selected from O, N, and S;

each Rd and Re, when taken alone, is independently selected from hydrogen, lower alkyl, (C6-C14) aryl, (C7-C20) arylalkyl, 5-14 membered heteroaryl, 6-20 membered heteroarylalkyl, —Rb, or —$(CH_2)$n-Rb;

X is halo; and n is an integer ranging from 1 to 10.

4. The oligonucleotide of clause 3 wherein the spirolactone ring is in open, acid form and the amine groups are not protected.

5. A reagent useful for labeling an oligonucleotide, which is a compound according to the structural formula:

LM-L-PEP (XX)

wherein LM represents a label moiety that comprises an N-protected NH-rhodamine moiety, PEP is a phosphate ester precursor group which comprises a phosphoramidite group or an H-phosphonate group, and L is an optional linker linking the label moiety to the phosphate ester precursor group, in which the N-protected NH-rhodamine moiety of the formula wherein R1, R2, R3, R6, R7, R8, R11, R12, R13, and R14, when taken alone, are each independently of one another selected from hydrogen, lower alkyl, (C6-C14) aryl, (C7-C20) arylalkyl, 5-14 membered heteroaryl, 6-20 membered heteroarylalkyl, —Rb, or —$(CH_2)$n-Rb; or alternatively, R1 and R2 and/or R6 and R7 are taken together with the carbon atoms to which they are bonded to form an optionally substituted benzo group; and one of R2, R3, R7, R8, R12, or R13 comprises a group of the formula —Y—, wherein Y is selected from the group consisting of —C(O)—, —S(O)2-, —S— and —NH—;

R4, when taken alone, is selected from hydrogen, lower alkyl, (C6-C14) aryl, (C7-C20) arylalkyl, 5-14 membered heteroaryl, 6-20 membered heteroarylalkyl; or R4 and one of R2 or R3 are taken together with the atoms to which they are bonded to form an optionally substituted heterocycloalkyl group, an optionally substituted heterocycloalkenyl group, or an optionally substituted heteroaryl group;

R5 is H or a protecting group;

R9, when taken alone, is selected from hydrogen, lower alkyl, (C6-C14) aryl, (C7-C20) arylalkyl, 5-14 membered heteroaryl, 6-20 membered heteroarylalkyl; or R7 and R9 are taken together with the atoms to which they are bonded to form an optionally substituted heterocycloalkyl group, an optionally substituted heterocycloalkenyl group, or an optionally substituted heteroaryl group;

R10 is H or protecting group; or R8 and R10 are taken together with the atoms to which they are bonded to form an optionally substituted heterocycloalkyl group, an optionally substituted heterocycloalkenyl group, or an optionally substituted heteroaryl group;

at least one of R7 and R9 or R8 and R10 are taken together with the atoms to which they are bonded to form an optionally substituted heterocycloalkyl group, an optionally substituted heterocycloalkenyl group, or an optionally substituted heteroaryl group, and optionally, R4 and one of R2 or R3 are taken together with the atoms to which they are bonded to form an optionally substituted heterocycloalkyl group, an optionally substituted heterocycloalkenyl group, or an optionally substituted heteroaryl group, with the proviso that compound is not of the formula, or;

each Ra is independently selected from lower alkyl, (C6-C14) aryl, (C7-C20) arylalkyl, 5-14 membered heteroaryl, —CX3 and 6-20 membered heteroarylalkyl;

each Rb is independently selected from X, —OH, —ORa—SH, —SRa—NH2, —NHRa—NRcRc, —N+RcRcRc, perhalo lower alkyl, trihalomethyl, trifluoromethyl, —P(O)(OH)$_2$, —P(O)(ORa)2, P(O)(OH)(ORa), —OP(O)(OH)2, —OP(O)(ORa)2, —OP(O)(ORa)(OH), —S(O)2OH, —S(O)2Ra, —C(O)H, —C(O)Ra, —C(S)X, —C(O)ORa, —C(O)OH, —C(O)NH2, —C(O)NHRa, —C(O)NRcRc, —C(S)NH2, —C(O)NHRa, —C(O)NRcRc, —C(NH)NH2, —C(NH)NHRa, and —C(NH)NRcRc;

each Rc is independently an Ra, or, alternatively, two Rc bonded to the same nitrogen atom may be taken together with that nitrogen atom to form a 5- to 8-membered saturated or unsaturated ring that may optionally include one or more of the same or different ring heteroatoms selected from O, N, and S;

each Rd and Re, when taken alone, is independently selected from hydrogen, lower alkyl, (C6-C14) aryl, (C7-C20) arylalkyl, 5-14 membered heteroaryl, 6-20 membered heteroarylalkyl, —Rb, or —(CH2)n-Rb;

X is halo; and n is an integer ranging from 1 to 10.

6. The reagent of clause 5 wherein the spirolactone ring is in open, acid form and the amine groups are not protected.

What is claimed is:

1. A compound wherein the compound is compound 9

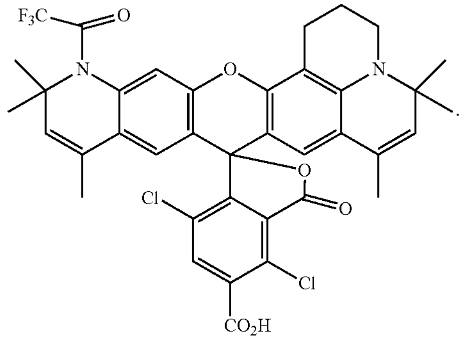

* * * * *